(12) United States Patent
Romaniello et al.

(10) Patent No.: US 11,896,930 B2
(45) Date of Patent: Feb. 13, 2024

(54) CARBON-REMOVING SAND AND METHOD AND PROCESS FOR DESIGN, MANUFACTURE, AND UTILIZATION OF THE SAME

(71) Applicant: Project Vesta, PBC, San Francisco, CA (US)

(72) Inventors: Stephen Justin Romaniello, Knoxville, TN (US); Brian David Ley, Hawi, HI (US); Margaret Grace Andrews, Montclair, NJ (US); Nathan Gerard Walworth, Los Angeles, CA (US); Thomas Ishoey, San Diego, CA (US); Tom Coxeter Green, San Francisco, CA (US); Francesc Montserrat, Capelle aan den Ussel (NL); Chloe Sarah Leach, Newark and Sherwood (GB); David L. Kriebel, Kennett Square, PA (US); Devon Barnes Cole, Salt Lake City, UT (US); Geoffrey Wadsworth Calkins, Durango, CO (US); Douglas Owen Edwards, Denver, CO (US)

(73) Assignee: PROJECT VESTA, PBC, San Francisco, CA (US)

(*) Notice: Subject to any disclaimer, the term of this patent is extended or adjusted under 35 U.S.C. 154(b) by 0 days.

(21) Appl. No.: 18/328,943

(22) Filed: Jun. 5, 2023

(65) Prior Publication Data

US 2023/0364554 A1 Nov. 16, 2023

Related U.S. Application Data

(63) Continuation of application No. PCT/US2022/078323, filed on Oct. 18, 2022.

(60) Provisional application No. 63/256,986, filed on Oct. 18, 2021, provisional application No. 63/281,575, filed on Nov. 19, 2021, provisional application No. 63/298,412, filed on Jan. 11, 2022, provisional application No. 63/403,446, filed on Sep. 2, 2022, provisional application No. 63/377,171, filed on Sep. 26, 2022.

(51) Int. Cl.
| | | |
|---|---|---|
| B01D 53/14 | (2006.01) | |
| B01D 53/62 | (2006.01) | |
| B01D 53/78 | (2006.01) | |
| B01D 53/82 | (2006.01) | |
| B01J 20/10 | (2006.01) | |
| G01N 33/00 | (2006.01) | |
| G06N 5/022 | (2023.01) | |

(52) U.S. Cl.
CPC ......... *B01D 53/62* (2013.01); *B01D 53/1475* (2013.01); *B01D 53/78* (2013.01); *B01D 53/82* (2013.01); *B01J 20/103* (2013.01); *G01N 33/004* (2013.01); *G06N 5/022* (2013.01); *B01D 2251/402* (2013.01); *B01D 2252/1035* (2013.01); *B01D 2257/504* (2013.01); *B01D 2258/06* (2013.01); *B01D 2259/128* (2013.01)

(58) Field of Classification Search
CPC ........ B01D 53/62; B01D 53/82; B01D 53/78; B01D 53/1475; B01D 2251/402; B01D 2257/504; B01D 2258/06; B01D 2259/128; B01D 2252/1035; B01J 20/103; G06N 5/022; G01N 33/004; Y02C 20/40; A61L 9/00
See application file for complete search history.

(56) References Cited

U.S. PATENT DOCUMENTS

| | | |
|---|---|---|
| 7,415,418 B2 | 8/2008 | Zimmerman et al. |
| 7,604,787 B2 | 10/2009 | Maroto-Valer et al. |
| 7,682,589 B2 | 3/2010 | Gorset et al. |
| 7,722,842 B2 | 5/2010 | Park et al. |
| 7,722,850 B2 | 5/2010 | Geerlings et al. |
| 7,749,476 B2 | 7/2010 | Constantz et al. |
| 7,815,880 B2 | 10/2010 | Constantz et al. |
| 7,966,250 B2 | 6/2011 | Constantz et al. |
| 8,114,374 B2 | 2/2012 | Blencoe et al. |
| 8,137,444 B2 | 3/2012 | Farsad et al. |
| 9,152,994 B2 | 10/2015 | Marino |

(Continued)

FOREIGN PATENT DOCUMENTS

| | | | | |
|---|---|---|---|---|
| JP | 2 749 976 B2 * | 5/1998 | ............ | Y02P 20/151 |
| WO | WO 2008 142 017 A2 * | 11/2008 | ................ | C01F 5/24 |

(Continued)

OTHER PUBLICATIONS

C. Doughty et al. "Capacity investigation of brine-bearing sands for geologic sequestration or CO{sub2}" Conf. 6. International Conf. on greenhouse gas control technologies: GHGT-6, Kyoto (Japan), Oct. 1-4, 2002, ISBN 0-08-044276-5; TRN: 000100127. (Year: 2003).*

(Continued)

*Primary Examiner* — Timothy C Vanoy
(74) *Attorney, Agent, or Firm* — Wilson Sonsini Goodrich & Rosati

(57) ABSTRACT

The invention includes systems, methods, compositions, and processes for designing, manufacturing, and utilizing carbon dioxide-sequestering substrates that can fully or partially replace natural sand in coastal engineering applications. These engineered substrates can offset demand for scarce native sand resources, while also effecting the conversion of gaseous carbon dioxide to dissolved or solid-phase products thereby offsetting impacts of anthropogenic climate change.

19 Claims, 49 Drawing Sheets

(56) References Cited

U.S. PATENT DOCUMENTS

| | | | |
|---|---|---|---|
| 9,514,493 | B2 | 12/2016 | Marino |
| 9,527,747 | B2 | 12/2016 | Wright et al. |
| 11,389,761 | B1* | 7/2022 | Stark, Jr. ............ B01D 53/0476 |
| 2009/0043687 | A1 | 2/2009 | van Soestbergen et al. |
| 2010/0120104 | A1 | 5/2010 | Reed |
| 2010/0221163 | A1* | 9/2010 | DaCosta ............... B01D 53/62 |
| | | | 422/139 |
| 2010/0251937 | A1 | 10/2010 | Murray et al. |
| 2011/0038774 | A1* | 2/2011 | Zhong ..................... C01B 7/055 |
| | | | 423/234 |
| 2011/0212479 | A1 | 9/2011 | Rodgers |
| 2011/0214535 | A1 | 9/2011 | Vandor |
| 2013/0266380 | A1 | 10/2013 | Capron et al. |
| 2014/0322083 | A1 | 10/2014 | Kuppler et al. |
| 2015/0157979 | A1 | 6/2015 | Park et al. |
| 2016/0355442 | A1 | 12/2016 | Niven et al. |
| 2017/0029284 | A1* | 2/2017 | Priestnall .................. C01F 5/22 |
| 2017/0291139 | A1 | 10/2017 | Blencoe et al. |

FOREIGN PATENT DOCUMENTS

| | | |
|---|---|---|
| WO | WO-2010048457 A1 | 4/2010 |
| WO | WO-2012068639 A1 | 5/2012 |
| WO | WO-2023069960 A1 | 4/2023 |

OTHER PUBLICATIONS

Ahrens, et al. Velocity parameters for predicting cross-shore sediment movement. Journal of waterway, port, coastal, and ocean engineering 124, No. 1 (1998): 16-20.

Bach, et al. CO2 removal with enhanced weathering and ocean alkalinity enhancement: potential risks and co-benefits for marine pelagic ecosystems. Front. Clim., Oct. 11, 2019. Volume 1. Article 7. pp. 1-21. https://doi.org/10.3389/fclim.2019.00007.

Bearat, et al. Carbon sequestration via aqueous olivine mineral carbonation: role of passivating layer formation. Environ Sci Technol. Aug. 1, 2006;40(15):4802-8. doi: 10.1021/es0523340.

Beerling, et al. Potential for large-scale CO2 removal via enhanced rock weathering with croplands. Nature 583(7815):242-248 (2021). doi: 10.1038/s41586-020-2448-9.

Berghe, et al. Silicate minerals as a direct source of limiting nutrients: Siderophore synthesis and uptake promote ferric iron bioavailability from olivine and microbial growth. Geobiology 19(6):618-630 (2021). doi: 10.1111/gbi.12457.

Berner, et al. The carbonate-silicate geochemical cycle and its effect on atmospheric carbon dioxide over the past 100 million years. Amer J Sci 283(7):641-683 (1983). DOI: 10.2475/ajs.283.7.641.

Berner, R.A. The Phanerozoic Carbon Cycle CO2 and O2. Oxford University Press Aug. 19, 2004. 158 pgs. (Table of Contents).

Chmura, et al. Global carbon sequestration in tidal, saline wetland soils. Global Biogeochemical Cycles 17(4):22-1-22-12 (2003). https://doi.org/10.1029/2002GB001917.

Co-pending U.S. Appl. No. 18/303,467, inventors Romaniello; Stephen J et al., filed Apr. 19, 2023.

Crundwell, F.K. The mechanism of dissolution of forsterite, olivine and minerals of the orthosilicate group. Hydrometallurgy 150:68-82 (2014). https://doi.org/10.1016/j.hydromet.2014.09.006.

Daval, et al. Influence of amorphous silica layer formation on the dissolution rate of olivine at 90 and elevated pCO2. Chemical Geology 284(1-2):193-209 (2011). DOI:10.1016/j.chemgeo.2011.02.021.

Declercq, et al. Do organic ligands affect forsterite dissolution rates? Appl Geochem 39:69-77 (2013). DOI:10.1016/j.apgeochem.2013.09.020.

Diallo, et al. Mining Critical Metals and Elements from Seawater: Opportunities and Challenges. Environ. Sci. Technol. 2015, 49, 16, 9390-9399. DOI: 10.1021/acs.est.5b00463.

European search report and opinion dated Sep. 2, 2022 for EP Application No. 22157366.0.

Feng, et al. Model-Based Assessment of the CO2 Sequestration Potential of Coastal Ocean Alkalinization. Earth's Future 5(12): 1252-66 (2017). https://doi.org/10.1002/2017ef000659.

Fuhr, et al. Kinetics of Olivine Weathering in Seawater: An Experimental Study. Front Clim 4(831587): 1-20 (Mar. 2022). https://doi.org/10.3389/fclim.2022.831587.

Garcia, et al. An experimental model approach of biologically-assisted silicate dissolution with olivine and *Escherichia coli*—Impact on chemical weathering of mafic rocks and atmospheric CO2 drawdown. Applied Geochemistry 31:216-227 (2013). DOI:10.1016/j.apgeochem.2013.01.007.

Gerrits, et al. How the rock-inhabiting fungus K. petricola A95 enhances olivine dissolution through attachment. Geochimica et Cosmochimica Acta 282:76-97 (2020). https://doi.org/10.1016/j.gca.2020.05.010.

Gerrits, R. An experimental study of fungal olivine weathering. Inaugural dissertation. Department of Biology, Chemistry and Pharmacy of the Freie Universität Berlin. 2019. doi: 10.17169/refubium-2880.

Golubev, et al. Experimental determination of the effect of dissolved CO2 on the dissolution kinetics of Mg and Ca silicates at 25 °C. Chem Geo 217(3):227-238 (2005). https://doi.org/10.1016/j.chemgeo.2004.12.011.

Guo, et al. Investigating the effect of nickel concentration on phytoplankton growth to assess potential side-effects of ocean alkalinity enhancement. Biogeosciences 19:3683-3697 (2022). https://doi.org/10.5194/bg-19-3683-2022.

Hallermeier, R.J. Sand Motion Initiation by Water Waves: Two Asymptotes. Journal of the Waterway, Port, Coastal and Ocean Division vol. 106, Issue 3 (Aug. 1980): pp. 299-318.

Hartmann, et al. Enhanced chemical weathering as a geoengineering strategy to reduce atmospheric carbon dioxide, supply nutrients, and mitigate ocean acidification. Reviews of Geophysics 51(2):113-149 (2013). https://doi.org/10.1002/rog.20004.

He, et al. Limits and CO2 equilibration of near-coast alkalinity enhancement. Biogeosciences 20:27-43 (2023). https://doi.org/10.5194/bg-20-27-2023.

Hisler, et al. Localized governance of carbon dioxide removal in Small Island Developing States. SSRN. 17 pages (May 25, 2022).

Hanchen, et al. Dissolution kinetics of fosteritic olivine at 90-150° C including effects of the presence of CO2. Geochimica et Cosmochimia Acta 70(17):4403-4416 (2006). DOI:10.1016/j.gca.2006.06.1560.

Hu, et al. An assessment of ocean margin anaerobic processes on oceanic alkalinity budget. Global Biogeochemical Cycles 25(3):11 pgs. (2011). https://doi.org/10.1029/2010GB003859.

Humphreys, et al. PyCO2SYS v1.8: Marine carbonate system calculations in Python. Geosci Model Dev 15(1): 15-43 (2022). DOI:10.5194/gmd-15-15-2022.

International search report with written opinion dated Jan. 20, 2023 for PCT/US2022/078319.

Kohler, et al. Geoengineering potential of artificially enhanced silicate weathering of olivine. PNAS 107(47):20228-20233. https://doi.org/10.1073/pnas.1000545107.

Köhler, et al. Geoengineering impact of open ocean dissolution of olivine on atmospheric CO2, surface ocean pH and marine biology. Environmental Research Letters. 8. (2013) 014009 (9pp) doi:10.1088/1748-9326/8/1/014009.

Lamerand, et al. Olivine dissolution and hydrous Mg carbonate and silicate precipitation in the presence of microbial consortium of photo-autotrophic and heterotrophic bacteria. Geochimica et Cosmochimica Acta. vol. 268. (2020) pp. 123-141. https://doi.org/10.1016/j.gca.2019.09.040.

Li, et al. A Review on Integrated Mineral Carbonation Process in Ultramafic Mine Deposit. Proceedings of the 8th Intl. Conf. on sustainable development in the minerals Industry; SDIMI. Geo-Resources Environment and Engineering (GREE) 2 (2017): 148-154. https://doi.org/10.15273/gree.2017.02.027.

Liu, et al. Mechanism for the dissolution of olivine series minerals in acidic solutions. Am Mineral 91(2-3):455-458 (2006). https://doi.org/10.2138/am.2006.2077.

Mccutcheon, J. Microbially induced magnesium carbonation reactions as a strategy for carbon sequestration in ultramafic mine tailings. Electronic Thesis and Dissertation Repository. 1306. Mas-

(56) References Cited

OTHER PUBLICATIONS ter of Science Thesis, The University of Western Ontario, published Jun. 13, 2013. https://ir.lib.uwo.ca/etd/1306.
Meysman, et al. Negative CO2 emissions via enhanced silicate weathering in coastal environments. Biology Letters 13(4):20160905 (2017). doi: 10.1098/rsbl.2016.0905.
Middelburg, et al. Ocean Alkalinity, Buffering and Biogeochemical Processes. Reviews of Geophysics 58.3 (2020): e2019RG000681. https://doi.org/10.1029/2019RG000681.
Millero, F.J. The marine inorganic carbon cycle. Chem Rev. Feb. 2007; 107(2):308-41. doi: 10.1021/cr0503557.
Montserrat, et al. Olivine Dissolution in Seawater: Implications for CO2 Sequestration through Enhanced Weathering in Coastal Environments. Environ Sci Technol 51(7):3960-3972 (2017). doi: 10.1021/acs.est.6b05942.
Moroz, et al. Space weathering of silicate regoliths with various FeO contents: New insights from laser irradiation experiments and theoretical spectral simulations. Icarus. vol. 235 (2014) pp. 187-206. https://doi.org/10.1016/j.icarus.2014.03.021.
Oelkers, et al. Olivine dissolution rates: A critical review. Chem Geo 500:1-19 (2018). https://doi.org/10.1016/j.chemgeo.2018.10.008.
Oelkers, et al. The efficient long-term inhibition of forsterite dissolution by common soil bacteria and fungi at Earth surface conditions. Geochim Cosmochim Acta 168:222-235 (2015). DOI:10.1016/j.gca.2015.06.004.
Olsen, et al. Oxalate-promoted forsterite dissolution at low pH. Geochim Cosmochim Acta 72(7):1758-1766 (2008). DOI:10.1016/j.gca.2007.12.026.
Power, et al. Accelerating mineral carbonation using carbonic anhydrase. Environmental Science & Technology 50.5 (2016): 2610-2618. https://doi.org/10.1021/acs.est.5b04779.
Power, et al. Serpentinite Carbonation for CO2 Sequestration. Elements. Apr. 1, 2013. vol. 9 (2): 115-121. doi: https://doi.org/10.2113/gselements.9.2.115.
Renforth, et al. Assessing ocean alkalinity for carbon sequestration. Reviews of Geophysics 55(3):636-674 (2017). https://doi.org/10.1002/2016RG000533.
Rigopoulos, et al. Carbon sequestration via enhanced weathering of peridotites and basalts in seawater. Appl Geochem 91:197-207 (2018). https://doi.org/10.1016/j.apgeochem.2017.11.001.
Rimstidt, et al. Systematic review of forsterite dissolution rate data. Geochim Cosmochim Acta 99:159-178 (2012). DOI:10.1016/j.gca.2012.09.019.
Ruiz-Agudo, et al. Mechanism of leached layer formation during chemical weathering of silicate minerals. Geology 40(10):947-950 (2012). DOI: 10.1130/G33339.1.
Saldi, et al. The role of Fe and redox conditions in olivine carbonation rates: An experimental study of the rate limiting reactions at 90 and 150 in open and closed systems. Geochim Cosmochim Acta 118:157-183 (2013). DOI:10.1016/j.gca.2013.04.029.
Shirokova, et al. Effect of the heterotrophic bacterium Pseudomonas reactans on olivine dissolution kinetics and implications for CO2 storage in basalts. Geochim Cosmochim Acta 80:30-50 (2012). DOI:10.1016/j.gca.2011.11.046.
Soulsby, et al. Threshold of sediment motion in coastal environments. In Pacific Coasts and Ports' 97: Proceedings of the 13th Australasian Coastal and Ocean Engineering Conference and the 6th Australasian Port and Harbour Conference; vol. 1, pp. 145-150. Christchurch, NZ: Centre for Advanced Engineering, University of Canterbury, 1997.
Soulsby, R. Dynamics of Marine Sands: A Manual for Practical Applications. London, England: Thomas Telford Publications. 1997. 249 pages. (Table of Contents).
Stockmann, et al. Do carbonate precipitates affect dissolution kinetics? 1: Basaltic glass. Chem Geol 284:306-316 (2011). DOI:10.1016/j.chemgeo.2011.03.010.
Stockmann, et al. Do carbonate precipitates affect dissolution kinetics ?: 2: Diopside. Chem Geol 337-338:56-66 (2013). DOI:10.1016/j.chemgeo.2012.11.014.
Sulpis, et al. RADIv1: a non-steady-state early diagenetic model for ocean sediments in Julia and MATLAB/GNU Octave. Geosci Model Dev 15:2105-2131 (2021). https://doi.org/10.5194/gmd-15-2105-2022.
Torres, et al. Microbial Acceleration of Olivine Dissolution via Siderophore Production. Procedia Earth and Planetary Science. vol. 10 (2014) pp. 118-122. https://doi.org/10.1016/j.proeps.2014.08.041.
Torres, et al. The kinetics of siderophore-mediated olivine dissolution. Geobiology 17(4):401-416 (2019). doi: 10.1111/gbi.12332.
Van Rijn, L.C. Principles of sediment transport in rivers, estuaries and coastal seas (vol. 1006, pp. 11-13). (1993) Amsterdam: Aqua publications.
Van Rijn, L.C. Unified view of sediment transport by currents and waves. I: Initiation of motion, bed roughness, and bed-load transport. Journal of Hydraulic engineering 133.6 (2007): 649- 667. DOI: 10.1061/ASCE 0733-9429(2007)133:6(649).
Walker, et al. A negative feedback mechanism for the long-term stabilization of Earth's surface temperature. Journal of Geophysical Research 86(C10):9776-9782 (Oct. 1981). https://doi.org/10.1029/JC086iC10p09776.
Walworth, et al. Mechanisms of increased Trichodesmium fitness under iron and phosphorus co-limitation in the present and future ocean. Nature Communications. vol. 7, Article No. 12081 (2016).
Wang, et al. Forsterite Dissolution in Saline Water at Elevated Temperature and High CO2 Pressure. Environ Sci Technol47(1):168-173 (2013). https://doi.org/10.1021/es301231n.
Wikipedia. Alteromonas. Wikipedia article accessed at https://en.wikipedia.org/w/index.php?title=Alteromonas&oldid=1008605610; Feb. 24, 2021 (Feb. 24, 2021).
Wikipedia. Thalassiosira. Wikipedia article accessed at https://en.wikipedia.org/w/index.php?title=Thalassiosira&oldid=1040967289; Aug. 27, 2021 (Aug. 27, 2021).
Wogelius, et al. Olivine dissolution at 25: Effects of pH, CO2, and organic acids. Geochim Cosmochim Acta 55(4):943-954. (1991). DOI:10.1016/0016-7037(91)90153-V.
Zeebe, et al. CO2 in Seawater: Equilibrium, Kinetics, Isotopes. Elsevier Oceanography Series 1st Edition. 360 pgs. (Oct. 2001). (Table of Contents).
International search report with written opinion dated Feb. 8, 2023 for PCT/US2022/078323.
Purakayastha, et al. Biochar carbon sequestration in soil-A myth or reality ?. International Journal of Bio-resource and Stress Management 6.5 (2015): 623-630.
Gerrits, et al. High-resolution imaging of fungal biofilm-induced olivine weathering. Chemical Geology. vol. 559 (2021) 119902. doi:10.1016/J.CHEMGEO.2020.119902.

* cited by examiner

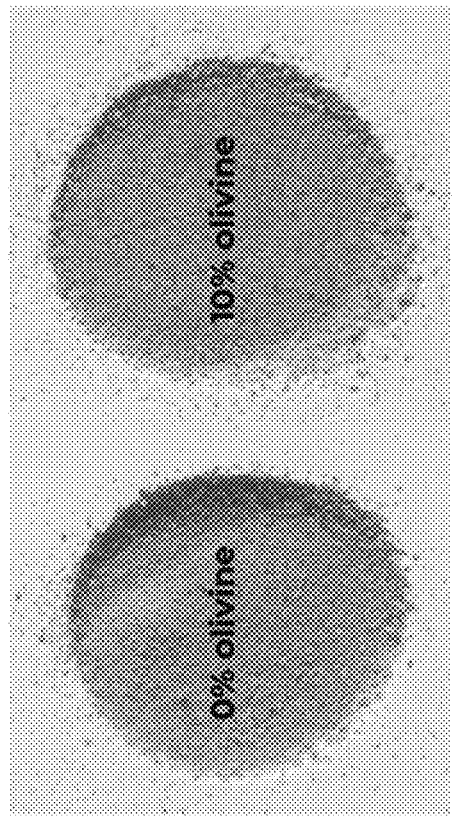
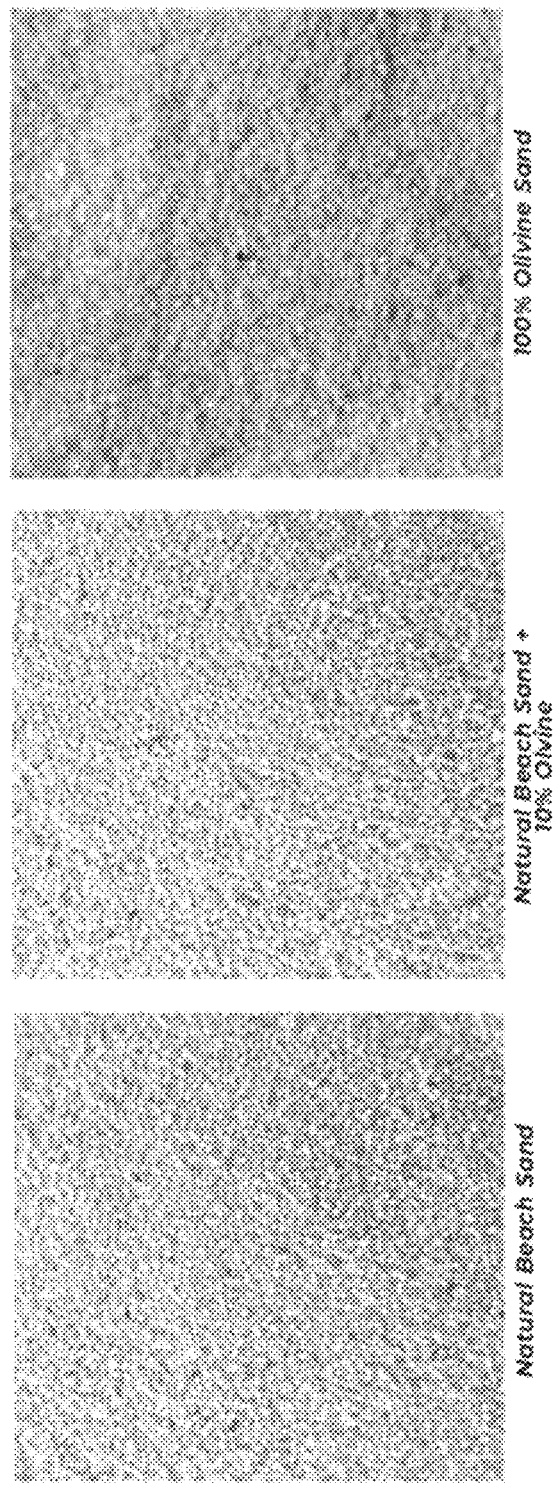
FIG. 4

Spatial and Temporal Heterogeneity

Coastal ecosystems are extremely dynamic in time and space.

Temporal Factors
1) Diurnal (Day/Night Variation)
2) Tides
3) Seasonality
4) Temperature
5) Weather
6) Waves

Spatial Factors
1) Position/Hydrodynamics
2) Depth
3) Tides
4) Sediment Type
5) Grain Size
6) Sediment Organic Carbon Content
7) Bottom cover (sea grass, rocks, coral, etc)

*FIG. 28*

Summary of 4 MRV Approaches at Different Scales of Cost & Complexity

| Approach | Cost & Effort | Description |
|---|---|---|
| 1 | ~ free | Shrinking Core Model |
| 2 | $$ | #1 + Mesocosms/Sediment Tracing/Simple Modeling |
| 3 | $$$ | #2 + Limited In-situ Flux Measurements |
| 4 | $$$$ | #3 + Extensive Modeling, Full Spatial-temporal Model |

*FIG. 33*

Numerical simulation of alkalinity profile generated by a 2 cm thick layer of olivine sand spread over beach sand Sensor Development
o An automated way to measure:
  o Temp
  o Salinity
  o pH
  o $pCO_2$
  o DIC
  o Alkalinity
  o Wave Impacts on Sand
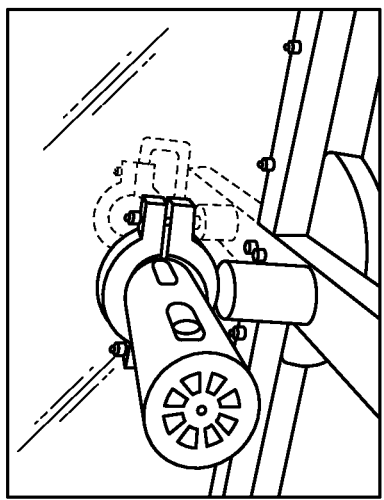
Exo Sonde (Temp, Salinity, Pressure, pH)
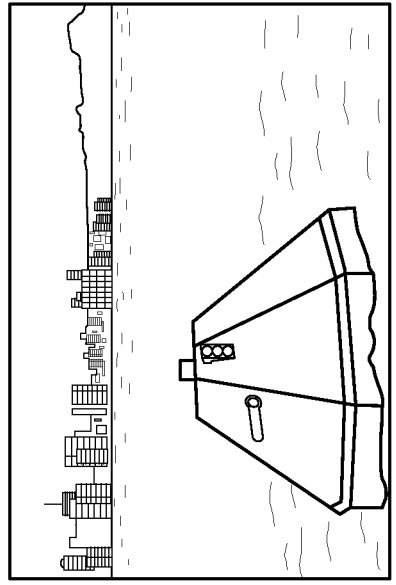
MAPCO2 Buoy (CO2 Flux)
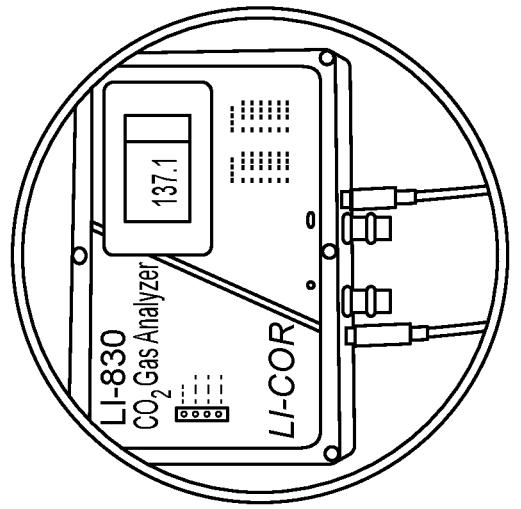
Li-Cor LI-830 $CO_2$ Gas Analyzer
FIG. 35

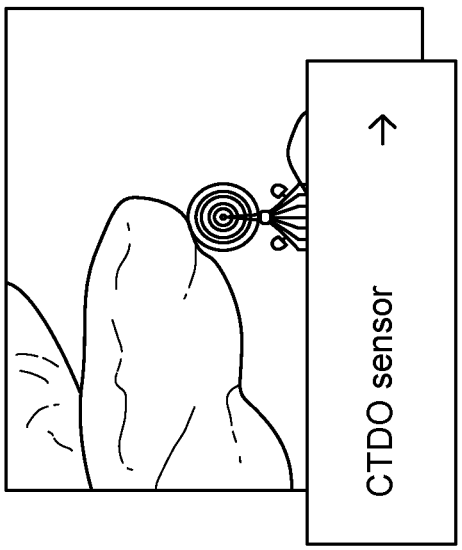 CTDO sensor
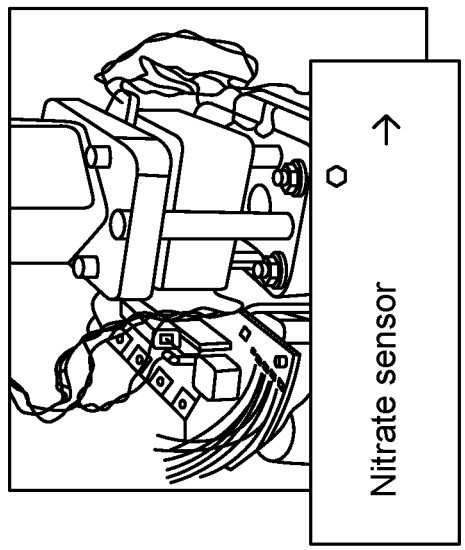 Nitrate sensor
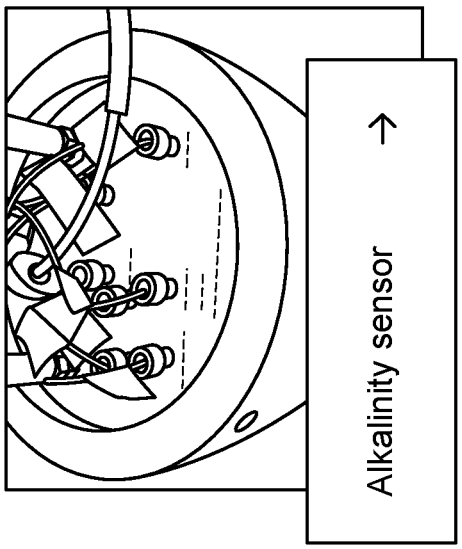 Alkalinity sensor
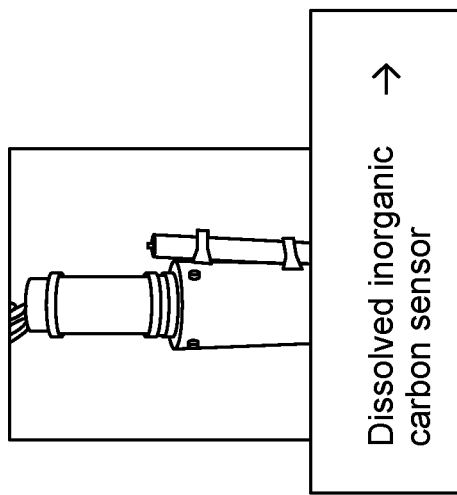 Dissolved inorganic carbon sensor
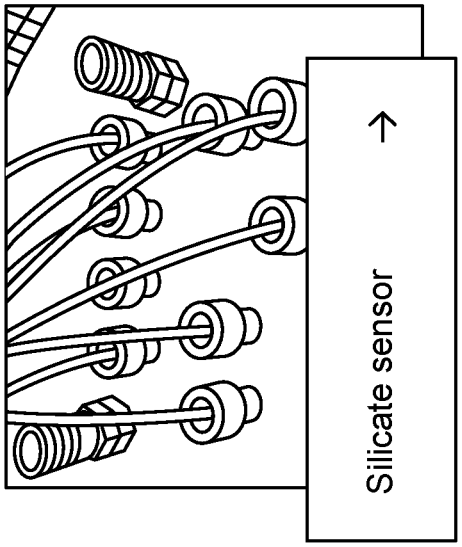 Silicate sensor
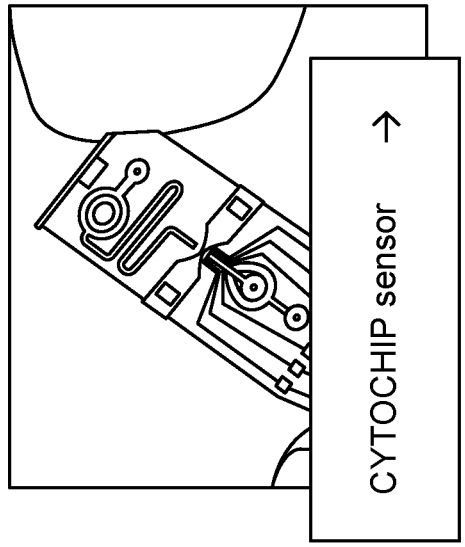 CYTOCHIP sensor
FIG. 36

- Seawater carbonate chemistry is controlled by four terms (pCO2, pH, DIC, Alkalinity). There are two degrees of freedom, so if you control fix any two parameters, you control the rest.

- We want to express how water DIC storage changes as a function of increasing ALK.

- Oceanographers refer to this as the isocapnic quotient (Q)

- $Q = \frac{\partial ALK}{\partial DIC}$  (at fixed pCO2, Temp, Sal)

- 1 μmol ALK increase → 0.78-0.93 μmol DIC increase

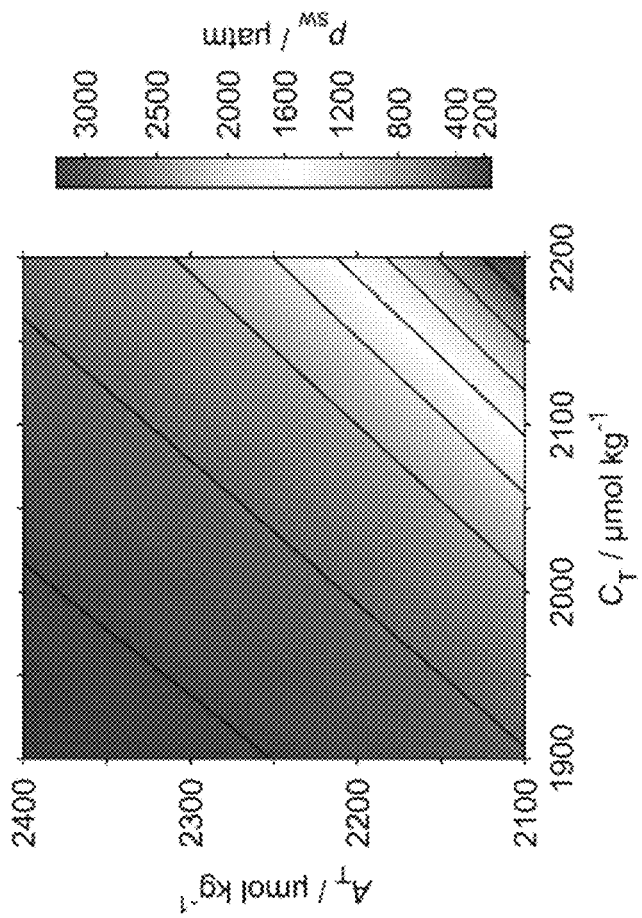

FIG. 39

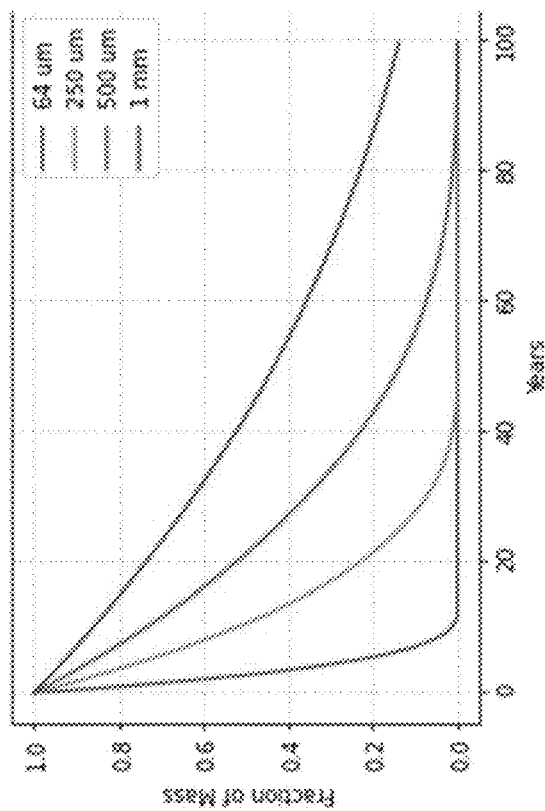
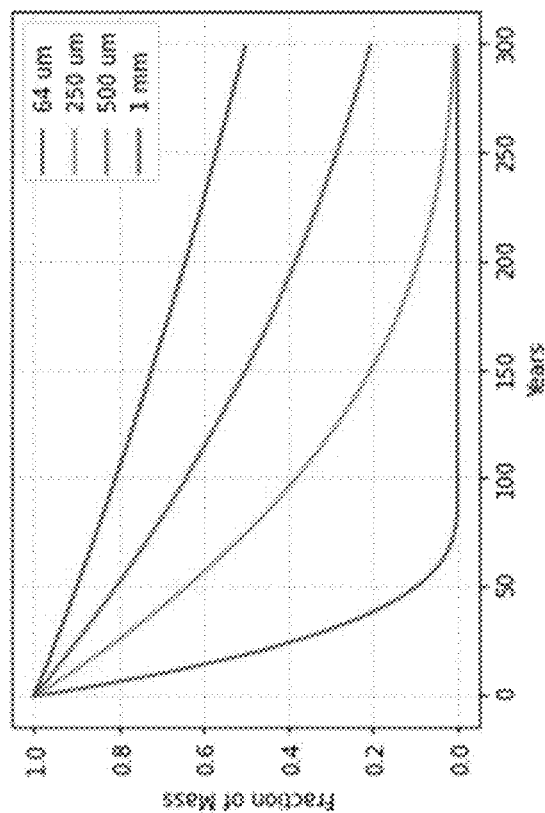
FIG. 43

$Mg_2SiO_4 + 2 CO_2 + 2 H_2O + 2 Ca^{2+} \rightarrow 2 Mg^{2+} + 2 CaCO_3 + H_4SiO_4$ 1 Olivine + 2 Carbon Dioxide + 2 Water + 2 Calcium Ions -> 2 Magnesium Ions + 2 Limestone + 1 Silicic Acid $3 Mg_2SiO_4 + 8 CO_2 + 7.5 H_2O \rightarrow$
$0.5 Mg_4Si_6O_{15}(OH)_2 \cdot 6H_2O + 4 Mg^{2+} + 8 HCO_3^-$ Conversion of Olivine to Sepiolite

CARBON-REMOVING SAND AND METHOD AND PROCESS FOR DESIGN, MANUFACTURE, AND UTILIZATION OF THE SAME

CROSS REFERENCE TO RELATED APPLICATIONS

This application is a continuation of International Patent Application PCT/US22/78323, filed Oct. 18, 2022, which claims the benefit of U.S. Provisional Application No. 63/256,986, filed Oct. 18, 2021, U.S. Provisional Application No. 63/281,575, filed Nov. 19, 2021, U.S. Provisional Application No. 63/298,412, filed Jan. 11, 2022, U.S. Provisional Application No. 63/403,446, filed Sep. 2, 2022, U.S. Provisional Application No. 63/377,171, filed Sep. 26, 2022, and European Patent Application No. 22157366.0 filed Feb. 17, 2022, each of which is incorporated herein by reference in its entirety.

BACKGROUND

Carbon dioxide is a powerful greenhouse gas, currently comprising 0.0415% (415 parts per million) of the Earth's atmosphere. Current anthropogenic emissions of carbon dioxide greatly exceed all available natural and manmade sinks, leading to persistent, long-term increases in the atmospheric concentration of carbon dioxide. The increase in atmospheric carbon dioxide concentration results in multiple deleterious effects on the natural environment, including rising global mean temperature, rising sea level, acidification of seawater, and changes in annual weather patterns, collectively known as climate change. There exists a need for systems, methods, compositions and processes to effect capture and sequestration of atmospheric carbon dioxide.

In many coastal regions, climate change manifests itself through increased rates of coastal erosion, rising sea levels, increased frequency and magnitude of storms and flood events, and nuisance flooding. These impacts have led to a growing demand for environmental management of bodies of water (e.g., shelf seas, coastlines, marshes and other wetlands, lakes, rivers, estuaries, bays, etc.), including beach nourishment, erosion control, storm defenses, coastal protection, climate mitigation (including carbon removal), and other coastal engineering or coastal geology products or placements of coastal devices such as sand (all of which together we refer to herein generally as "coastal construction projects"), most of which typically require large amounts of sand, gravel, and other compositions of natural materials to be mined or dredged from surrounding regions and placed in coastal environments to act as barriers or increase the volume of sediment in a system.

The materials and substrates used for coastal construction projects must meet strict requirements regarding, among other characteristics: grain size, color, density, and fluid transport properties. Naturally occurring deposits of suitable materials are in short supply in many coastal regions where erosion and sea level rise threaten to outstrip the capacity to deliver new materials to the coastal system. Prior attempts have sought to mitigate the demand for native sand in coastal construction by using non-native materials, including, for example, recycled and crushed glass, though these materials were generally found to have textures and properties unsuitable to replace native beach sand.

SUMMARY

The present invention generally relates to systems, methods, compositions, and processes for designing, manufacturing, and utilizing carbon-dioxide—sequestering substrates which can fully or partially replace natural sand in coastal construction applications described herein, while effecting capture and sequestration of atmospheric carbon dioxide. FIG. 49 provides the graphical representation of these systems, methods, and processes. The systems, methods, compositions, and processes as provided herein may meet one or more needs as described herein. For instance, given the large volume of sediment used in coastal construction projects, the increasing scarcity of local stockpiles of suitable materials, and the lack of suitable alternatives, it would be desirable to have a readily available engineered material which could be tailored to meet exacting coastal construction specifications, especially if such engineered material were also capable of removing excess carbon dioxide from the atmosphere and the ocean, thereby also addressing the root cause of increased levels of coastal erosion, sea level rise, and frequency and magnitude of storms and flood events. Furthermore, there exists a need to identify the appropriate properties (grain size, color, density, hydraulic transport, etc.) of a suitably engineered material, and develop methods and processes for the design, manufacture, utilization, or monitoring of the engineered material in real-world, coastal-construction applications.

Certain naturally occurring geological minerals (e.g. olivine) as well as manmade industrial byproducts (e.g. slag) may chemically interact with carbon dioxide to effect the consumption of protons and the conversion of gaseous carbon dioxide into either aqueous dissolved bicarbonate and carbonate ions ($HCO_3^-$ and $CO_3^{2+}$) or solid-phase carbonate mineral species ($CaCO_{3(s)}$ and $MgCO_{3(s)}$), both of which act to remove carbon dioxide from the atmosphere (a process known as "Carbon Dioxide Sequestration"). Grinding these minerals to smaller particle sizes may increase the available surface area of such mineral particles, thereby enhancing the rate at which they are able to sequester carbon dioxide from the atmosphere (a process known as "Enhanced Weathering").

To address the needs described above, the present disclosure provides a novel engineered material ("carbon-removing sand") along with general methods and processes for: (1) optimizing the composition of the carbon-removing sand to control its engineered properties, such as carbon dioxide removal potential, color, density, and hydraulic transport, (2) manufacture and placement of carbon-removing sand blends in coastal construction projects, and (3) monitoring the physical transport and chemistry of carbon-removing sand to verify the physical and chemical performance of the engineered material. Although the term "sand" in certain contexts is used to refer to a material with a grain size between 63 microns and 2,000 microns (i.e., in the Wentworth Classification), the term "sand" as used herein as part of "carbon-removing sand" and "non-carbon-removing sand" also encapsulates other sediment or grain sizes defined as gravel, silt and mud (i.e., also in the Wentworth Classification). In an aspect, the present disclosure is directed to an engineered material "carbon-removing sand", and novel methods to select, prepare, blend, transport, distribute, and monitor this material for use in coastal construction projects, including, without limitation, for the purpose of mitigation of coastal erosion, climate change, and/or ocean acidification. Carbon-removing sand may comprise specially selected, prepared, and blended mineral particles which [1] are suitable for use in coastal construction projects (e.g., to mitigate coastal erosion along coasts), and [2] interact with carbon dioxide ($CO_2$) and/or dissolved carbonic acid [$H_2CO_3$] to produce bicarbonate [$HCO_3^-$], [$CO_3^{2-}$] ions, and/or solid-phase carbonate minerals [Ca, Mg]CO$_3$, thus [3] simultaneously mitigating the impacts of climate change, ocean acidification, and coastal erosion.

To be suitable for use in coastal construction projects, carbon-removing sand must meet various criteria regarding grain size distribution, fines and coarse content, elemental composition, color, density and hydrodynamic transport properties. These requirements are necessary in order to (1) comply with applicable legal requirements, (2) meet objectives of the applicable coastal construction project regarding stability, erodibility, and transport of sediment substrates (3) and meet aesthetic and environmental protection criteria for sand color and texture.

In another aspect, the present disclosure provides a method to control the grain-size distribution, fines and coarse content, elemental composition, color, density, and hydrodynamic properties of carbon-removing sand to achieve the required specifications for use in coastal construction projects. In some embodiments, these properties may be controlled by incorporating one or more sediment components as a blended substrate, which may optionally consist of different materials, mineralogy, grain size distribution, colors, densities, etc.

To efficiently remove carbon dioxide from the atmosphere, at least one component of the carbon-removing sand may be manufactured from an alkaline material. Not limiting examples may include naturally occurring olivine, dunite, basalt, serpentinite, serpentine, brucite, wollastonite, or industrial-produced mineral-equivalents such as slag or mine tailings. These minerals interact with water and carbon dioxide and/or carbonic acid to produce bicarbonate ion as a product, thereby decreasing the acidity of the surrounding fluid and converting the harmful carbon dioxide or carbonic acid into environmentally beneficial bicarbonate or carbonate ion or solid carbonate precipitate as a byproduct. This reaction typically occurs on decadal to centennial timescales, thereby rendering it sufficient for climate mitigation and effectively inert on the instantaneous environment. An example describing the interaction of forsterite olivine (Mg$_2$SiO$_4$) with carbon dioxide (CO$_2$) dissolved in seawater is provided below, although other minerals and rocks described in this disclosure may result in equivalent reactions converting dissolved carbon dioxide and water (carbonic acid) to bicarbonate ion:

(a) Mg$_2$SiO$_4$+4 CO$_2$+4 H$_2$O→2 Mg$^{2+}$+4 HCO$_3^-$+H$_4$SiO$_4$
(b) Through the conversion of carbon dioxide to dissolved bicarbonate and carbonate ions, this reaction acts to reduce the partial pressure of carbon dioxide in seawater. In coastal construction projects, this seawater is in close contact with the surface ocean and atmosphere, allowing net transfer of carbon dioxide across the air-sea interface, thereby effecting the net sequestration of atmospheric carbon dioxide as bicarbonate and carbonate ion in seawater.

In some embodiments, a composition comprising the carbon-removing component of carbon-removing sand may further comprise one or more non-carbon removing components. These components may include, but are not limited to, native sand and sediment, dredged materials, upland sand, silicate sand (e.g., quartz and/or feldspar sand), carbonate sand, etc. The role of the materials may be to control the overall grain-size distribution, fines and coarse content, elemental composition, color, density, and hydrodynamic properties of the final blended product to meet project specifications.

In order to simultaneously achieve the requirements of sand and sediment for coastal construction projects, while preserving such material's ability to sequester carbon dioxide as described above, it may be necessary, in some embodiments of the invention, to specially prepare the carbon-removing mineral components and then blend these components in a specifically determined ratios with non-carbon-removing sand such as native or allochthonous sand and sediment to achieve the desired chemical, engineering, and aesthetic properties.

In still another aspect, the processes for preparing carbon-removing sand must be tailored such that the carbon-removing sand and blends thereof achieve specific pre-determined properties unique to regional or local requirements.

In another aspect, the carbon-removing material may be further modified via mixing non-carbon-removing sediment in order to achieve a combination of texture, color, and density, and engineering properties suitable for use in coastal construction projects.

In another aspect, feedstock materials of carbon-removing materials and, in some cases, non-carbon removing materials, may be crushed and/or milled (including via high pressure grinding rolls) to increase weatherable surface area, create microcracks for increased weathering, or achieve desired grain-size requirements.

In another aspect, crushed and/or milled material may be size sorted using methods including but not limited to sieves, gravity separation, or air classifiers to, among other things, provide a final product with a mean grain size and overall grain size distribution which meets the specifications of the applicable coastal construction project. This process is designed to constrain fine-grained material and/or coarser particles to produce a grain size material which is compatible with the size distribution of the native sediment in the location receiving the carbon-removing sand or is otherwise appropriate for the dual conditions of a coastal construction project and carbon dioxide removal.

In another aspect, the carbon-removing and/or non-carbon-removing material may be pre-sorted into various pre-determined size ranges. Preferred sizes may be selected and/or blended from these pre-classified separates to achieve an overall blend suitable for use in a specific coastal construction project.

In another aspect of the invention, a sediment transport model and a geochemical reaction-transport model, used in tandem or apart, may be used to optimize the design of the carbon-removing sand mixture. This may include, but is not limited to, consideration of material composition, grain size, texture, porosity, permeability, crystalline structure, density, transport potential, environmental impact, and carbon dioxide removal potential. Any description herein of a sediment transport model may also apply to a hydrodynamic model. A model described herein may incorporate fluid (e.g., water) motion, and/or how carbon-removing and/or non-carbon removing materials, such as olivine and/or sand are moving within the fluid.

In an embodiment, the reaction-transport model and sediment transport model may be used in tandem or apart to optimize the placement design of the carbon-removing sand mixture for optimal carbon dioxide removal potential, environmental impact, and coastal construction or other engineering outcomes. This may include, but is not limited to, consideration of the relative homogenous or heterogenous placement of sand mixture components.

In another aspect of the invention, a reaction-transport model and sediment transport model may be used in tandem or apart to achieve the optimal placement and location. This may include, but is not limited to, consideration of riverine, estuarine, lacustrine, marsh, wetland, beach, shore face, near shore, or shelf locations.

As a result, this process has the potential co-benefit of serving as a sediment transport and/or hydrodynamic tracer in coastal construction projects. For example, utilizing the color, albedo, chemistry, density, grain size, etc. of the carbon-removing sand component as a unique indicator of overall project sediment transport, project success, or other metrics.

In another aspect, to realize a blended mixture between the carbon-removing and non-carbon-removing components of the mixture, the individual components may either be brought together in advance, or in alternate embodiment, be separately conveyed or placed onto the project site in such a manner to realize an appropriate mixture over the duration of the project (i.e. mixing between components occurs via the physical motion of sediment driven by conveyors, heavy equipment, bioturbation and/or waves, currents and tides).

In another aspect, a sediment transport model may be used to determine the method of combining the sediment components. This may include, but is not limited to, consideration of placement location along the cross-shore or long-shore profile, the sediment properties, and the way it is distributed.

In another aspect, carbon-removing sand may be transported by land or water to the deployment site. There it may be distributed using a spreading device of either hydraulic or mechanical in nature, including such techniques as placement by truck, deck barge, dredge scow, hopper dredge, split-hull barge, rainbowing via modifications to dredging procedures, direct offloading from dry bulk ship and more, necessary to achieve the placement design.

In another aspect, placements may be conducted in a single monolithic deployment location or in discontinuous segments that comprise a project location.

In another aspect, a sediment transport model may be used to guide the placement distribution logistics.

Another aspect of the invention relates to processes and methods for quantifying the rate and extent to which carbon-removing sand sequesters carbon dioxide. These methods may include determination of the concentration, flux, or isotopic composition of chemical species resulting from the dissolution of carbon-removing sand. These methods may also include determination of the impact of carbon-removing sand upon the ambient concentration, flux, or isotopic composition of gaseous or aqueous carbon dioxide species and alkalinity found in the region surrounding carbon-removing sand.

In another aspect, these methods may optionally include the introduction of a chemical or isotopic tracer which serves to facilitate the determination of the rate or extent at which carbon-removing sand undergoes chemical dissolution or transformation.

In another aspect, these methods may be conducted at a single point in time or as part of a time series.

In one embodiment, these determinations are made in the pore fluid in contact with the carbon-removing sand as well as the overlying water. In other embodiments, these determinations may be made via the installation of a chamber installed upon the sediment surface which acts to integrate the accumulation of reaction products and/or the depletion of chemical reactants across the sediment-water interface.

In still other embodiments, these methods may include determining the flux of aqueous or gaseous carbon dioxide in the overlying air or water by means of eddy covariance techniques.

In still further embodiments, these methods may include determination of the rate of dissolution or chemical transformation of the carbon-removing sand material via quantification of the abundance of the initial and subsequent mineral phases present in sediments.

While all the above methods may be conducted in situ, in still other embodiments any or all of the above methods may be conducted ex-situ via the construction of a reactor apparatus which serves to emulate the behavior of carbon-removing sand in the environment. Such reactors may be conducted at a range of sizes and scales including but not limited to laboratory "bench-scale" reactors, batch-scale reactors, larger outdoor mesocosm scale reactors or other reactors designed to replicate desired real-world conditions in certain embodiments. Such reactors may optionally be constructed in such a manner to make them portable facilitating transportation between sites.

In some embodiments of the invention, determination of the rate at which carbon-removing sand undergoes reaction may be facilitated, predicted, or summarized via the construction of a mathematical computer model. Such a model may accept certain environmental, biological parameters and/or physical properties of the carbon-removing sand and/or the results of the aforementioned chemical or physical determinations to output either the dissolution rate of carbon-removing sand and/or the physical and chemical impact of carbon-removing sand on the surrounding environment.

In some embodiments of the invention, determination of the rate at which carbon-removing sand removes carbon dioxide from the atmosphere across spatiotemporal scales may be facilitated, predicated, or summarized via the construction of mathematical computer models. Such models may accept certain environmental parameters and/or physical properties of the carbon-removing sand, the results of the aforementioned mathematical computer models and/or the results of the aforementioned chemical or physical determinations to output either the atmospheric carbon capture derived from the carbon-removing sand and/or the physical and chemical impact of carbon-removing sand on the surrounding environment, in both cases across space and time.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4 schematically illustrates olivine and mixtures of sand and olivine, in accordance with some embodiments.

FIG. 28 schematically illustrates examples of temporal factors and spatial factors that can vary for coastal ecosystems, in accordance with some embodiments.

FIG. 33 shows a summary of various approaches for measuring, recording, and verifying carbon capture and olivine dissolution at different scales of cost and complexity, in accordance with some embodiments.

FIGS. 35-36 schematically illustrate various examples of sensors that can be used for measuring, recording, and verifying carbon capture and/or olivine dissolution, in accordance with some embodiments.

FIG. 39 schematically illustrates an approach to calculating CO2 sequestration from alkalinity flux based on an expression of how water DIC storage changes as a function of increasing alkalinity, in accordance with some embodiments.

FIG. 43 schematically illustrates various plots showing exemplary olivine dissolution kinetics for olivine particles having different grain sizes, in accordance with some embodiments.

DETAILED DESCRIPTION

Figure 1:
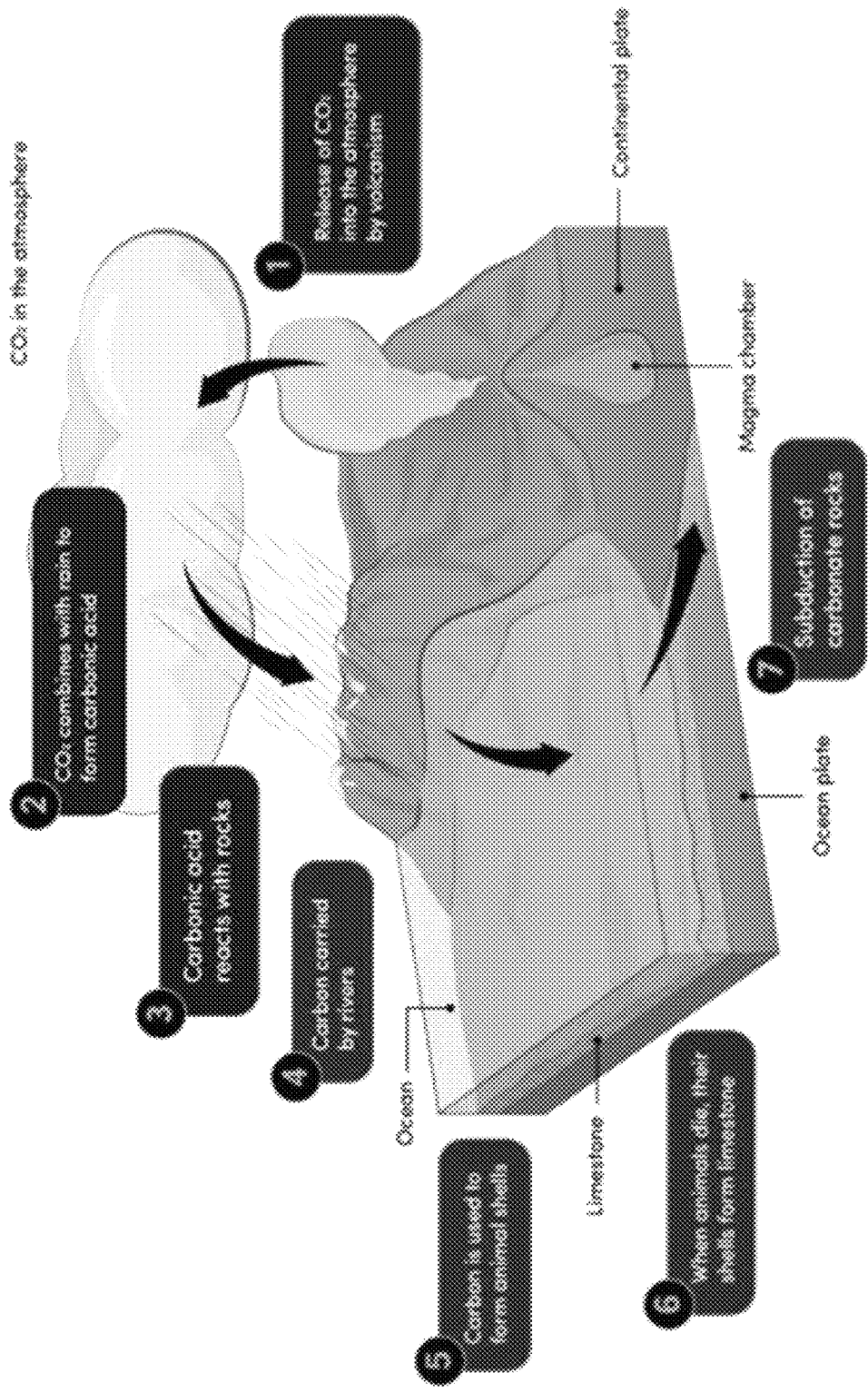
FIG. 1 schematically illustrates the long-term carbonate-silicate cycle, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

Overview

To avoid the worst effects of climate change, we must rapidly remove billions of tons of carbon dioxide from the atmosphere. There is an urgent need to identify carbon removal methods which are permanent, scalable, and economical. To combat climate change and mitigate its deleterious effects in coastal environments there is an urgent need for materials which can be used to both physically protect and remediate areas, combat increasing carbon dioxide levels, and reduce the impact of ocean acidification. These methods must likewise be permanent, scalable, and economical.

The earth's long-term carbonate-silicate cycle is how our planet has naturally captured carbon dioxide from the atmosphere. Over millennia, rain falling on exposed igneous rock causes such rocks to slowly dissolve in a process known as "weathering." Carbonic acid dissolved in the rainwater reacts with silicate from such rocks, generating alkalinity and shifting equilibrium from carbonic acid to bicarbonate. This water eventually flows to the oceans, which ultimately causes the ocean to absorb carbon dioxide from the atmosphere as bicarbonate dissolved in ocean water. Bicarbonate has a long ocean residence time, significantly longer than human timescales, with any subsequent biotic or abiotic precipitation of carbonate minerals resulting from increased bicarbonate causing the formation of carbonate rock.

"Ocean Alkalinity Enhancement" refers to the class of negative carbon dioxide emissions technologies (NETs) which seek to remove atmospheric carbon dioxide and store it on long timescales (tens to hundreds of thousands of years) through the acceleration of this natural weathering process.

"Coastal Carbon Capture," one real-world implementation of the theoretical "Coastal Enhanced Weathering," (and which may be referred to by the mark Coast Carbon Capture) can be categorized as a negative emission technology (NET) within the field of Ocean Alkalinity Enhancement which removes atmospheric carbon dioxide and stores it on long timescales (tens to hundreds of thousands of years) by spreading engineered carbon-removing sand in coastal systems, where such engineered material can dissolve in seawater more quickly than in natural conditions, thereby increasing the rate of carbon dioxide absorption by the ocean.

FIG. 1 illustrates the long-term carbonate-silicate cycle. Natural carbon dioxide removal through rock weathering may be achieved through the following steps:
1. Rain falls on igneous rocks, slowly dissolving them.
2. Carbonic acid dissolved in the rainwater reacts with silicate from such rocks, generating alkalinity and shifting the equilibrium from carbonic acid to bicarbonate.
3. This bicarbonate flows to the ocean.
4. The bicarbonate combines with calcium and magnesium ions to form carbonate.
5. Carbonate is deposited on the seafloor, thereby capturing atmospheric carbon dioxide in rock.

Figure 2:
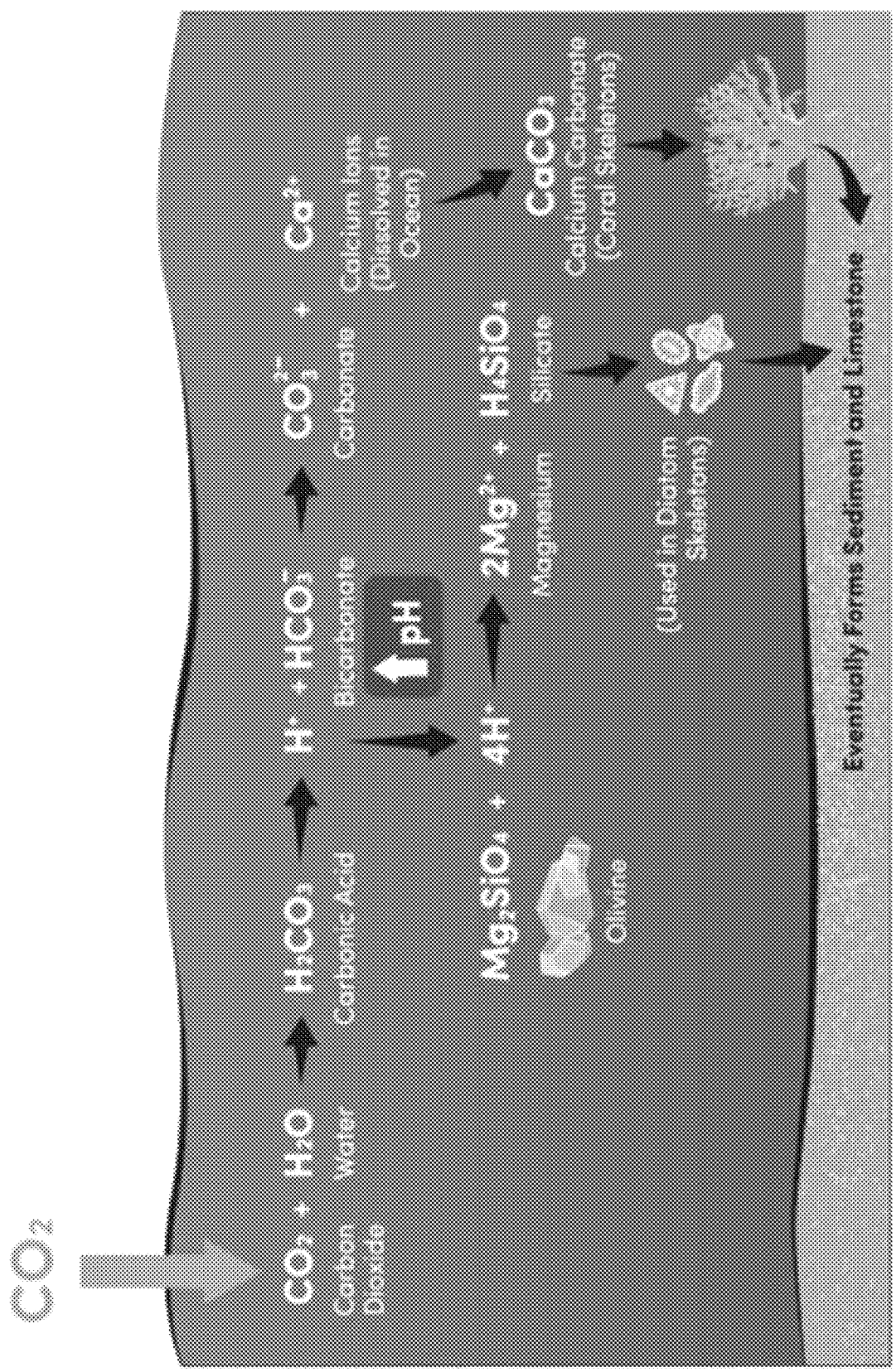
FIG. 2 schematically illustrates the chemical process by which olivine can be used to capture and sequester carbon dioxide, in accordance with some embodiments.

FIG. 2 illustrates the chemical processes which occurs as part of the long-term carbonate-silicate cycle involving mafic or ultramafic materials resulting in carbon dioxide capture and sequestration, i.e. the conversion of dissolved carbon dioxide and water to bicarbonate via olivine, which thereby allows uptake of atmospheric carbon dioxide into the surface ocean and seawater pH increase.

Figure 3:
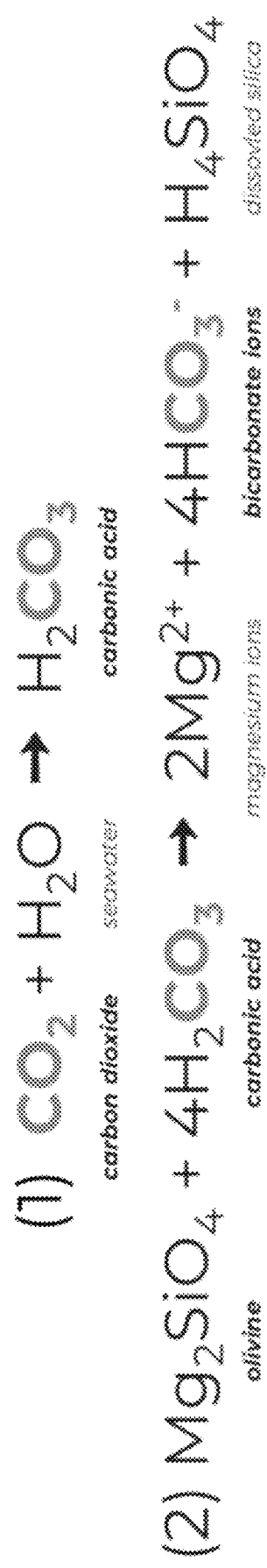
FIG. 3 schematically illustrates the chemical reactions that enable carbon dioxide capture and sequestration using olivine, in accordance with some embodiments.

FIG. 3 illustrates the chemical process that enables carbon dioxide capture and sequestration using olivine. As the olivine dissolves, its products are magnesium ions (the second most abundant ion in the ocean behind sodium), silicate (used by diatoms to build their skeletons) and dissolved carbon. Referring to FIG. 2 and FIG. 3, when olivine dissolves in water, it drives the illustrated reaction, thus increasing carbon dioxide uptake, raising pH, and generating alkalinity.

As a result, this process has the potential co-benefit of counteracting ocean acidification. Ocean acidification is the process by which increasing atmospheric carbon dioxide dissolves in seawater, which reduces pH (increasing acidity) (upper reaction in diagram below). This reduces the ability of calcifying organisms like corals to grow and produce exoskeletons, or shells. As shown in FIG. 2 and FIG. 3, dissolving alkaline material (e.g., olivine) in water sequesters hydrogen ions into dissolved silicate ($H_4SiO_4$), a molecule that can be used by diatoms—important photosynthesizing algae that fix carbon dioxide and form the base of the marine food web.

Unfortunately, natural chemical weathering happens too slowly to correct for human carbon dioxide emissions on human-relevant timescales. This natural process is also already accounted for in Earth's present-day carbon budget. The systems and methods disclosed herein can be deployed and implemented to accelerate this natural process to remove at least one additional gigaton of atmospheric carbon dioxide per year on a global scale.

Method of Removing Atmospheric Carbon

Coastal Carbon Capture with carbon-removing sand can be used to accelerate Earth's natural carbon dioxide removal process. At current rates, the natural process of rock weathering through rainfall needs to be sped up by at least 100 times to absorb the carbon dioxide emitted by human activity. Wave energy can accelerate Coastal Carbon Capture. The rock containing the olivine may be placed in high-energy coastal environments, where wave energy mechanically weathers the rock. As sediment grains collide, this mechanical process speeds up the chemical dissolution of the material. This rate is orders of magnitude faster than if the material were left to weather naturally where it was originally deposited.

In an aspect, the present disclosure provides methods of design and production of carbon-removing sand blend for dispersal. The selection of carbon-removing sand may be mafic, ultramafic, or an industrial byproduct in nature (see Table 1). As used herein, such materials are referred to as "alkaline materials" and may refer to one or more entries of Table 1. The material may be mixed with non-carbon-removing sand material, such as quartz, carbonate, dredge material or native sediment (see Table 2) to generate a blend. The optimal grain size of the material will be selected. In some cases, selection may involve use of a sediment transport model or formula, a geochemical model, a regional ocean model system (ROMS) and or an earth system model. In some cases, selection may involve use of a life cycle analysis. Such models are not limited to, but may utilize one or more of the following parameters: grid resolution, topo-bathymetry, sediment density, sediment size distribution, sediment composition, spatial variability in sediment characteristics, including size and composition, distribution, vertical (layers number, thickness) and horizontal, wave conditions, tides, currents, wind conditions, viscosity, diffusivity, roughness, mineralogy, chemical composition, pH, temperature, salinity, alkalinity, partial pressure of carbon dioxide (pCO2), dissolved inorganic carbon (DIC) content, dissolved organic carbon content, particulate organic carbon content, particulate inorganic carbon content, trace metal content, major cation and anion content, nutrient content, dissolved oxygen, redox, methane concentration, nitrous oxide concentration, irrigation, bioturbation, advection, diffusion, microbial community composition, carbon dioxide emissions, carbon dioxide-equivalent emissions, energy, power, distance, cost, etc. In some cases, olivine may be the selected material. Olivine is a silicate mineral found in ultramafic and mafic rocks. It is highly abundant and found near the surface all over the world. Olivine rocks can be efficiently crushed to silt, sand, and gravel grain sizes.

In an aspect, the present disclosure provides details on the extraction and grinding of carbon-removing sand and blend constituents. Once a carbon-removing sand has been selected for dispersal for a particular location, the constituent minerals for such carbon-removing sand are extracted (generally through quarrying rock containing such minerals) and milled or grinded into the appropriate grain size of use in the target site of the applicable coastal engineering project. In some cases, a non-carbon-removing sand constituent may be required and may also be extracted (generally through quarrying rock containing such minerals) and milled or grinded into the appropriate grain size of use in the target site of the applicable coastal construction project. In yet other instances, a non-carbon-removing sand constituent may be comprised of dredge material and may require extraction from the seafloor or other coastal, riverine, or similar environment. In yet other instances, a non-carbon-removing sand constituent may be comprised of native sediment and may not require extraction or manipulation.

To realize a blended mixture between the carbon-removing and non-carbon-removing components, the individual components may either be brought together in advance, or in alternate embodiments, separately conveyed or placed onto the project site in such a manner to realize an appropriate mixture over the duration of the project (ie. mixing between components occurs via the physical motion of sediment driven by conveyors, heavy equipment, bioturbation, and/or waves, tides and currents).

(c)

Coastal Carbon Capture with carbon-removing sand may comprise the following steps:

1. Identification of deployment site. This will include consideration of and not be limited to the following factors: climate, wave conditions, tides, currents, dominant sediment transport mechanisms, accessibility by land and sea, native sediment size distribution and composition, local ecology, and social license. In some cases, this process will leverage a sediment transport model incorporating some or all of the parameters set forth above as well as some or all of the following parameters: wave activity, tides, currents, wind, coastal sedimentology and composition, and weather. In yet other instances, this process will leverage a geochemical model incorporating some of, all, but not limited to, the following parameters: mineralogy, density, seawater chemistry, bioturbation, irrigation, sediment composition. In yet other instances, the process will leverage a regional ocean model system and/or an earth system model incorporating some of, all, but not limited to the following parameters: seawater circulation, seawater residence time, ocean biogeochemistry, seawater carbonate saturation states, wind speed, fetch, and atmospheric composition.

Figure 46:
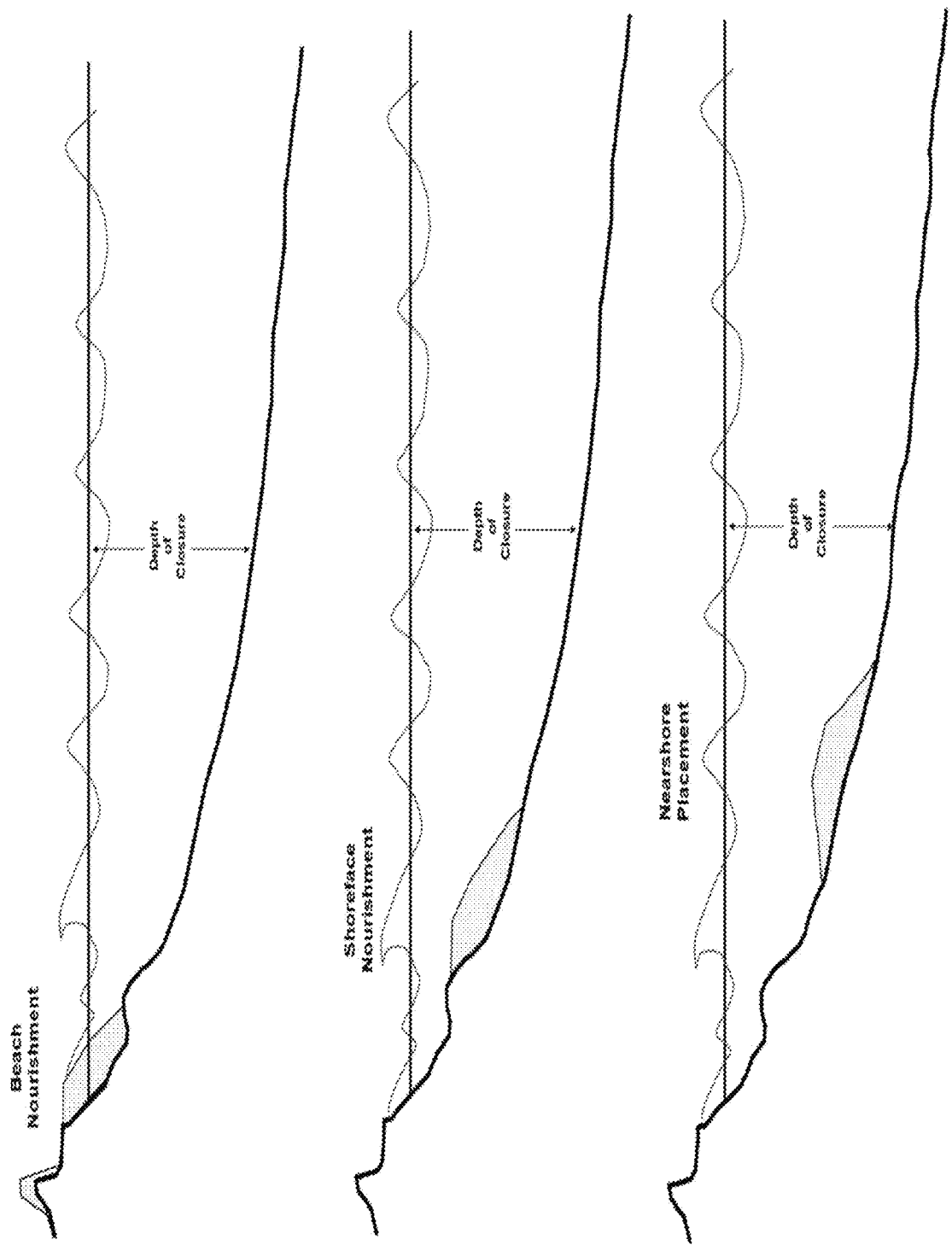
FIG. 46 schematically illustrates beach nourishment, shoreface nourishment, and nearshore placement of a carbon capture sand, in accordance with some embodiments.
Figure 47:
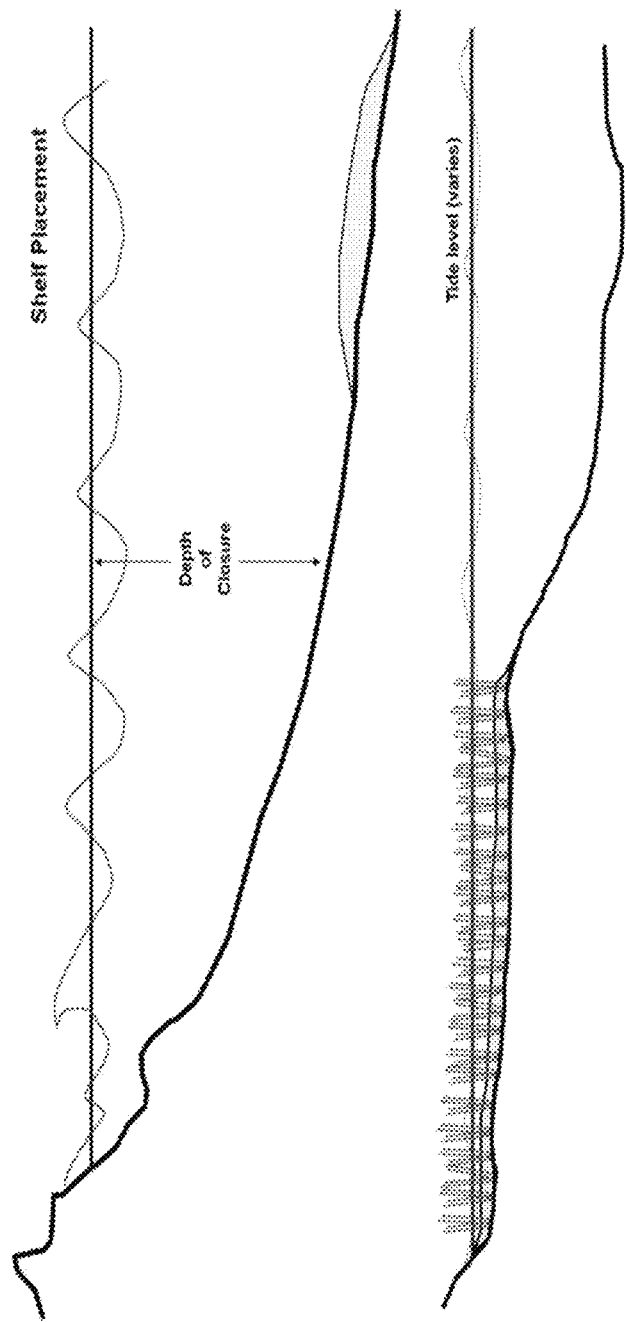
FIG. 47 schematically illustrates shelf placement and marsh placement of carbon capture sand, in accordance with some embodiments.

2. Design of carbon-removing sand placement. The carbon-removing sand may be designed for placement underwater in the form of mounds, berms, shoreface nourishment, or similar features, underwater in dispersed thin layers, on the beach such as in a form commonly used in beach nourishment, or in bays, estuaries, or marshes such as in thin layer placements. FIGS. 46 and 47 illustrate potential carbon-removing sand placement options. Design may consist of a monolithic placement covering a continuous area or of several segmented placement areas considered to be part of the same project design. Factors related to placement location or a continuous or dis-continuous placement may include but not be limited to effect on sediment transport, effect on wave conditions, effect on erosion and accretion patterns on adjacent shorelines, or effect on efficiency of carbon uptake. A sediment transport model may be used to complete this task.

3. Transport selected material to dispersal site. The carbon-removing sand may be transported (e.g., by rail, ship, or truck) to the target site. This site may be a coastal or open water environment. This site may be marine, lacustrine, or riverine. In some cases, selection of transport mechanism and route may involve use of a life cycle analysis, which may utilize all of, some but not limited to the following parameters for, among other purposes, calculating carbon dioxide emissions associated with the transport of carbon-removing sand: transport distance, power, energy efficiency, and cost.

4. Disperse of selected carbon-removing sand or carbon-removing sand blend. Carbon-removing sand or sand blend may be dispersed at the selected site from land or water (e.g. by truck, ship, or barge). In some embodiments, sand may be deployed from a split-hull barge, from the shore via truck, or during dredging. In some embodiments, dispersion can be achieved wholly through mechanical means. In yet other embodiments, dispersion can leverage natural sediment transport or other natural forces to achieve dispersion. In some cases, selection of dispersion mechanism may involve use of a sediment transport model and/or life cycle analysis, which may utilize all of, some but not limited to the following parameters: transport distance, energy efficiency, power, cost, grain size, density, tonnage, wave energy, climate patterns.

5. Environmental conditions may accelerate carbon dioxide removal. This may include energy from waves, tides, and currents which act to mechanically accelerate the rate of dissolution of carbon-removing sand. Grain-on-grain collisions can cause fine fraction particles (<10 microns) to form, which then weather very rapidly by increasing an amount of surface area of the olivine grains that is exposed to seawater. Grain-on-grain collisions may also prevent the formation of surface coatings on the carbon-removing sand. Bioturbation, waves, tides, and currents may also facilitate water recharge around the carbon-removing sand, and thereby enhancing fluid-mineral interactions and reduce or eliminate secondary mineral coatings or the formation of secondary weathering products (e.g., precipitation of secondary clays and carbonate phases). In all cases, the carbon-removing sand may consequently dissolve in the water rapidly, accelerating the reaction which removes carbon dioxide from the ocean/atmosphere.

Figure 48:
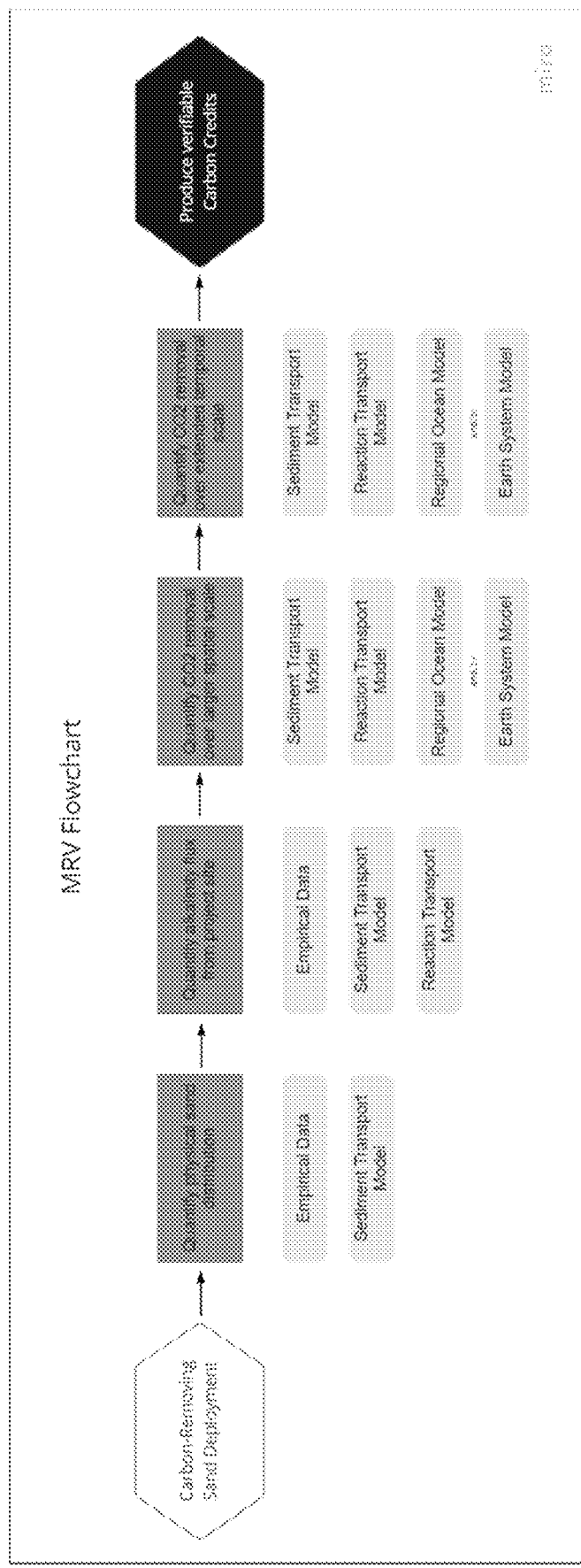
FIG. 48 schematically illustrates a flowchart for measuring, recording, and verifying. validating carbon credits associated with carbon-removing sand activity, in accordance with some embodiments.
Figure 49:
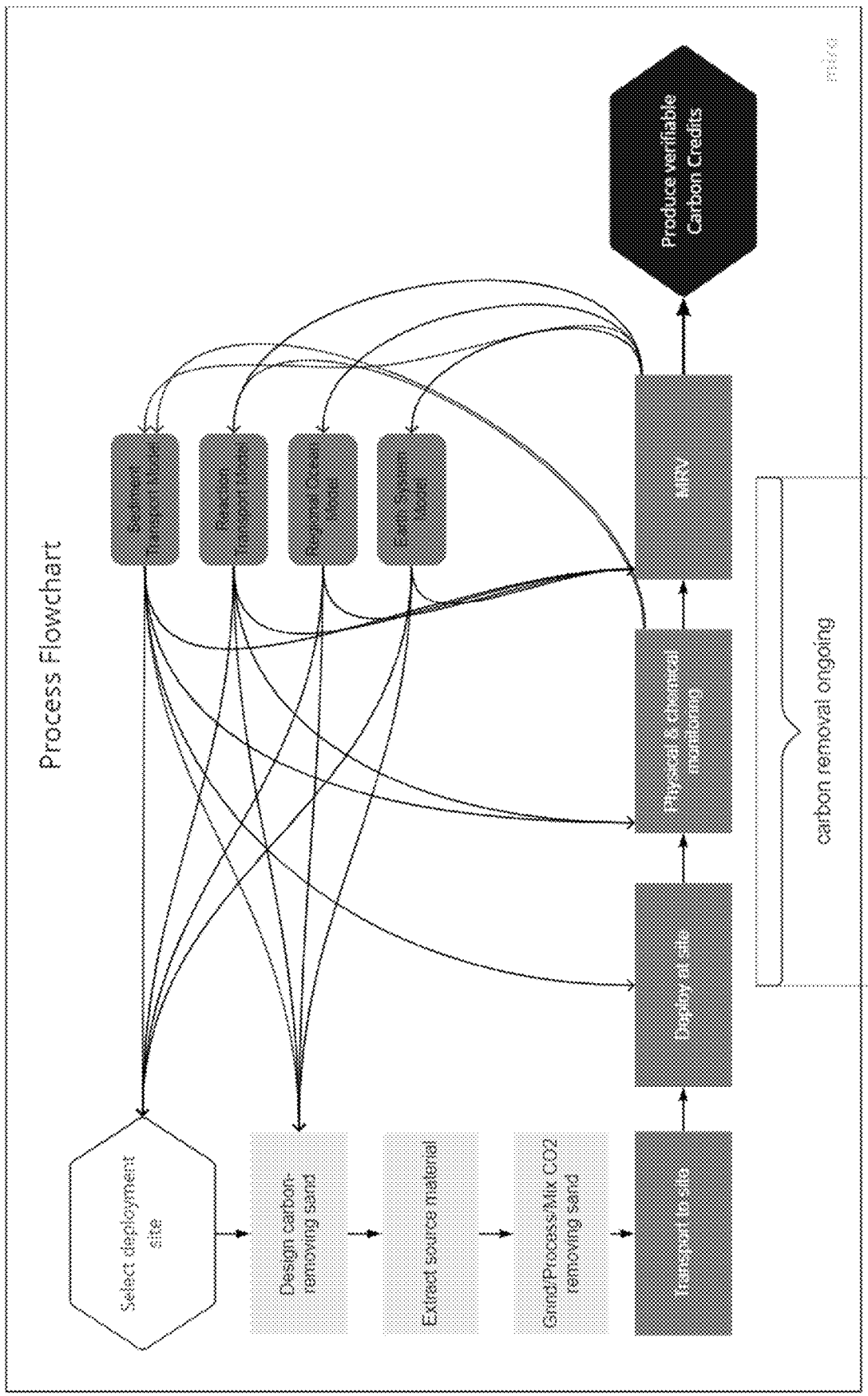
FIG. 49 schematically illustrates a flowchart for one or more models integrated to a process of deploying carbon-removing sand, in accordance with some embodiments.

6. Measurement, reporting, and verification (MRV) relating to carbon dioxide removal. In some cases, measurements may be made to assess rates of dissolution of olivine and carbon dioxide removal. In some cases, these may be chemical measurements including but not limited to carbonate chemistry, trace metals, nutrients, oxygen, organic carbon, salinity, and temperature in the water and or/pore waters at and/or surrounding the dispersal site. In some cases, a geochemical model may be used to interpret data for the purpose of MRV and/or for the purpose of refining steps 1-6. In some cases, a sediment transport model may be used to interpret data for the purpose of MRV and/or for the purpose of refining steps 1-6. In some cases, a regional ocean system model and/or an earth system model may be used for the purpose of MRV. In some cases, multiple models may be coupled. FIG. 48 demonstrates potential model configurations that can be employed to conduct MRV.

Figure 5:
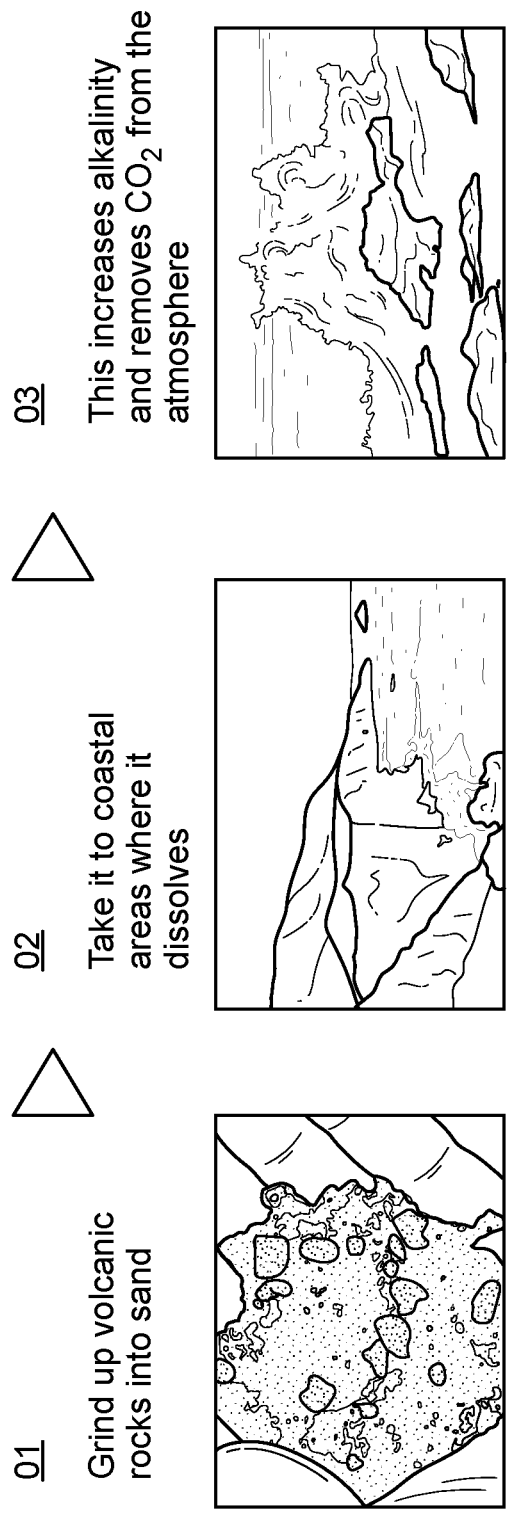
FIG. 5 schematically illustrates one exemplary method for using carbon-removing sand to remove atmospheric carbon dioxide and increase ocean alkalinity, in accordance with some embodiments.
Figure 6:
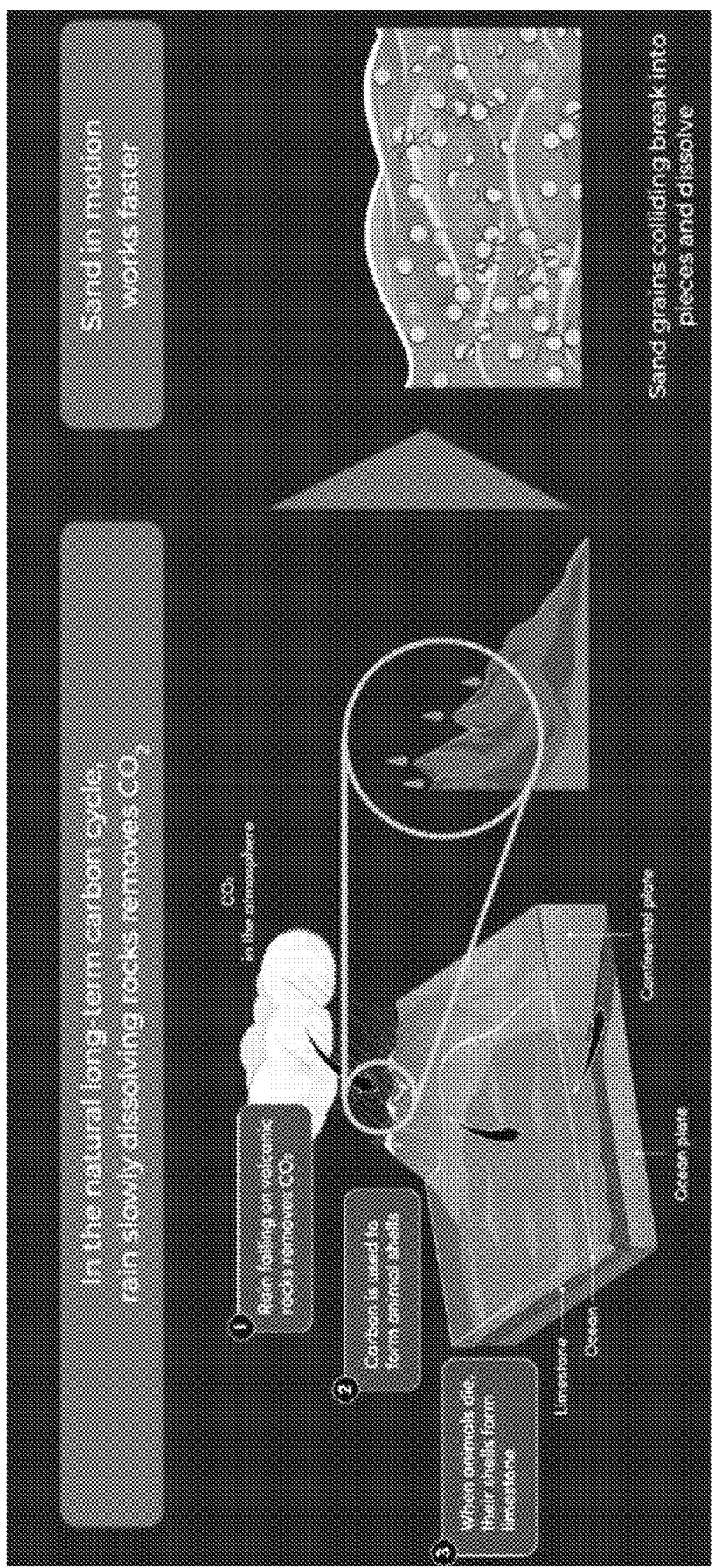
FIG. 6 schematically illustrates the use of wave energy to cause sand grains and/or carbon-removing sand grains to collide and break into smaller pieces, thereby facilitating the dissolution of olivine, in accordance with some embodiments.

FIG. 5 illustrates one exemplary method for using olivine to remove atmospheric carbon dioxide and increase ocean alkalinity. As shown in FIG. 6, wave energy may cause sediment grains to collide and break into smaller pieces, thereby facilitating the dissolution of olivine.

Co-Benefits of the methods described herein include, for example: reduction in seawater acidity. Ocean acidification has been shown to damage marine ecosystems. Carbon-removing sand increases local pH levels, potentially mitigating the adverse effects of ocean acidification on marine ecosystems, potentially improving aquaculture and fishery yields, bolstering local economies at target deployment sites as well as reversing damage to marine ecosystems.

Figure 7:
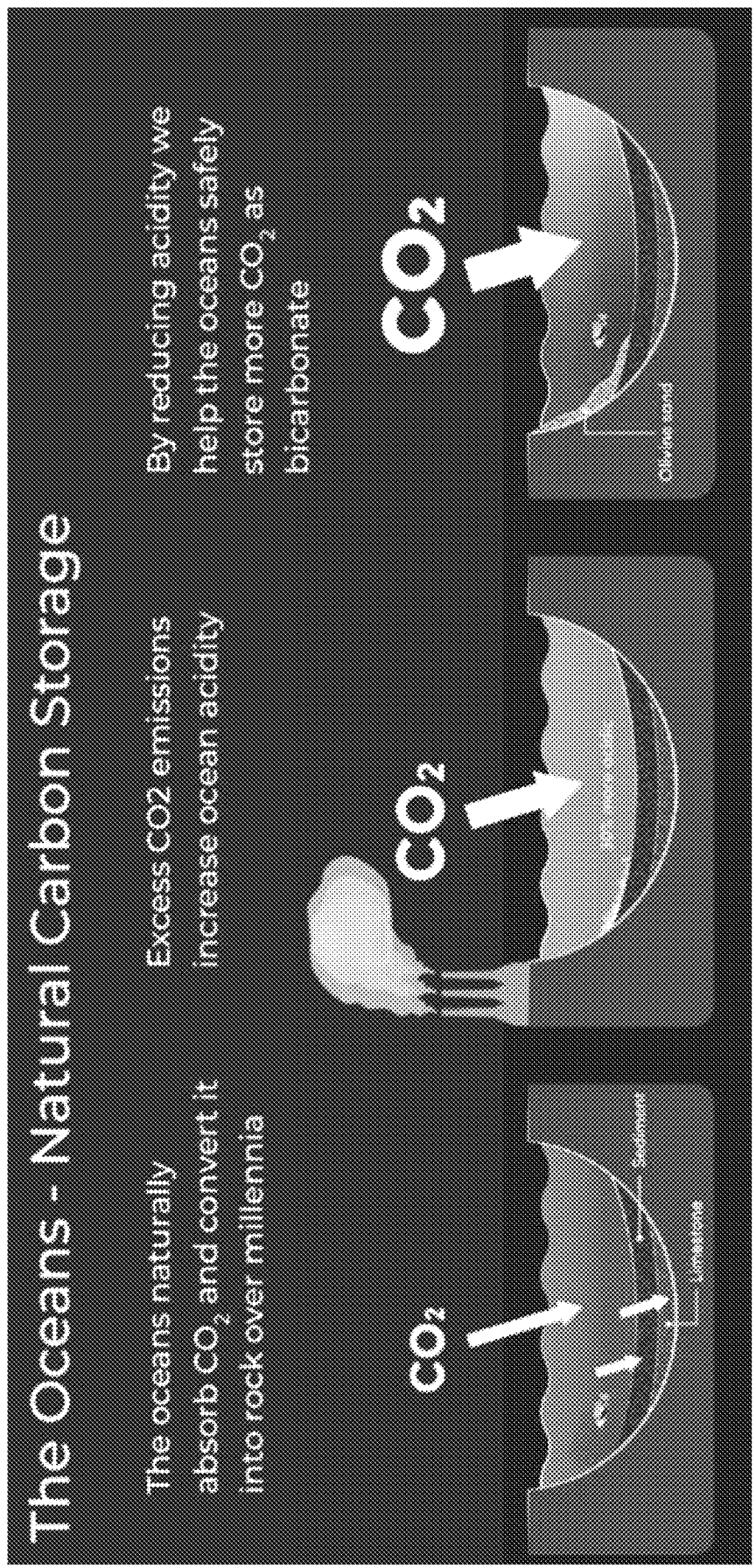
FIG. 7 schematically illustrates an example of how the oceans can be used for natural carbon storage, in accordance with some embodiments.
Figure 8:
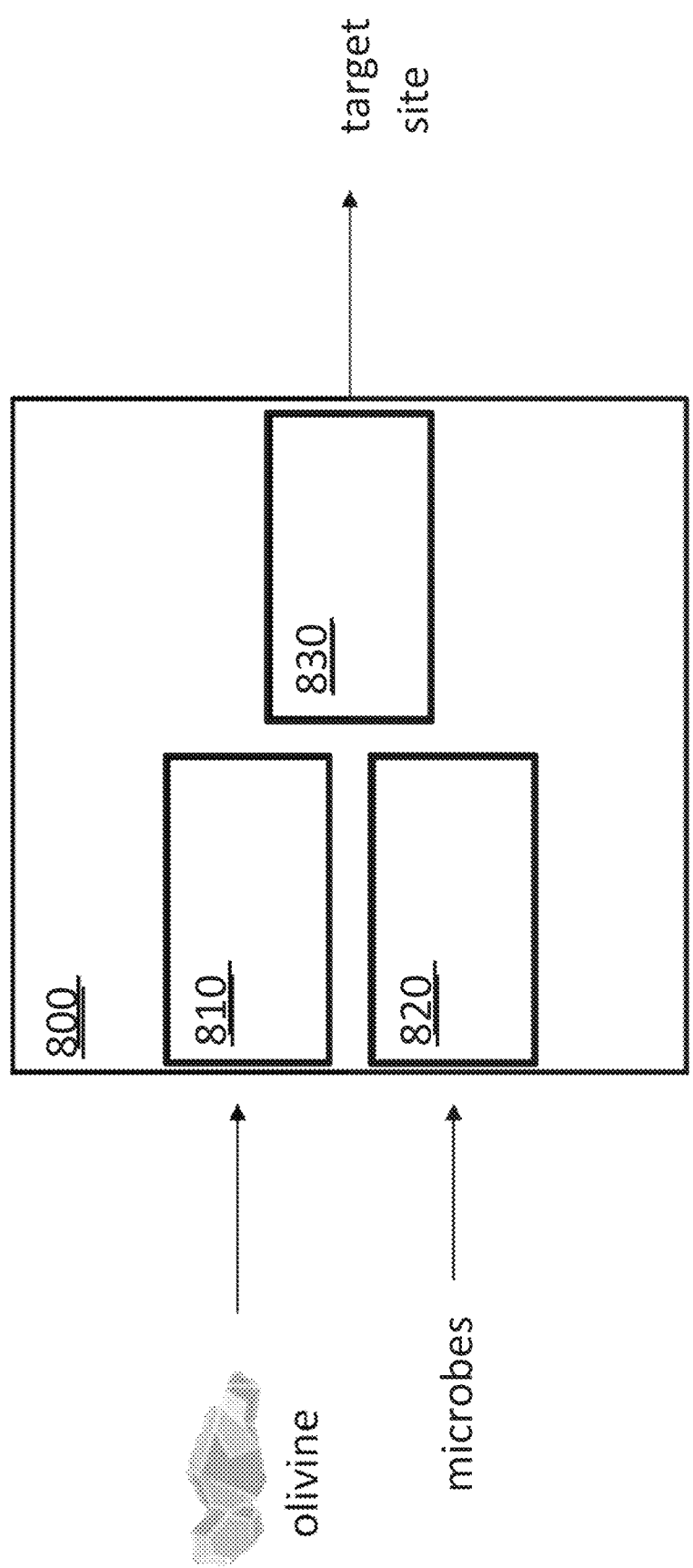
FIG. 8 schematically illustrates an example of a bioreactor, in accordance with some embodiments.

FIG. 7 illustrates an example of how the oceans can be used for natural carbon storage. Excess carbon dioxide emissions may increase ocean acidity. The systems and methods of the present disclosure may be implemented to reduce seawater acidity and help the oceans safely store more carbon dioxide as bicarbonate.

Co-Benefits of the methods described herein may also include, for example: support for diatom growth. Diatoms, marine photosynthetic microalgae, are a cornerstone of marine food webs and capture carbon dioxide through photosynthesis, creating 40% of oxygen on Earth. Diatom abundance has decreased as carbon dioxide has risen, partly due to decreasing concentrations of silicate in the ocean due to damming of rivers, limiting sediment movement. Since some forms of carbon-removing sand (e.g., olivine) are primarily magnesium silicate, the increase in silicate concentrations from dissolution of such carbon-removing sand may lead to diatom growth. Increases in diatoms would increase the health of marine ecosystems and support photosynthetic carbon capture.

Other co-benefits can include, for example, supporting coastal communities facing enhanced coastal erosion and sea level rise by supplying a low-cost source of sediment (which, in some cases, may be paid for using carbon credits).

Mechanics and Chemistry of Weathering and Dissolution

Using energy in the natural environment, including and not limited to wave action, to break down the carbon-removing sand is critical to the efficiency of carbon dioxide removal. Past analyses have shown that grinding carbon-removing sand to <100 µm size is highly energy-intensive. However, grinding carbon-removing sand to >300 µm sand requires far less energy. In some cases, the carbon-removing sand has a particle size that is less than or equal to about 10 mm, 5 mm, 2 mm, 1 mm, 900 µm, 750 µm, 600 µm, 500 µm, 450 µm, 400 µm, 350 µm, 300 µm, 250 µm, 200 µm, 150 µm, 100 µm, 50 µm, 25 µm, or less. In some cases, the carbon-removing sand has a particle size that is greater than or equal to about 25 µm, 50 µm, 100 µm, 150 µm, 200 µm, 250 µm, 300 µm, 350 µm, 400 µm, 450 µm, 500 µm, 600 µm, 750 µm, 900 µm, 1 mm, 5 mm, 10 mm, or greater. In some cases, the carbon-removing sand has a particle size that is between two values described above, for example between about 250 µm and about 500 µm. Using the natural, free energy of water movement to break the carbon-removing sand down further reduces the milling and grinding energy to a small proportion of the total.

In some cases, grain-on-grain collisions may rapidly break down carbon-removing sand. Carbon-removing sand grains may be reduced in size due to mechanical activation. In some cases, the motion of the water in which the carbon-removing sand is provided may cause surface abrasions. In some cases, the surface of the carbon-removing sand grains may be mechanically activated to enable and/or enhance carbon dioxide uptake and de-acidification.

Dissolution Kinetics

Figure 42:
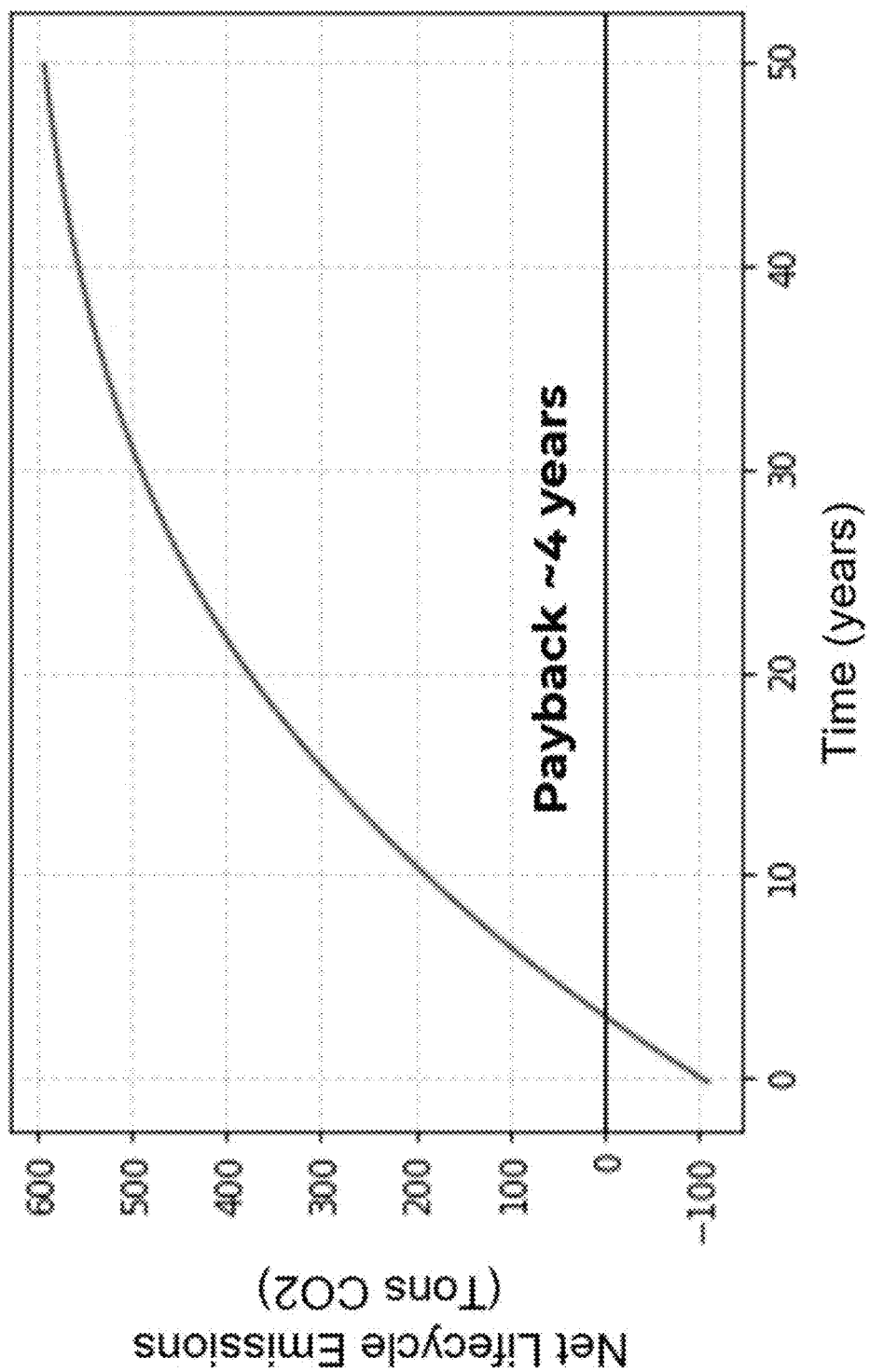
FIG. 42 schematically illustrates an example of a carbon payback period that can be realized using the methods and systems disclosed herein, in accordance with some embodiments.
Figure 44:
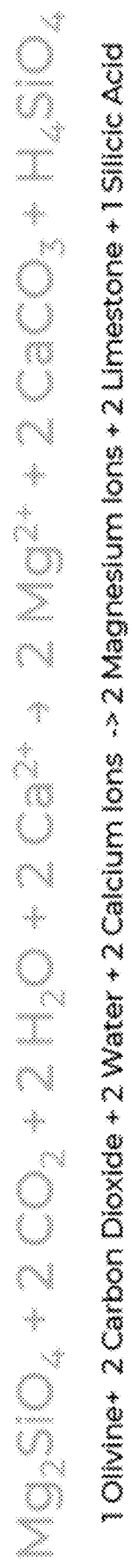
FIG. 44 schematically illustrates the effects of secondary carbonate precipitation on CO2 capture efficiency, in accordance with some embodiments.

FIG. 42 illustrates various plots showing exemplary olivine dissolution kinetics for olivine particles having different grain sizes. Dissolution time may decrease as carbon-removing sand particle sizes decrease. The particle dissolution characteristics may be predicted or simulated using a shrinking core model and one or more laws, equations, or principles governing carbon-removing sand dissolution rates. In some cases, the shrinking core model may be modified to permit the simulation of dissolution for realistic, commercially-available grain size distributions of carbon-removing sand. The models described herein may be generated by modifying initial diagenesis models to incorporate carbon-removing sand dissolution kinetics that correspond to the shrinking core model. The models may include and/or account for full carbonate chemistry (e.g., DIC, ALK, $pCO_2$, pH, carbonate precipitation/dissolution) as well as biogeochemical processes (including aerobic and anaerobic respiration, formation of Fe/Mn oxides, pyrite, sulfide oxidation, etc).

Secondary Minerals

In some instances, secondary carbonate precipitation as shown in FIG. 43 can impact carbon dioxide capture efficiency. Secondary carbonate precipitation may change the reactions described herein such that for every 1 mol of olivine introduced to a target environment, 2 moles of carbon dioxide are consumed and 0 moles of alkalinity are generated. This can result in a 50% reduction in carbon dioxide capture efficiency. The systems and methods disclosed herein may be implemented to minimize or reduce secondary carbonate precipitation. The rate of carbonate precipitation can be strongly controlled by local variations in geochemistry and biogenic calcification. In some cases, alkalinity export can be the dominant process occurring in sediments, and once mixed into the water column, consumption of alkalinity can be low given the long residence time of DIC and ALK in seawater.

Figure 45:
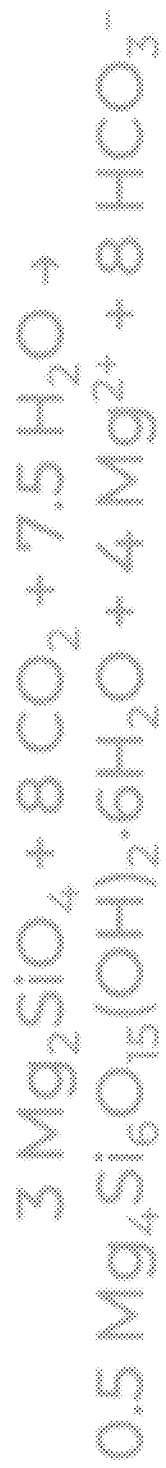
FIG. 45 schematically illustrates the effects of secondary clay formation on carbon dioxide capture efficiency, in accordance with some embodiments.

In some instances, secondary clay formation as shown in FIG. 45 can impact carbon dioxide capture efficiency. Secondary clay formation may change the reactions described herein such that for every 1 mol of olivine, 8/3 moles of carbon dioxide are consumed and 8/3 moles of alkalinity are generated. This can result in a 33% reduction in carbon dioxide capture efficiency. The systems and methods disclosed herein may be implemented to minimize or reduce such secondary clay formation.

Although enhanced silicate weathering may be implemented in some instances, none of the prior work has recognized and provided methods for the manufacture of engineered carbon-removing sand with specific suitable colors, grain size, density, and reactivity required to meet specific regulatory, environmental, cultural, aesthetic, and engineering requirements for coastal construction projects. Moreover, prior work has completely neglected the engineering of these specific attributes in order to create safe and successful materials for coastal construction projects. No existing material used in present coastal construction projects provides additional public and ecological benefits due to carbon dioxide capture, alkalinity generation, and the mitigation of seawater acidification. Likewise, no prior approaches have realized the simultaneous benefits derived from manufacturing carbon-removing sand which are suitable for coastal construction projects, thus providing the benefits of mitigating coastal erosion, combating sweater acidity and decreasing atmospheric carbon dioxide.

Deployment Material Design

Carbon-Removing Sand

The present disclosure provides carbon-removing sand, sand blends, and processes for producing the same. The carbon-removing sand may comprise specially selected, prepared, and blended particles which [1] are suitable to mitigate coastal erosion along coasts [2] interact with carbon dioxide ($CO_2$) and/or dissolved carbonic acid [$H_2CO_3$] to produce bicarbonate [$HCO_3^-$], [$CO_3^{2-}$] ions, and/or solid-phase carbonate minerals [Ca, Mg]$CO_3$, thus [3] simultaneously mitigating the impacts of climate change, sweater acidity, and coastal erosion.

In order to be suitable for use in coastal construction, beach nourishment, and marsh restoration projects, [4] manufactured carbon-removing sand and blends thereof should closely match or approximate the texture, grain size distribution, and color of native sediment so as to comply with applicable legal requirements or standards, minimize or prevent environmental impacts, or, more generally, for aesthetic reasons. Thus, the processes for preparing carbon-removing sand and sand blends may be tailored such that the carbon-removing sand and blends thereof produce and achieve these specific pre-determined properties.

In one aspect of the invention, to efficiently remove carbon dioxide from the atmosphere, [5] carbon removing sand may be manufactured from an alkaline material(typically naturally occurring olivine, dunite, basalt, serpentinite, serpentine, brucite, wollastonite, or industrial-produced mineral-equivalents such as slag). These minerals [6] may interact with water and carbon dioxide and/or carbonic acid to produce bicarbonate ion as a product, thereby decreasing the acidity of the surrounding fluid and converting the harmful carbon dioxide or carbonic acid into environmentally beneficial bicarbonate or carbonate ion. An example describing the reaction of forsterite olivine ($Mg_2SiO_4$) is provided below, although other minerals and rocks described in this disclosure result in equivalent reactions converting carbonic acid to bicarbonate ion:

$$CO_2 + H_2O \rightarrow H_2CO_3 \qquad 1.$$

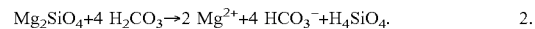
$$Mg_2SiO_4 + 4\,H_2CO_3 \rightarrow 2\,Mg^{2+} + 4\,HCO_3^- + H_4SiO_4. \qquad 2.$$

The dissolution of carbon-removing sand may effect the conversion of gaseous and dissolved carbon dioxide into dissolved bicarbonate and carbonate ions, thereby increasing the capacity of fresh and salt water to store additional carbon in a dissolved state. When present as dissolved bicarbonate and carbonate ions, rather than carbon dioxide, these compounds may no longer contribute to climate change and can act to counter the effect of seawater acidity.

In order to simultaneously achieve the requirements of sand and sediment for coastal construction projects, while preserving such materials ability to remove carbon dioxide described above, [7] it may be necessary to prepare specially prepare the reactive mineral components and then blend these components in specifically determined ratios with native or allochthonous sand and sediment (i.e., non-carbon-removing sand) to achieve the desired chemical, engineering, and aesthetic properties. This process is described in greater detail below:

The process for preparing the carbon-dioxide-removing component of carbon-removing sand begins with a feedstock of alkaline materials. A list of potential feedstocks is provided in Table 1.

TABLE 1

Potential feedstock materials for the production of the carbon-dixoide-reactive component of carbon removing sand.

Naturally Occurring Rocks: Peridotite, Dunite, Harzburgite, Lherzolite, Basalt, Basaltic Glass, Gabbro, Komatiite, Serpentinite, Kimberlite
Naturally Occurring Minerals: Olivine, Forsterite, Fayalite, Enstatite, Pyroxene, Serpentine, Brucite, Wollastonite
Industrial Byproducts: Blast-furnace Slag, Steel-furnace Slag, Basic-oxygen-furnace Slag, Electric-arc-furnace Slag, Ladle Slag.

(d)

The preparation of the carbon-dioxide-removing components of carbon removing sand may proceed via two critical steps:
  (1) The feedstock may be crushed and/or milled to increase the surface area of the feedstock and provide fresh surfaces for interaction with carbon dioxide. Because the weathering process occurs only on the surfaces of the grains and within microcracks created by the crushing/milling process, it is essential to increase the available reaction surface area to the maximum extent possible in order to maximize the material weathering.
  (2) The crushed and milled material may then be size sorted using sieves, gravity separation, air classifiers, to provide a final product with a mean grain size and overall grain size distribution which meets the engineering specifications of the coastal construction project. In some cases, this process may be designed to exclude excessive fine-grained material and/or coarser particles, to produce an intermediate grain-size material which closely matches the size distribution of the native sediment in the geographic region receiving the carbon-removing sand. As an alternative to preparing batches of carbon-dioxide-removing components individually, it is also possible to presort the material into various predetermined size ranges and then select and/or blend from these pre-classified separates to achieve an overall blend suitable for use in a specific project.

In most cases or all cases, the carbon-dioxide-removing component may be further modified via mixing non-carbon-removing sand or sediment in order to achieve a combination of texture, color, and density, and engineering properties suitable for use in coastal construction projects. To achieve this, a third step may be required:
  (3) The carbon-dioxide-removing mineral component may be blended with one or more non-carbon-removing sand or sediment materials to achieve a predetermined ratio providing the specified properties. A list of common non-carbon-removing feedstocks is provided in Table 2. Blends consisting of 1-50% carbon-removing component may be most common, but other variations of this invention, higher or lower fractions of the carbon-removing component may be used.

TABLE 2

Potential feedstock materials for the non-carbon-removing component of carbon-removing sand.

Naturally Occurring Native Sediment at the Project Site: May include native sand, silt, clay, organic matter and gravel
Naturally Occurring Rocks/Sediment: Silicate Beach Sand, Carbonate Beach Sand, Dredged Sediment, Crushed Sandstone, Crushed Limestone, Carbonate Ooids
Naturally Occurring Minerals: Quartz, Feldspar, Aragonite, Calcite, Garnet, Magnetite, Hematite, Limonite, Ilmenite, Smectite, Chlorite, Biotite, Muscovite, Rutile, Zircon and Monazite (e)

The goal of blending the carbon-removing- and non-carbon-removing components of carbon-removing sand is to achieve a final bulk product meeting various regulatory, aesthetic and engineering requirements including color, texture, grain size, density, cohesion, hardness, etc. To realize a blended mixture between the carbon-removing and non-carbon-removing components of the carbon-removing sand, the individual components may either be brought together in advance, or in alternate embodiments, separately conveyed or placed onto the project site in such a manner to realize an appropriate mixture over the duration of the project (ie. mixing between components occurs via the physical motion of sediment driven by conveyors, heavy equipment, bioturbation and/or waves, tides and/or currents). A sediment transport model may be used to determine the appropriate method of achieving the final bulk product.

Improving Performance of Carbon Removing Sand

In another aspect, the present disclosure provides systems and methods for optimizing olivine for use in the field as a carbon-removing sand. Such optimization may comprise, for example, determining the optimal grain size distribution of olivine sand for use in carbon capture (covering combinations of grain size, color, blends, includes modeling grain size distributions and placement designs for specific sites which may use a sediment transport model); and physically and/or chemically processing the olivine (e.g., using machinery) to prepare one or more batches of carbon-removing sand suitable for coastal engineering projects.

FIG. 4 illustrates olivine and mixtures of non-carbon-removing sand and olivine. In some cases, the olivine may be mixed with natural beach sand before the olivine is deployed at a target site. The mixture comprising the olivine may comprise at least about 5%, 10%, 15%, 20%, 25%, or 30% olivine by weight or volume. In some cases, the mixture may comprise more than 30% olivine by weight or volume. In some cases, the mixture may comprise less than 5% olivine by weight or volume. In some cases, the mixture may comprise between about 5% and about 30% olivine by weight or volume.

Olivine (or any other type of alkaline material) can be processed to yield fine grains with increased surface area exposure and/or micro-fractures, which can speed up dissolution and the carbon dioxide capture process. The olivine dissolution and carbon dioxide capture process can also be accelerated by (i) using easily weatherable and soluble minerals, (ii) increasing an amount of surface area of the olivine grains that is exposed to a solvent (e.g., water or seawater), (iii) enhancing fluid-mineral interactions, and/or (iv) reducing or eliminating secondary mineral coatings or the formation of secondary weathering products (e.g., precipitation of secondary clays and carbonate phases). The olivine dissolution and carbon dioxide capture process can further be accelerated by bioturbation, waves, tides and/or currents (1) by spreading the olivine from the placement site (2) causing grain-grain collisions (3) refreshing overlying water, reducing saturation.

Olivine is a common, naturally occurring volcanic mineral, with physical properties similar to quartz. Olivine may be 23% denser than pure quartz sand (1.43 tons/cy). Olivine sand is a clean upland sand that is ~25% denser than typical silicate sand, and that can be artificially milled to be compatible with native grain size. Darker and lighter olivine sources allow for color matching to the native sand color.

One type of olivine may be white olivine, or Forsterite ($Mg_2SiO_4$). This is a magnesium rich form of olivine, known as Forsterite (Mg2SiO4). Weathering 1 ton of olivine can remove up to 1.25 tons of carbon dioxide from the atmosphere.

Deployment Material Production

In another aspect, the present disclosure provides systems and methods for preparing carbon-removing sand for optimal dissolution. The carbon-removing sand grains may be part of a source material comprising olivine sand or a mixture comprising olivine sand and native or allochthonous sand and sediment In some cases, the method may comprise crushing raw materials for carbon-removing sand to yield an optimal grain size and aggregating raw or crushed olivine into pellets. Such processing of the olivine may enhance dissolution of olivine, thereby accelerating the carbon capture process. In some cases, the method may further comprise selecting, milling, and/or making compatible olivine sand and native sediment for the purpose of coastal construction, beach nourishment and carbon capture.

Pellets

In some embodiments, pelletized olivine aggregates formed from olivine fines may be prepared through a number of processes disclosed herein including [1] the use of a binding agent (such as but not limited to clay, polysaccharides, proteinaceous compounds, resin, plastic, glass, etc.) [2] via encapsulation of smaller olivine grains with said binding agent or other similar materials or [3] via the thermal fusion or physical compression of smaller olivine grains into larger aggregates.

In some embodiments, the pellets may be designed to either [4] remain substantially intact while maintaining improved surface area via internal porosity and permeability or [5] degrade in a controlled fashion to release olivine fines to the environment in a prolonged controlled fashion. In some cases, [6] the preparation of such pellets may allow olivine dissolution to occur substantially faster than would occur for equivalently sized solid pure olivine grains, thereby improving the process of carbon capture while minimizing the aesthetic, health, and ecological harm and challenges posed by working with and utilizing olivine mineral fines.

Deployment Site Selection

The selection of sites for the implementation of CCC may be critical to the efficacy of the method. Key factors may include climate, weather, wave conditions, tides, currents, seawater circulation patterns, sediment composition, sediment grain size, ecology, accessibility, and social license. In some cases, an environmental impact assessment may be used to identify the presence or absence of threated, endangered, protected, or culturally significant species and their respective sensitivities to sediment, such as for nesting habitat. In some cases, a sediment transport model may be used to inform site selection and predict physical sediment behavior in a geographic region. In yet other cases, a reactive transport geochemical model may be used for simulation of distributing carbon-removing sand in a target environment with one or more known biological, chemical, or ecological properties or characteristics. In yet other cases, a regional ocean model system or earth system model may be used to track air-sea water-gas carbon dioxide fluxes and ensure ample time for air-sea carbon dioxide exchange and carbon removal. In some cases, sediment transport, reaction-transport, and regional or Earth system models may be coupled, integrated, or used iteratively to inform the selection of deployment sites.

In some cases, measurements obtained using sensors (remote, in-situ, ex-situ) may be used to adjust the location in which the carbon-removing sand is introduced.

In some cases, geochemical models (e.g. reaction-transport) may be used to optimize the location in which the carbon-removing sand is introduced. The models may be configured to simulate sediment porewater profiles, water column and porewater chemistry (e.g., pCO2, DIC, pH, DO, TA, nutrients, metals, DOC), solid-phase chemistry and benthic fluxes, secondary clay mineralogy, and trace metal speciation and cycling.

Deployment Site Design

The engineered design of a deployment is critical to the success of meeting coastal construction goals, capturing carbon, and minimizing or eliminating environmental or cultural impact.

In some cases, a sediment transport model may be used to inform deployment design including quantity of the deployment, physical distribution of the deployment, sediment sorting, location of the deployment within the target area and placement geometry.

In some cases, measurements obtained using sensors (remote, in-situ, ex-situ) may be used to adjust the configuration/form in which the carbon-removing sand or blend is deployed.

In some cases, geochemical models (e.g. reaction-transport) may be used to optimize the configuration/form in which the carbon-removing sand or sand blend is deployed distributed. The models may be configured to simulate sediment porewater profiles, water column and porewater chemistry (e.g., pCO2, DIC, pH, DO, TA, nutrients, metals, DOC), solid-phase chemistry and benthic fluxes, secondary clay mineralogy, and trace metal speciation and cycling. In some cases, the models may be used for simulation of distributing carbon-removing sand in a target environment with one or more known biological, chemical, or ecological properties or characteristics.

Sediment transport data and models may be linked to geochemical reaction-transport data and models to predict and/or constrain geochemical parameters including and not limited to carbon-removing sand dissolution, alkalinity production, trace metal dissolution, and nutrient availability under different design scenarios. Sediment transport and reaction-transport models can be used together or separately to inform potential environmental impact such as the presence or absence of carbon-removing sand in ecologically or culturally significant areas under different design scenarios and environmental conditions.

Shipping and Distribution

[7] In another aspect, the present disclosure provides systems and methods for shipping and deploying olivine. In some cases, the shipping and deployment of olivine may be performed using a device for distributing carbon-removing sand in shallow marine environments. The device may be, for example, a spreading device for spreading the olivine in a desired or optimal manner at a target site (e.g., a beach of interest).

In some cases, the methods of the present disclosure may comprise determining whether one or more dredging activities or other local modifications are needed in order to optimally distribute the carbon-removing sand. Such determination may be based on one or more sensor readings and/or information about the target site in which the carbon-removing sand is to be distributed.

In some cases, the carbon-removing sand may be processed before shipping to facilitate shipping and distribution of the carbon-removing sand. For instance, the olivine may be modified to enable transportation of ultra-fine material (e.g., for reduction of liquefaction or capsizing risk).

In some cases, measurements obtained using sensors (e.g. remote, in-situ, ex-situ) may be used to adjust the rate at which the carbon-removing sand is introduced and the method by which the carbon-removing sand is distributed.

In some embodiments, various types and forms of maritime emissions reduction technology (e.g., an on-board olivine reactor driven by ship engine using ballast water) may be implemented. In some cases, bulk carrier direct deployment technology and related modifications (e.g., open sea distribution for in situ weathering) may be utilized. In some cases, grain washing and liquid alkalinity systems may be used for pre-deployment reduction of turbidity.

In some cases, global logistics software may be used to mobilize idle maritime assets for carbon removal projects involving carbon-removing sand.

Figure 9:
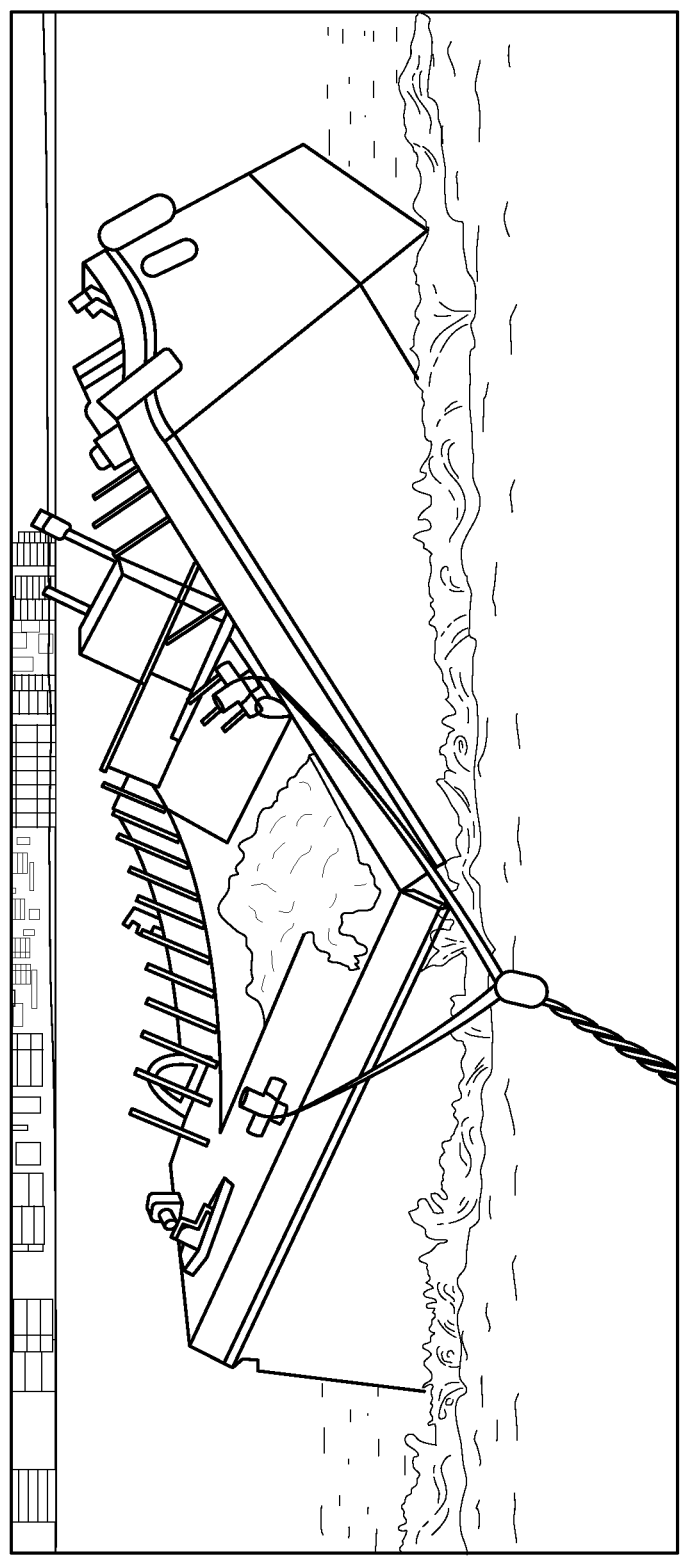
FIG. 9 schematically illustrates an example of a system for deploying olivine for coastal nourishment, in accordance with some embodiments.

FIG. 9 schematically illustrates an example of a system that may be used to deploy carbon-removing sand for coastal engineering projects. The system may comprise, for example, a split hulled hopper barge. In some cases, rock containing carbon-removing minerals may be mined and milled into carbon-removing sand components and loaded and shipped on dry bulk carriers to designated ports. The carbon-removing sand components may then be loaded into one or more split hulled hopper barges. In some embodiments, the barges may be linked together and towed to designated deployment sites. Once the barges are positioned at or near the designated deployment sites, the bottom of the barges may be configured to open in order to deploy the carbon-removing sand components at a specified rate to result in the in-situ production of carbon-removing sand. In some cases, sediment transport modeling may be used to predict where and how the carbon-removing sand will be transported once deployed, and in what direction the carbon-removing sand will likely disperse under different environmental conditions.

In order to reduce, neutralize, or negate carbon dioxide emissions which occur during the combustion of fossil fuels during conventional dredging operations, a predefined ratio of carbon negative sand may be mixed with the dredging spoils in order to [1] result in the net capture of a specified amount of carbon dioxide and [2] ensure that the dredged or other sediments meet engineering and regulatory requirements for disposal or beneficial reuse. Blends consisting of 1-50% carbon-removing sand component may be most common, but in other variations, higher or lower fractions of the carbon-removing sand component may be used.

In order to mix carbon-removing sand with dredged materials, several different approaches may be used depending on the type of dredging operation and intended fate of the dredged material. During cutterhead dredging operations, pump-out hopper dredging, and other approaches where dredged material is conveyed via a hydrologic slurry, the carbon-removing sand may be directly mixed with the dredge spoils by injecting the carbon-removing sand into the slurry pipeline. When using trailing suction hopper dredges, carbon-removing sand may be mixed within a sediment hopper or barge prior to discharge. As an alternative, carbon-removing sand may be directly placed at the sediment destination in the specified quantity and allowed to mix with the dredge spoils via the action of bioturbation, wind, waves, tides, and currents.

Carbon-Removing Marine Landfill Cap

In another aspect, the present disclosure provides carbon-removing marine landfill caps, processes for making the same, and processes for quantifying carbon capture from carbon-removing marine landfill caps. Marine landfills may serve as long-term, seafloor placement areas for unwanted construction debris, dredging materials, and toxic pollutants. Currently, marine landfills are often "capped" with non-toxic clay or sand or other similar materials to prevent contamination of overlying seawater and allow marine life to thrive in previously environmentally damaged areas. By using carbon-removing sand wholly, or as a constituent of, marine landfill caps, these sites can serve as climate change mitigation locales and further encourage the regeneration of environmentally damaged areas through the production of bicarbonate (alkalinity) which offsets ocean acidification and is beneficial for marine life.

The process of making and deploying carbon-removing marine landfill cap differs from traditional marine landfill cap because 1) the depth (thickness) of carbon-removing cap sand 2) grain size distribution of carbon-removing cap sand, and 3) possible blend of carbon-removing cap and standard cap must be optimized to 1) prevent release of toxic pollutants and similar while allowing for sufficient permeability so that the carbon-removing sand will capture carbon over time and in particular not saturate porewaters such that the carbon removal reaction slows or stops. To achieve these objectives, a carbon-removing marine landfill cap may be deployed wholly as a cap, applied as a single mixture of carbon-removing cap to non-carbon-dioxide-reactive cap sand, or applied in layers where the percentage of carbon-removing cap sand to non-carbon dioxide-removing cap sand changes with depth, or the grain size distribution of carbon-removing cap and/or non-carbon-dioxide-removing cap changes with depth. In all circumstances the carbon capture rates may vary with depth. In some cases, the carbon capture rate may be determined based on analytical measurements and sensor measurements from a particular site, fit to a global model. In some embodiments, the appropriate deployment technique described above may be a function of local wave climate, ecology (bioturbation), seawater temperature, landfill material, and an LCA (life cycle analysis) as the carbon dioxide emitted to deploy the carbon-removing cap must be accounted for to ensure the cap is, indeed, carbon-removing.

Measurement, Reporting, and Verification (MRV)

[5] In another aspect, the present disclosure provides systems and methods for measuring, reporting and verifying (MRV) carbon removal as well as ecological effects of carbon-removing sand in carbon removal over large coastal areas. Such measurements, reporting, and verification of carbon removal may be performed using one or more remote sensors, in-situ sensors, protocols for the use of such sensors (e.g., sensor deployment using benthic flux chambers), ex-situ (e.g. "bench top" sensors and instruments) and algorithms to interpret the data obtained and derived from the sensor readings. In some cases, the sensor readings may comprise measurements of alkalinity, DIC, pCO2, pH, salinity, conductivity, dissolved oxygen, nutrients, trace metals, organic carbon, water temperature, wave activity, and/or additional chemical and physical properties. The system and method for MRV may also incorporate the integration of sensor data with reaction-transport models, sediment transport models, regional ocean system models, earth system models, or coupling of some or all of the aforementioned models. The presently disclosed systems may be used to prove the dissolution of carbon-removing sand and the subsequent capture of carbon dioxide based on the dissolution of the carbon-removing sand. In some cases, the systems and methods disclosed herein may be implemented to predict the transport and dissolution (e.g., by utilizing one or more models for simulating or predicting carbon-removing sand dissolution at a target site).

In a related aspect, the present disclosure provides systems and methods for simulating a target site or environment, which systems and methods can allow for the study of carbon-removing sand dissolution rates in a controlled environment, intermediate between lab and field conditions. Such systems and methods may be implemented to determine and/or monitor carbon-removing sand dissolution rates, porewater or water column geochemistry, or benthic flux measurements, study impacts of temperature on carbon-removing sand dissolution and respiration, track impacts on seawater pH and other water chemistry, monitor ecological responses and air-sea water gas carbon dioxide fluxes, track the fate, transport, and bioaccumulation of trace metals, track the formation of secondary weathering products (e.g., chrysotile, carbonates, clays), and monitor the impacts of the carbon dioxide sequestration processes from carbon-removing sand on benthic invertebrates/meiofauna.

In some embodiments, the MRV methods and protocols disclosed herein may be adapted or adjusted for different types of carbon-removing sand or for different target sites for carbon-removing sand distribution. In such cases, the models used to predict or determine carbon-removing sand dissolution, reaction fluxes, and/or carbon sequestration may be adjusted based on characteristics of the particular carbon-removing- and non-carbon-removing sand mixture used, the target site, and/or one or more sensor readings or measurements obtained in situ.

The models may be configured to simulate sediment porewater profiles, water column and porewater chemistry (e.g., pCO2, DIC, pH, DO, TA, nutrients, metals, DOC), solid-phase chemistry and benthic fluxes, secondary clay mineralogy, and trace metal speciation and cycling.

In some cases, the one or more sensors may be used to monitor and track: carbon-removing sand dissolution rates (porewater geochemistry, benthic flux measurements), carbon dioxide uptake, seawater de-acidification, impacts on water chemistry, ecological response, fate, transport and bioaccumulation of trace metals, and/or formation of secondary weathering products (e.g., chrysotile, carbonates, clays). In some cases, an isotopic tracer may be used to track carbon-removing sand dissolution and simultaneous precipitation of secondary clays and carbonate phases. The sensors may also be used to track carbon-removing sand grains over time (i.e., physical tracking of olivine using dyes/tracers, etc.).

In some cases, the one or more sensors may be used to develop, calibrate and/or validate sediment transport and reaction-transport models.

In some cases, reaction-transport, sediment transport model, regional ocean model systems, and earth system models may be used simulate or predict carbon-removing sand dissolution rates, study the impacts of temperature of olivine dissolution and respiration, track impacts on seawater pH, track air-sea water gas carbon dioxide fluxes, monitor and evaluate fate and transport of trace metals, assess the impacts on benthic invertebrates/meiofauna, track sediment characteristics (e.g., changes in mineralogy, formation of secondary carbonate/clays), monitor the impacts of meteorology and hydrology (e.g., temperature, wind speed/direction, precipitation, salinity, turbidity, current), or simulate physical sediment transport and/or carbon-removing sand redistribution.

In some cases, a sediment transport model may be used to predict and quantify physical behavior including and not limited to carbon-removing sand redistribution following placement in coastal environments, benefit to coastal construction, impact on the pre-placement coastal processes, physical weathering, vertical and horizontal sediment sorting, turbidity, and wave conditions.

In some cases, sediment transport, reaction-transport, regional ocean system models, and Earth system models may be coupled, integrated, or used iteratively to inform the following: selection of deployment sites, ideal carbon-removing sand and sand blend characteristics, deployment design, environmental impacts, impacts on ocean acidification, changes in alkalinity, nutrient availability, fate of trace metals, and atmospheric carbon dioxide removal. In some cases, models may be used to inform on additional properties and impacts related to weathering.

The present disclosure also provides software configured to calculate carbon dioxide consumption and to measure, record, and verify carbon removal. The software may be configured to determine carbon dioxide consumption and/or carbon removal based on one or more sensor readings, model outputs, and/or one or more input parameters. The one or more input parameters may relate to, for example, the physical or chemical properties of the carbon-removing sand used, the ratio of carbon-removing to non-carbon-removing sand, the location in which the carbon-removing sand is distributed, an amount of carbon-removing sand distributed to a target site, or the manner/configuration in which the carbon-removing sand is distributed (e.g., method of distribution, form of distribution, or spatial characteristics of the distribution). In some cases, the sensor readings may comprise measurements of alkalinity, DIC, pCO2, pH, salinity, conductivity, dissolved oxygen, nutrients, trace metals, organic carbon, water temperature, wave activity, currents, and/or additional chemical and physical properties.

Figure 12:
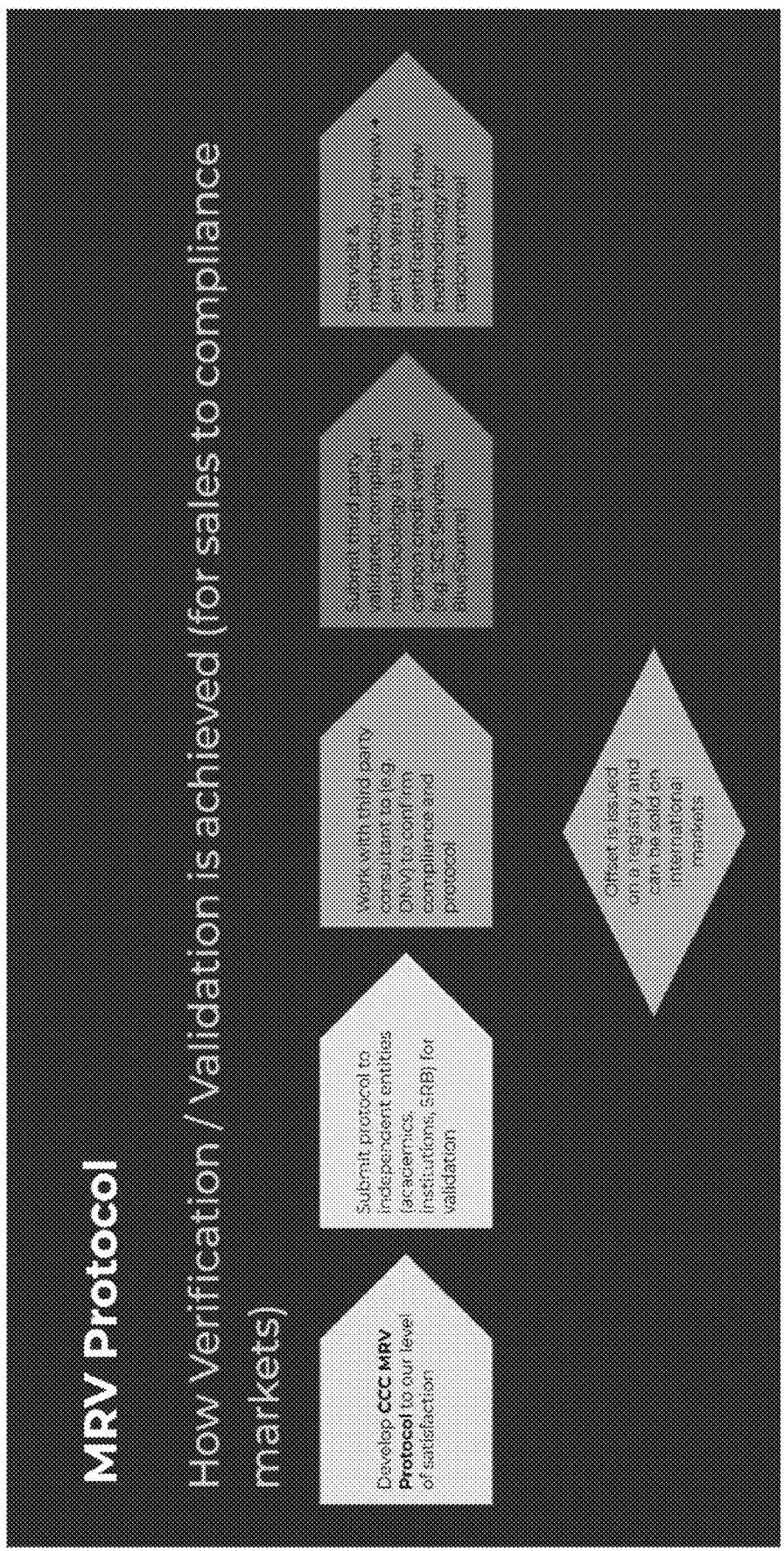
FIG. 12 schematically illustrates an exemplary protocol for measuring, recording, and verifying (MRV) carbon removal, in accordance with some embodiments.

In one aspect, the present disclosure provides methods and protocols for measuring, reporting, and verifying (MRV) carbon removal (e.g., by way of Coastal Carbon Capture using carbon-removing sand). Referring to FIG. 12, the protocols may be submitted to independent, third-party entities (e.g., academics, institutions, etc.) for validation. Once validated, the protocols may be implemented by an individual or an entity. Additional third-party entities may ensure and confirm compliance. The individuals or entities implementing the MRV protocols may then submit the third-party verified, compliant methodologies to a carbon credit verifier, and an offset or a credit may be issued on a registry for sale in domestic and/or international markets.

In a further aspect, the present disclosure provides a method and process for conducting low emission, carbon neutral or carbon negative coastal construction projects with respect to atmospheric greenhouse gas emissions. To achieve this, sediment used in a coastal resiliency project may be mixed with one or more types of carbon-removing sand, as described elsewhere herein and a life cycle analysis must be conducted on the project method and process.

Furthermore, the present disclosure provides a method and process for conducting low emission, carbon neutral or carbon negative dredging operations. The method and process of conducting dredging operations may be either net neutral or net negative with respect to atmospheric greenhouse gas emissions. To achieve this, dredged sediment may be mixed with one or more types of carbon-removing sand, as described elsewhere herein and a life cycle analysis must be conducted on the project method and process The methods and processes described herein may be adapted for any type of construction activity, including land-based construction activities, potentially rendering all of such activities low emission, carbon neutral, or carbon negative.

Whereas traditional dredging operations consume large quantities of fuel and emit correspondingly large quantities of greenhouse gasses, the method and process described here may allow dredging operations to be conducted in a way that is carbon neutral or even carbon negative over the lifetime of the project. This method and process provides significant advantages, allowing dredging operators to (i) mitigate carbon dioxide emissions on behalf of themselves or their clients, (ii) avoid emissions caps and taxes, and (iii) operate in jurisdictions which impose voluntary or involuntary restrictions on greenhouse gas emissions.

Figure 13:
FIG. 13 schematically illustrates a chemical reaction by which Coastal Carbon Capture occurs when olivine is introduced to a target site, in accordance with some embodiments.
Figure 14:
FIG. 14 schematically illustrates a chemical reaction by which Coastal Carbon Capture occurs when olivine is introduced to a target site, in accordance with some embodiments.
Figure 15:
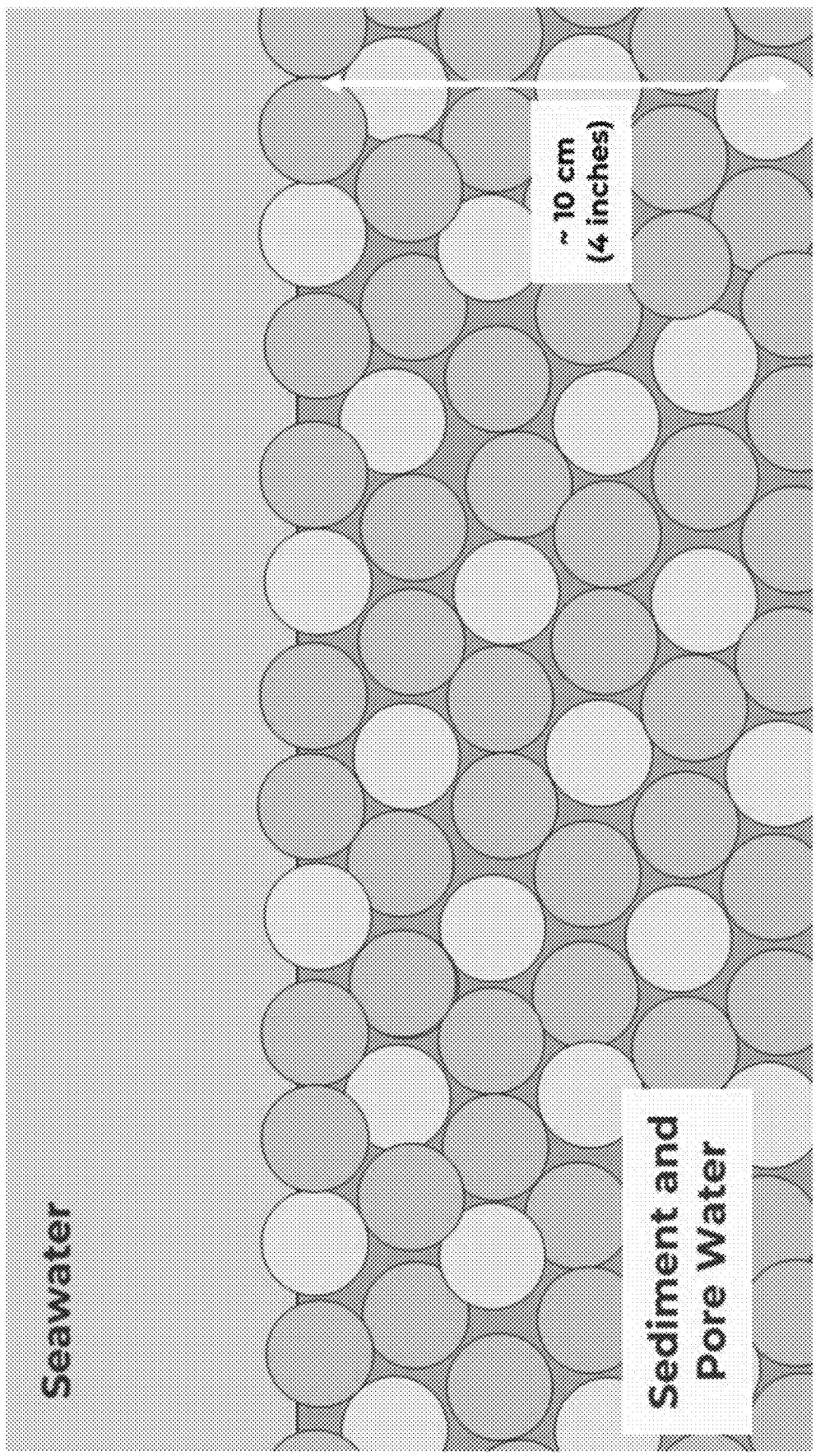
FIGS. 15-20 schematically illustrate an environment in which olivine can be introduced for coastal carbon capture, in accordance with some embodiments.
Figure 16:
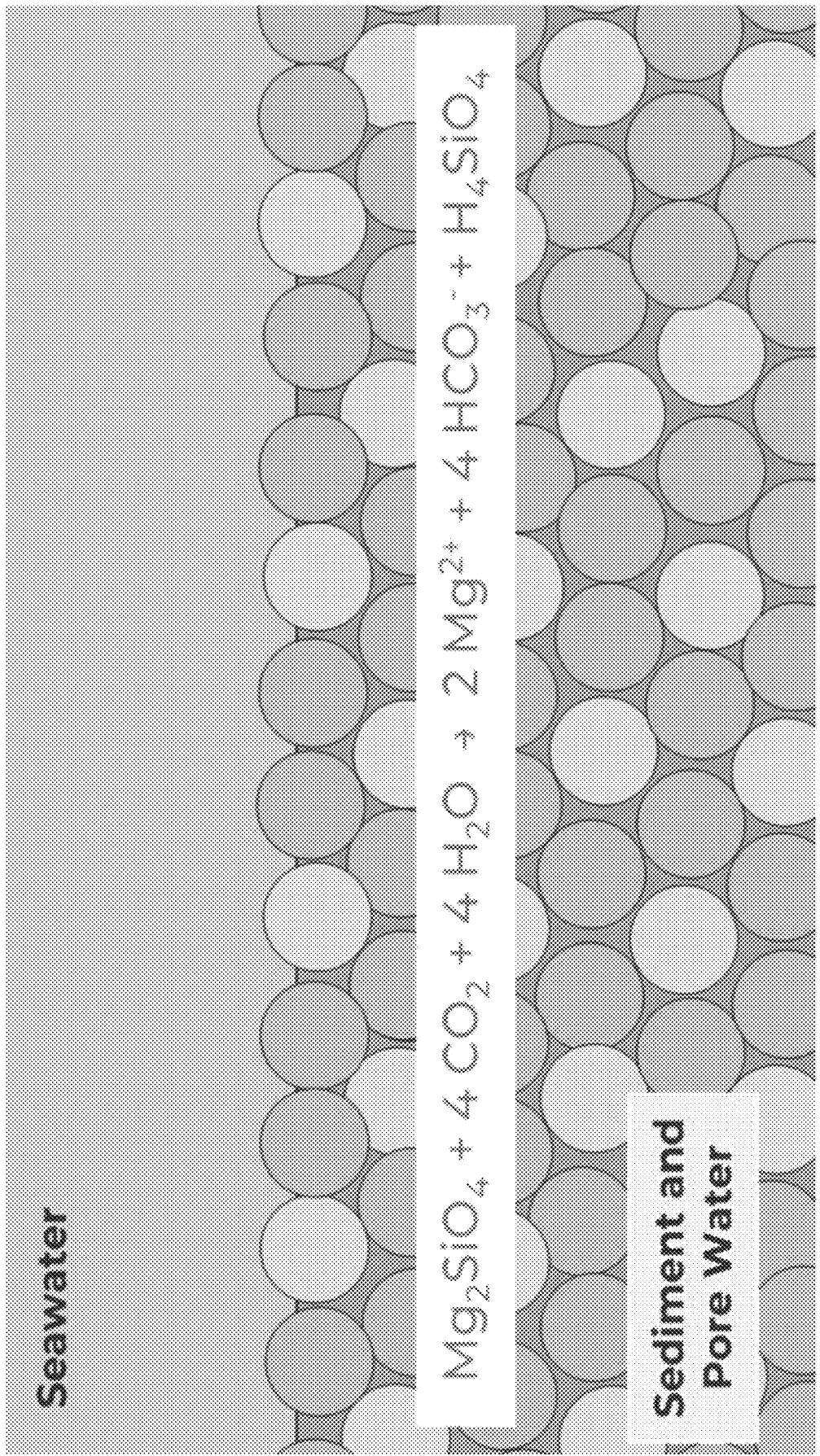
Figure 17:
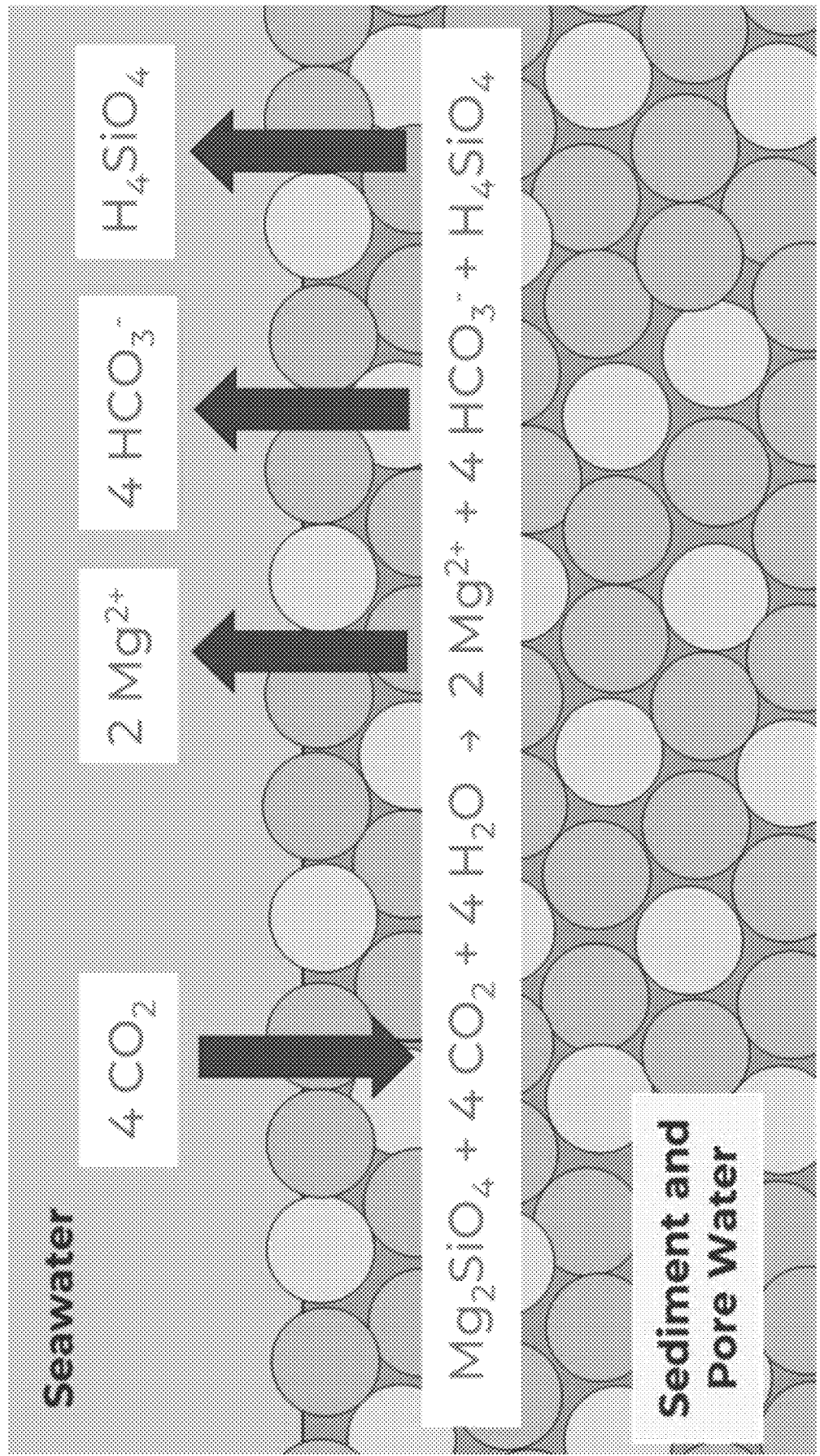
Figure 18:
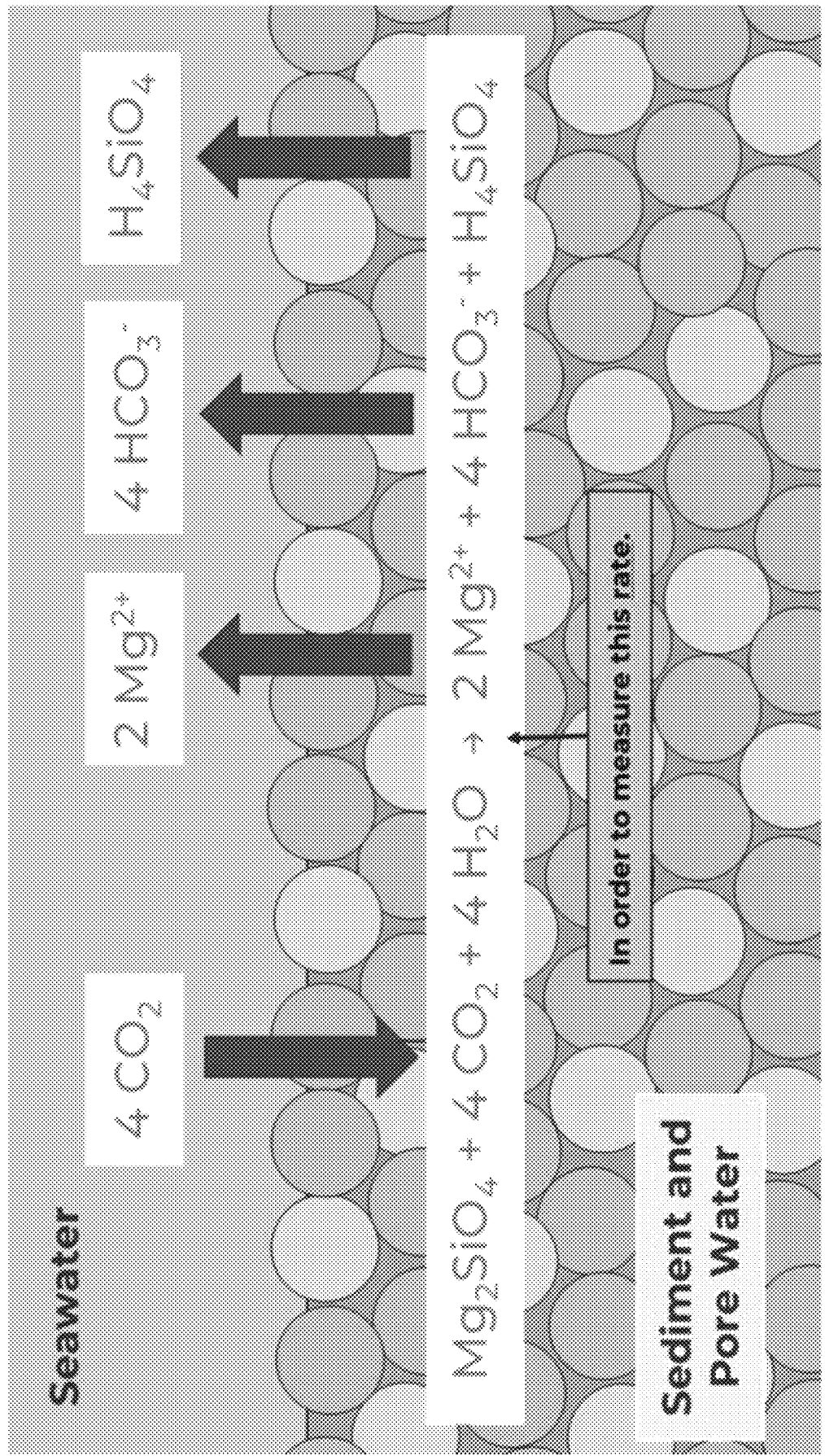
Figure 19:
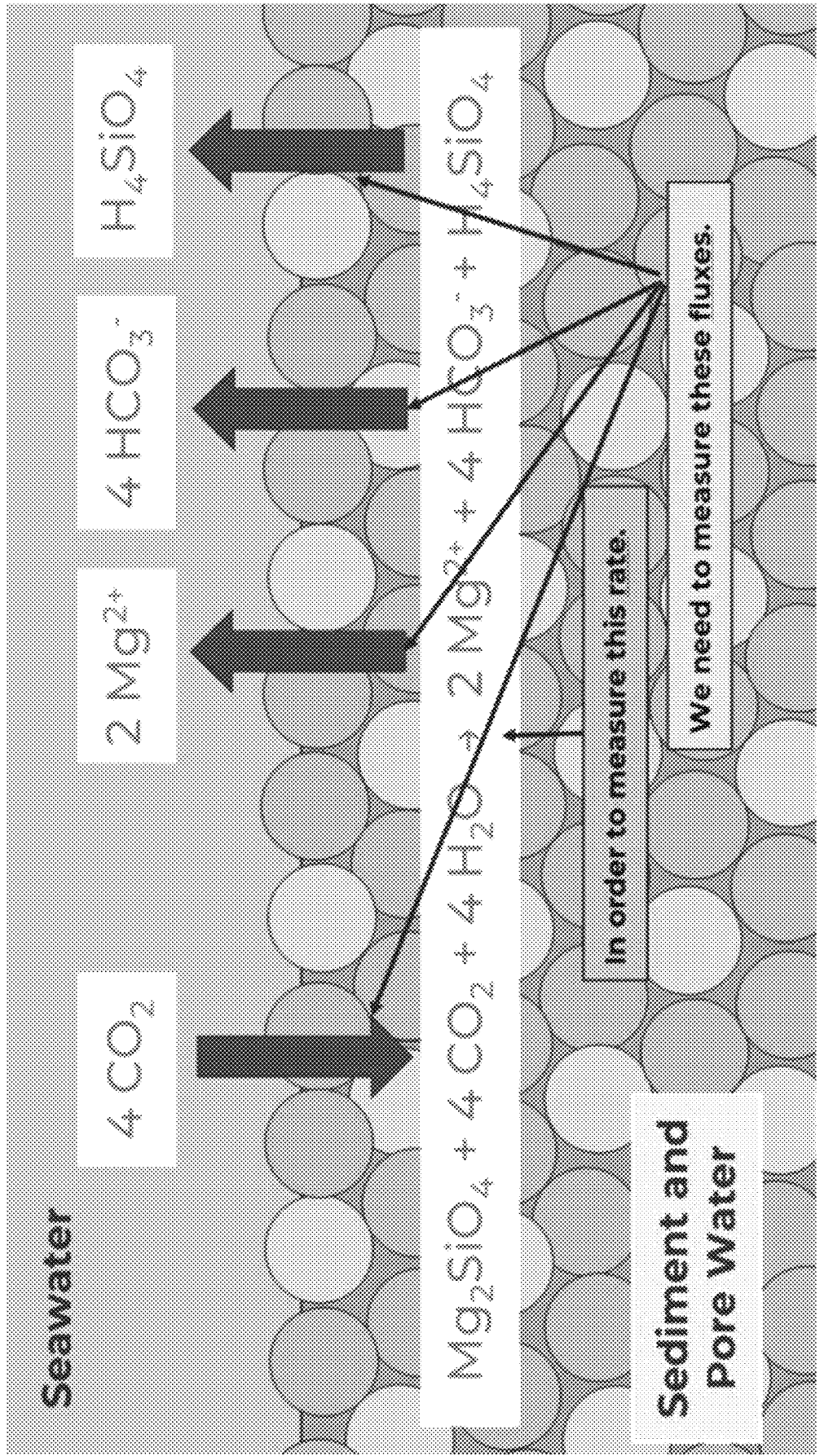
Figure 20:
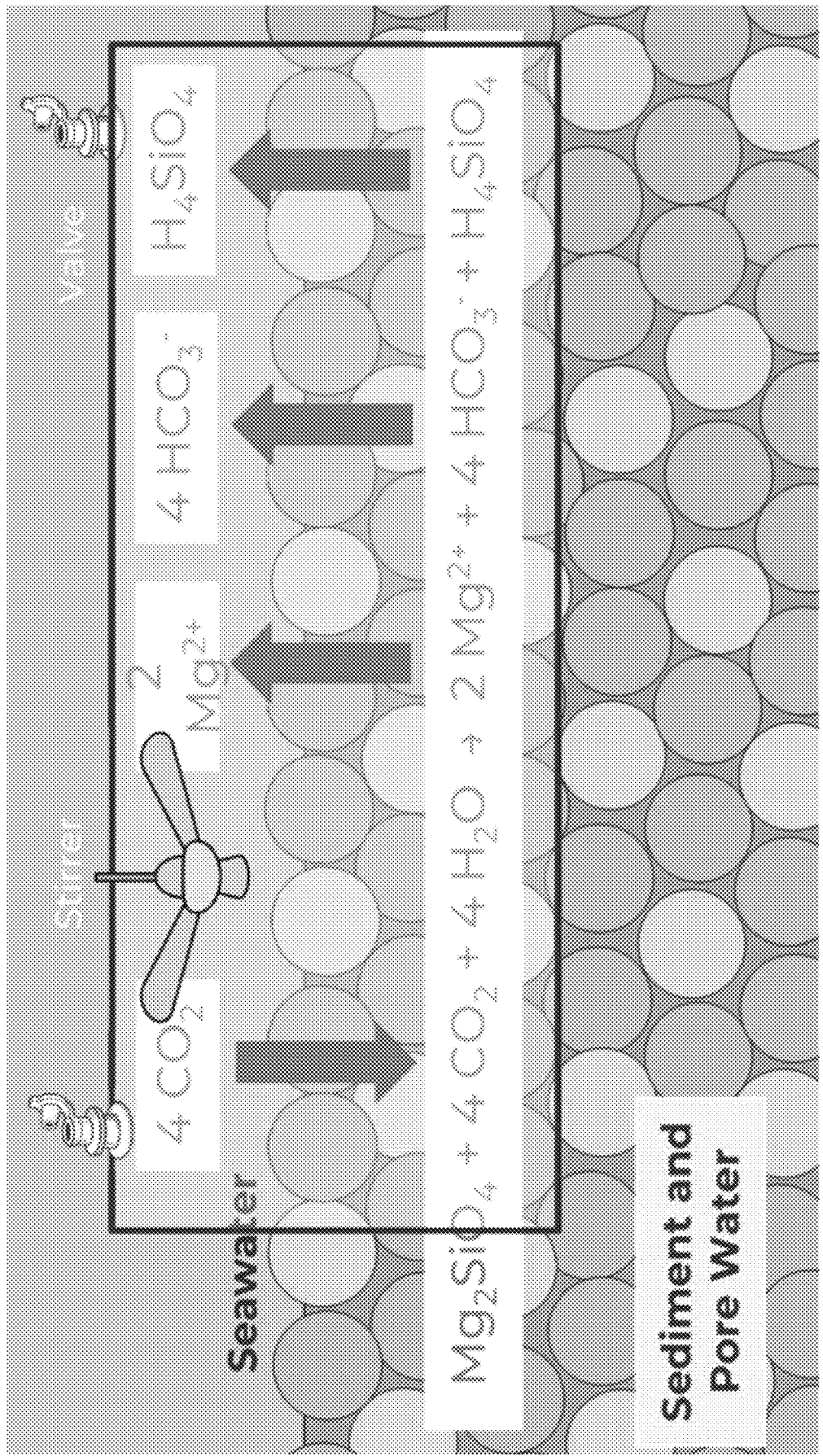

FIGS. 13-14 and FIG. 36 show a reaction representing the chemical mechanism by which Coastal Carbon Capture can occur when olivine is introduced to a target site as carbon-removing sand (e.g., by adding olivine sand to beaches and mixing the olivine sand with the native beach sand). Although the calculation would potentially be different for other carbon-removing sands, for every 1 mol of olivine (which olivine may comprise or exhibit any of the physical or chemical properties or compositions described herein), 4 mols of carbon dioxide may be consumed or captured, and 4 mols of an alkaline material (bicarbonate or $HCO_3^-$) may be generated.

FIGS. 15-20 show an environment comprising a first layer comprising seawater and a second layer comprising sediment and pore water. The sediment and pore water may span a dimension of about 10 centimeters (cm) or about 4 inches (in). The reactions shown in and described in relation to FIGS. 13-14 and FIG. 36 may drive the capture of carbon dioxide (e.g., carbon dioxide in the atmosphere or in the seawater) and the release of magnesium, bicarbonate, and silicic acid. The rate of the overall reaction may be determined based on the fluxes of chemical species associated with carbon dioxide capture and dissolution of alkaline material.

Figure 21:
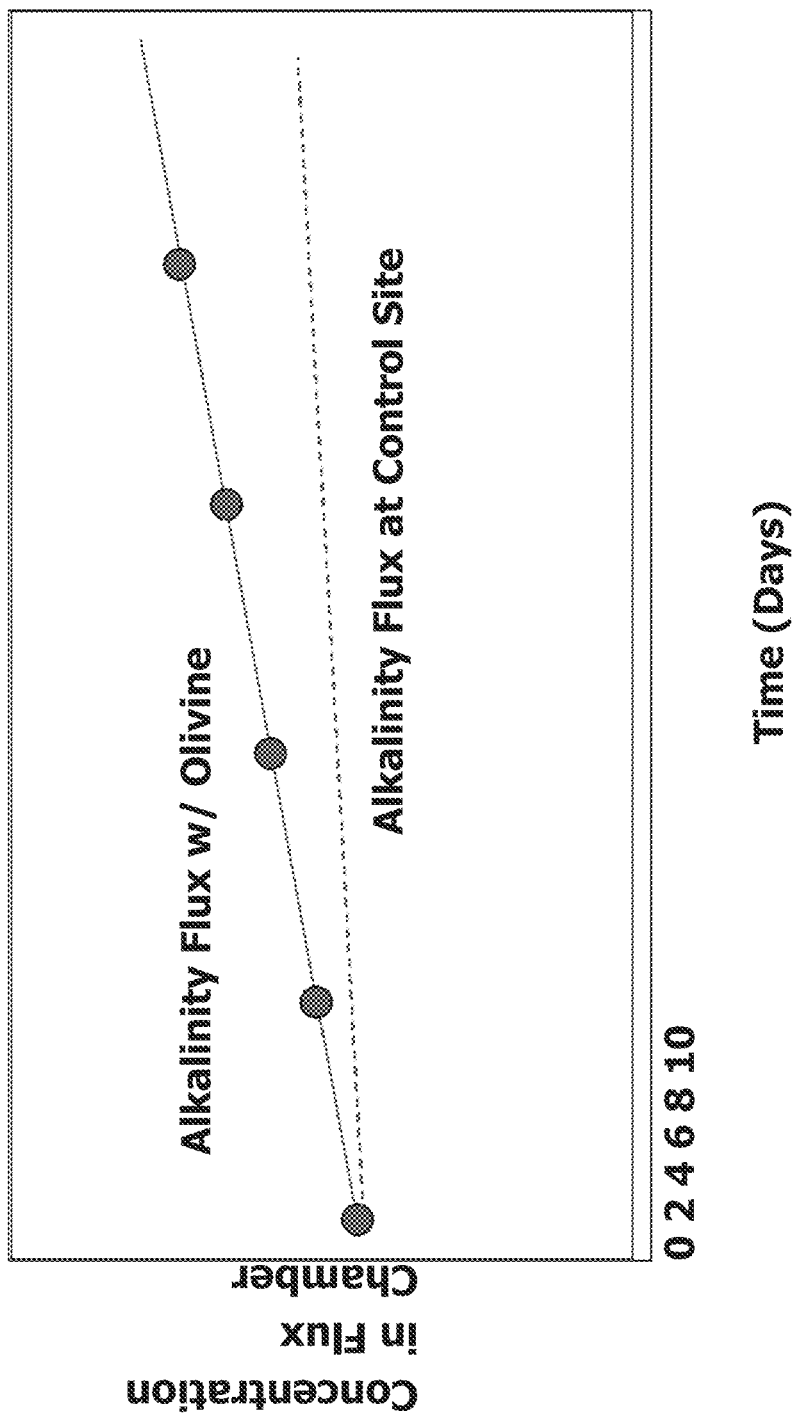
FIG. 21 schematically illustrates a plot of concentration of an alkaline material in a flux chamber as compared to a control site, as a function of time, in accordance with some embodiments.

FIG. 21 shows an overview of the porewater method for determining flux of an alkaline material that is produced. The porewater method may be based on Fick's first law of diffusion. The flux of the alkaline material may be determined based on a diffusion coefficient (representing area per unit time) and a dC/dZ value (representing a change in concentration or amount of substance per unit volume, as a function of position or dimensional length). With olivine present in porewater, a larger flux may be observed (steeper slope and bigger flux), whereas when olivine is not present, a smaller flux is observed (shallower slope and smaller flux).

Figure 22:
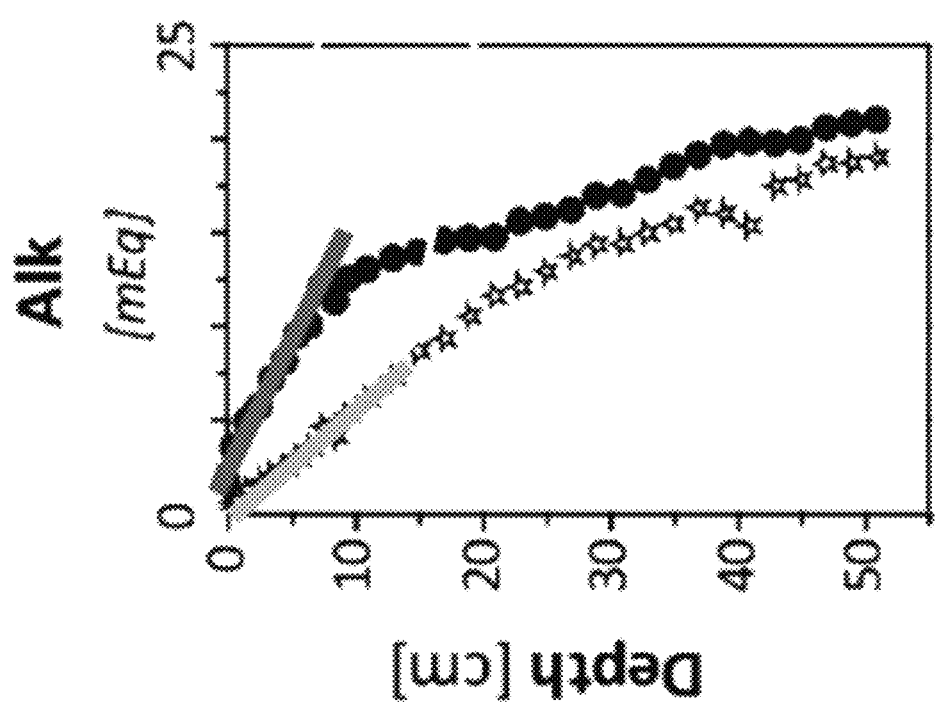
FIG. 22 schematically illustrates an overview of the porewater method, in accordance with some embodiments.

FIG. 22 shows a shrinking core model comprising a transformed volume and an untransformed volume of an exemplary olivine particle. The shrinking core model may be represented by $X=1-[1-R/(\rho*d))*t]^3$, where X is the fraction of olivine reacted, R is a function of pH and temperature, $\rho$ is molar density, d is starting diameter, and t represents time. One assumption for this model is that the particles are a perfect sphere.

Figure 23:
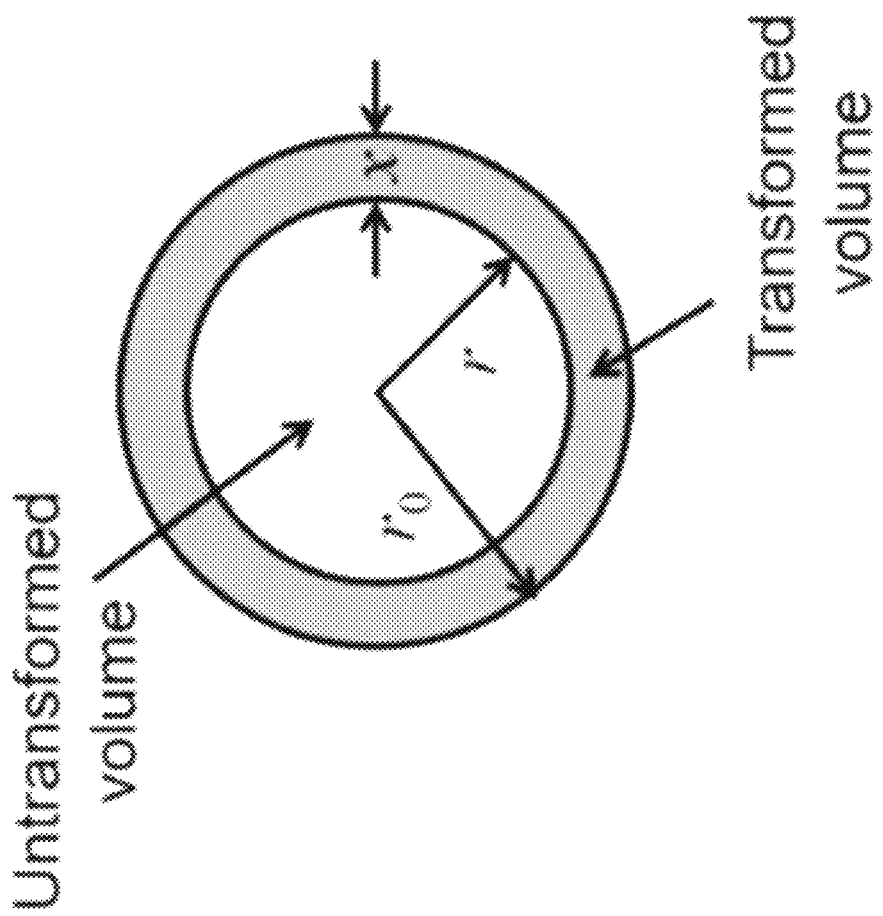
FIG. 23 schematically illustrates a shrinking core model, in accordance with some embodiments.

FIG. 23 shows dissolution rates for olivine having various grain sizes. The fraction of olivine weathered over time may increase more rapidly for olivine particles having smaller grain sizes. For example, for olivine with a 30 micrometer grain size, 10% of the olivine may weather within 3 years, 50% of the olivine may weather within 18 years, and 90% of the olivine may weather within 47 years. In contrast, for olivine with a 64 micrometer grain size, 10% of the olivine may weather within 6 years, 50% of the olivine may weather within 39 years, and 90% of the olivine may weather within 101 years. The rates shown generally correspond to static dissolution rates based on inorganic chemical processes and may not include acceleration of weathering due to wave energy and biotic processes.

Figure 24:
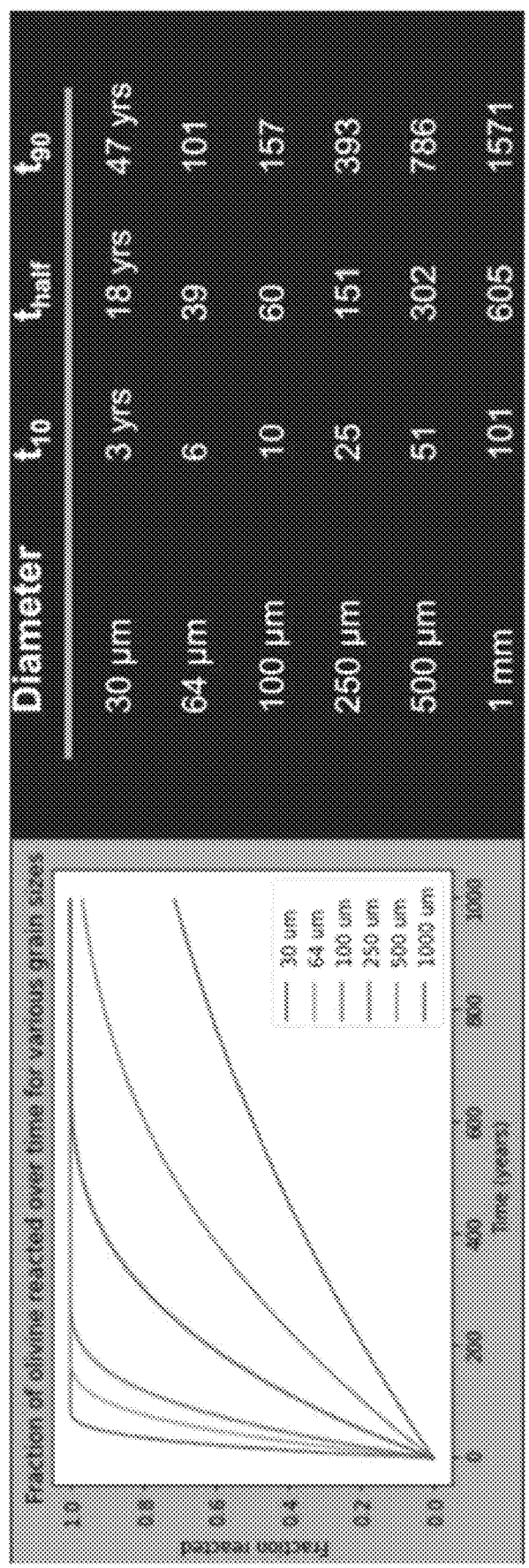
FIG. 24 schematically illustrates dissolution rates for olivine having various grain sizes, in accordance with some embodiments.

FIG. 24 shows an exemplary modeling approach for particle distribution. In one step, the modeling approach may comprise simulating grains to be compatible with a desired particle size distribution. The modeling approach may further comprise shrinking each particle over a time period (e.g., to simulate dissolution or erosion of one or more portions or layers of each particle), and thereafter summing the total mass of the particles and/or the total amount dissolved or eroded at various time points in order to determine the fraction of mass remaining as a function of time.

Figure 25:
FIG. 25 schematically illustrates an exemplary modeling approach for particle distribution, in accordance with some embodiments.

FIG. 25 shows dissolution rates for different mixtures of olivine having different mean grain sizes. In general, olivine mixtures with smaller mean grain sizes may have a shorter half-life (i.e., a shorter time period for half of the olivine mixture to dissolve under a particular set of conditions).

Figure 26:
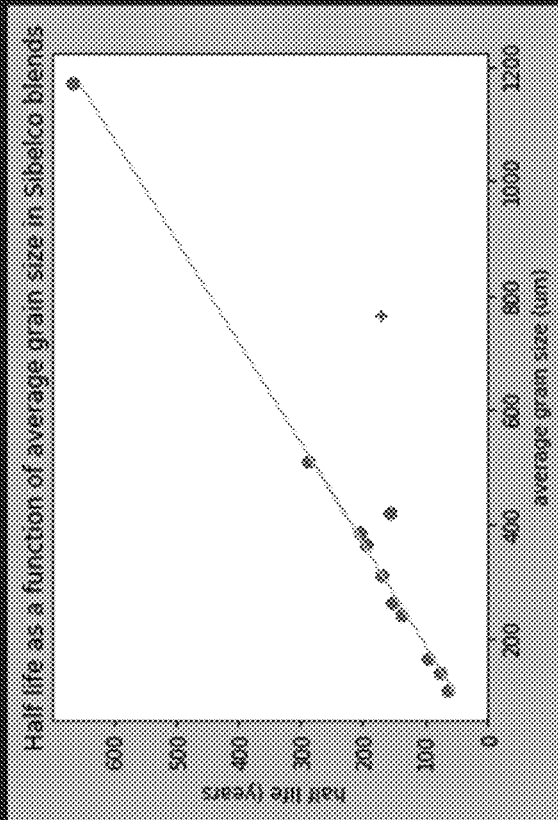
FIG. 26 schematically illustrates dissolution rates for different mixtures of olivine having different mean grain sizes, in accordance with some embodiments.

FIG. 26 shows the impact of temperature and pH on half-life. In some cases, the half-life for olivine dissolution may decrease as temperature increases. In some cases, the half-life for olivine dissolution may increase as pH increases. In some embodiments, the systems and methods disclosed herein may be implemented to optimize temperature and pH for dissolution environments to shorten the half-life for olivine dissolution. In other embodiments, the systems and methods disclosed herein may be implemented to identify candidate locations with optimal temperature and pH for olivine dissolution environments to shorten the half-life for olivine dissolution.

The systems and methods disclosed herein may be configured or implemented to overcome challenges relating to spatial and temporal heterogeneity, low signal/noise ratios of key parameters for MRV due to slow dissolution of olivine, and variation in secondary mineral product generation. The systems and methods disclosed herein may also help to overcome verification challenges such as, for example, objective criteria for acceptance and verification of carbon credit sales, and how to influence such criteria to adapt them to coastal weathering processes.

The present disclosure provides methods for performing MRV (i.e., the measurement, reporting, and verification) of carbon capture and/or olivine dissolution. In some cases, the methods may comprise establishing a treatment site and a reference or baseline site. The methods may further comprise measuring alkalinity fluxes and/or other parameters at a network of discrete locations. In some cases, this may be repeated over time as olivine dissolves. The methods may further comprise interpolating over time and space to determine an overall carbon removal and/or dissolution rate across an area or a volume of the site. In some cases, the overall carbon removal and/or dissolution rate across the site may be determined in part using a numerical reaction-transport model that provides a fit to the measured data. In some cases, the overall carbon removal and/or dissolution rate across the site may be determined in part using a sediment transport model that indicates the location and concentration of carbon-removing sand through time and space.

Figure 27:
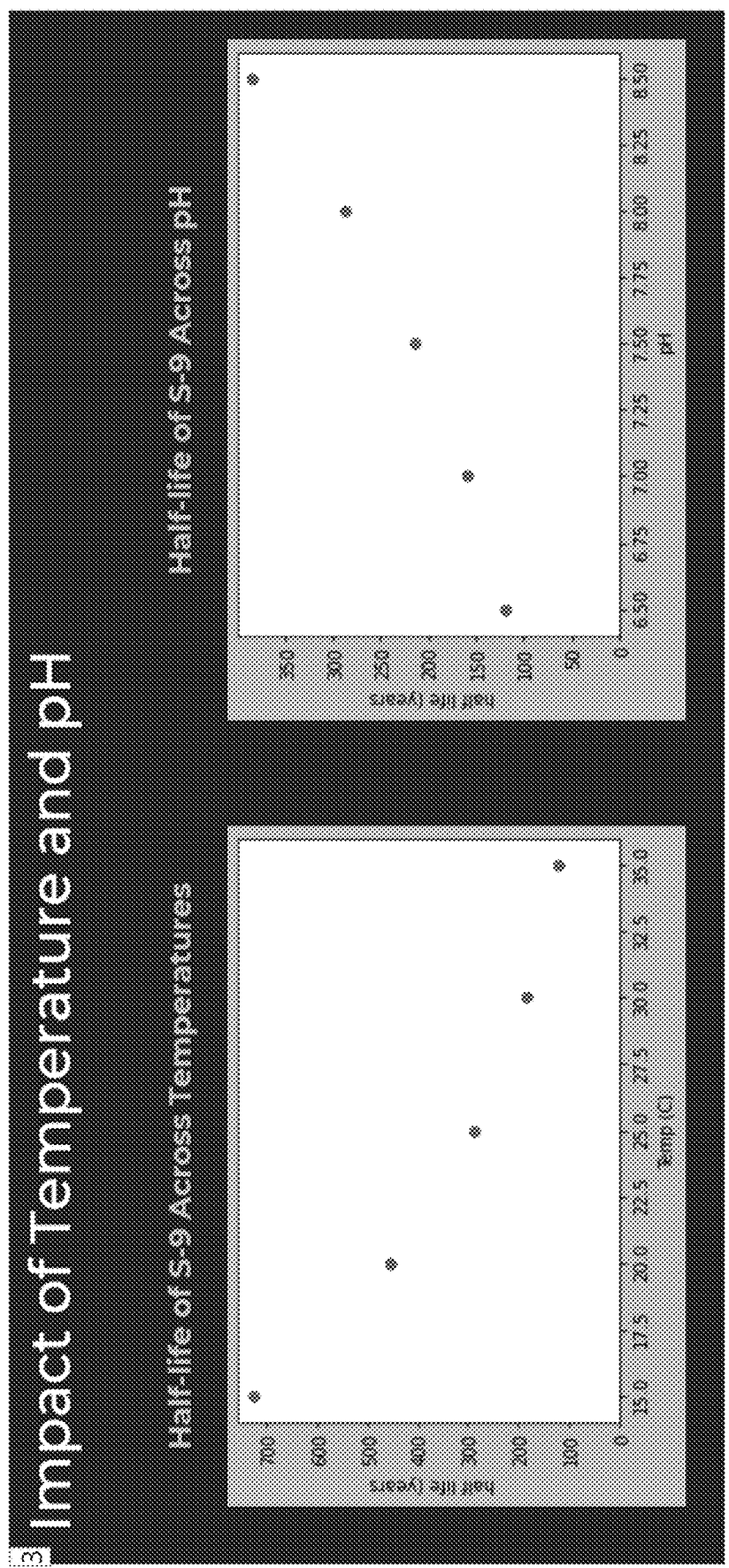
FIG. 27 schematically illustrates the impact of temperature and pH on olivine half-life, in accordance with some embodiments.

FIG. 27 shows examples of temporal factors and spatial factors that can vary for coastal ecosystems, many of which are extremely dynamic. Temporal factors may include, for example, diurnal factors (i.e., day/night variations), tides, seasonality, temperature, weather, and/or waves. Spatial factors may include, for example, position and hydrodynamics, depth, tides, sediment type, grain size, sediment organic carbon content, and/or bottom cover (e.g., sea grass, rocks, coral, etc.).

In some cases, the methods disclosed herein may comprise assessing or evaluating temporal heterogeneity by measuring—for example—depth, temperature, salinity, pH, turbidity, chlorophyll concentrations, and/or dissolved oxygen concentrations over time. FIG. 28 shows plots of temporal heterogeneity of various characteristics for a target site, including depth, salinity, turbidity, temperature, dissolved oxygen, and pH. In some cases, the target site for olivine distribution and dissolution may be chosen based on temporal heterogeneity relative to other candidate or baseline/reference sites.

Figure 29:
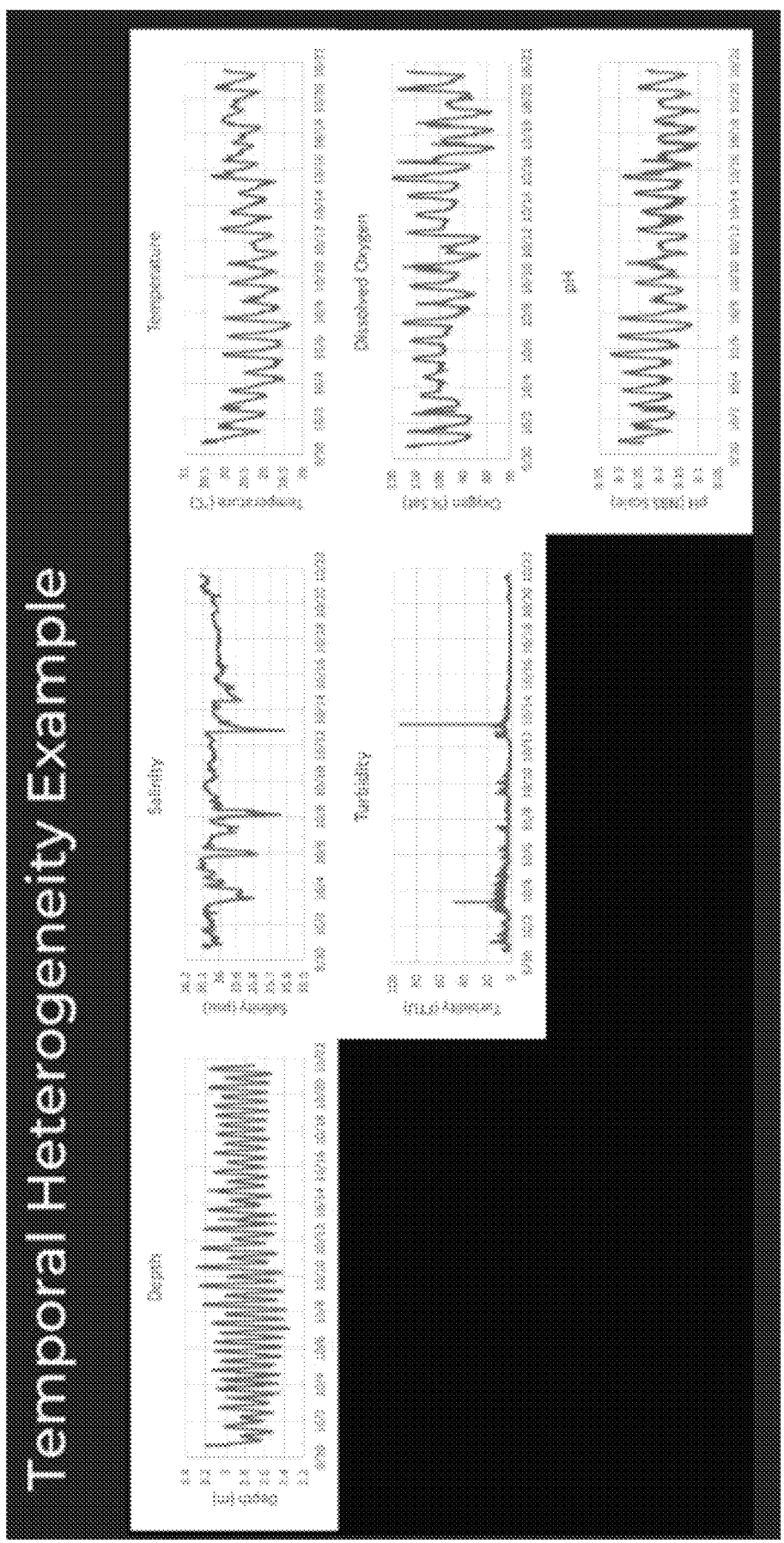
FIG. 29 schematically illustrates plots of the temporal heterogeneity of various characteristics for a target site, in accordance with some embodiments.
Figure 30:
FIGS. 30-32 schematically illustrate examples of factors to consider when calculating alkalinity fluxes, in accordance with some embodiments.
Figure 31:
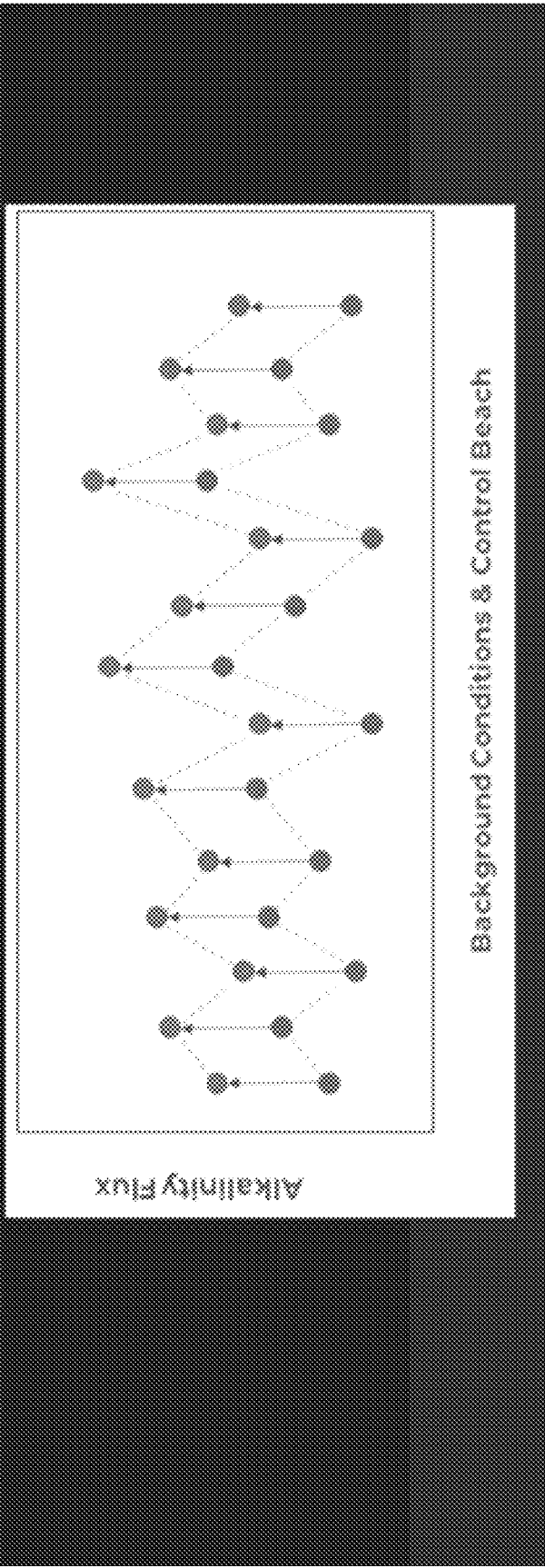

As shown in FIGS. 29-31, in some cases, the methods disclosed herein may comprise calculating alkalinity fluxes and measuring dissolution rates of olivine to secure carbon credits. Alkalinity fluxes induced by olivine may be determined by discerning changes in alkalinity fluxes due to olivine from other natural background fluxes. In some cases, other fluxes attributable to olivine, such as dissolved inorganic carbon (DIC) fluxes and fluxes of pCO2, may be determined based on a comparison of measured fluxes to natural background fluxes. The fluxes attributable to olivine dissolution and/or the natural background fluxes may be space and time dependent. Such variations over space and time may be simulated, modeled, tracked, and/or measured to ensure accurate calculation of fluxes attributable to olivine, as opposed to natural background fluxes.

Figure 32:
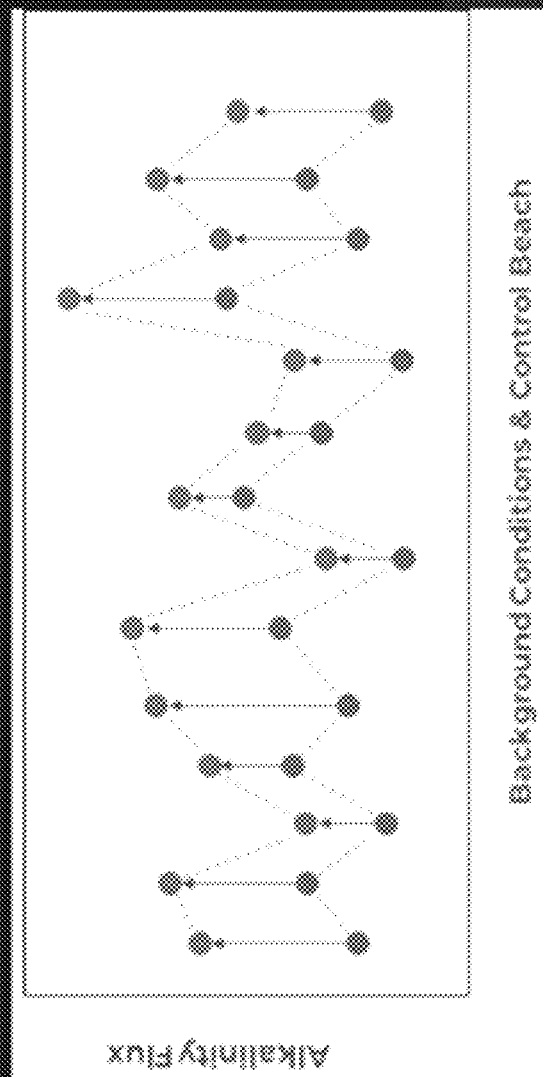

In another aspect, the present disclosure provides various methods for accounting for heterogeneity for MRV. FIG. 32 shows a summary of the MRV approaches described below at different scales of cost and complexity. These methods may be used independently, combined, or all used.

Approach 1—In some cases, the methods may involve using the shrinking core model described elsewhere herein for an approximate rate of dissolution. The dissolution rate and carbon dioxide/carbon-removing sand ratio may be assumed or approximated.

Approach 2—Alternatively, mesocosm experiments may be utilized to determine regional olivine dissolution rates. Further, this approach may be initially tested using a sealed, recirculating design that is configured to maintain and control spatiotemporal heterogeneity and further allow for temperature and/or lighting control.

In cases where olivine is deployed in a target site (e.g., a mesocosm or the natural environment), olivine tracers may be used to track olivine dissolution in order to model and refine in situ weathering rates.

The present disclosure provides systems and methods to track the movement of olivine grains in a target site. The systems and methods of the present disclosure may be implemented to track olivine transport in a target site based on or using, for example, trace metal content, fluorescent dyes, and/or olivine-specific spectral properties. This may be a relatively inexpensive process that can be set up prior to obtaining regulatory permits.

Approach 3—In some cases, the mesocosm-based approaches described herein may be augmented with field data (e.g., obtained in-situ manually or automatically using one or more sensors or ex-situ through the extraction of representative field samples). The data obtained using the one or more sensors (which one or more sensors may comprise any of the sensors described herein or any other sensors for obtaining any of the measurements referred to herein) may provide additional information to better quantify and track spatial and/or temporal variations in environmental conditions or parameters relating to olivine dissolution and Coastal Carbon Capture.

Approach 4—In some cases, field-based approaches may be solely used to obtain field data (e.g., in situ data obtained in-situ manually or automatically using one or more sensors or ex-situ through the extraction of representative field samples). The data obtained using the one or more sensors (which one or more sensors may comprise any of the sensors described herein or any other sensors for obtaining any of the measurements referred to herein) may provide sufficient information to quantify olivine dissolution, carbon removal, sediment transport, and track spatial and/or temporal variations in environmental conditions or parameters relating to olivine dissolution and Coastal Carbon Capture.

Approach 5—In some cases, a numerical model may be constructed that allows for accurate simulation of spatial and temporal variations in background fluxes and olivine dissolution rates. This can help to correct for time and space dependent variations, and allow for the use of sparse observations or other information or data at discrete points (e.g., points in time and/or points in space) to calibrate, verify, and validate the model. The model may be built and implemented for one or more a priori simulations.

In cases where olivine is deployed in the natural environment, olivine tracers may be used to track olivine dissolution in order to estimate, predict, model, and refine in situ weathering rates.

The present disclosure provides systems and methods for tracking the movement or transport of olivine grains in the natural environment (e.g., in a target site in which the olivine is provided or introduced). The systems and methods of the present disclosure may be implemented to track olivine transport based on or using, for example, trace metal content, fluorescent dyes, and/or olivine-specific spectral properties. The trace metal content, the movement or dispersion of fluorescent dyes, and/or the olivine-specific spectral properties may be detected and tracked using any of the sensors described herein.

FIG. 33 illustrates various examples of reaction-transport modeling studies that may be used to simulate sediment porewater profiles, solid-phase chemistry, and benthic fluxes. The simulations and studies may be tailored to project requirements, and can take into account secondary mineral formation and trace metal speciation and cycling. The plots shown in FIG. 33 illustrate an exemplary numerical simulation of an alkalinity profile and the effects of spreading a 2 centimeter (cm) thick layer of pure olivine sand on beach sediment. In some cases, the alkalinity flux across the sediment-water interface may be monitored by (1) constructing biogeochemical models of olivine dissolution in sediments, (2) validating model performance using field measurements of sediment-water alkalinity flux (and other carbonate parameters), and (3) calculating carbon dioxide capture, storage, or sequestration (by weight or volume) based on the thermodynamics of air-sea carbon dioxide exchange and known behavior of the marine carbonate system.

Figure 34:
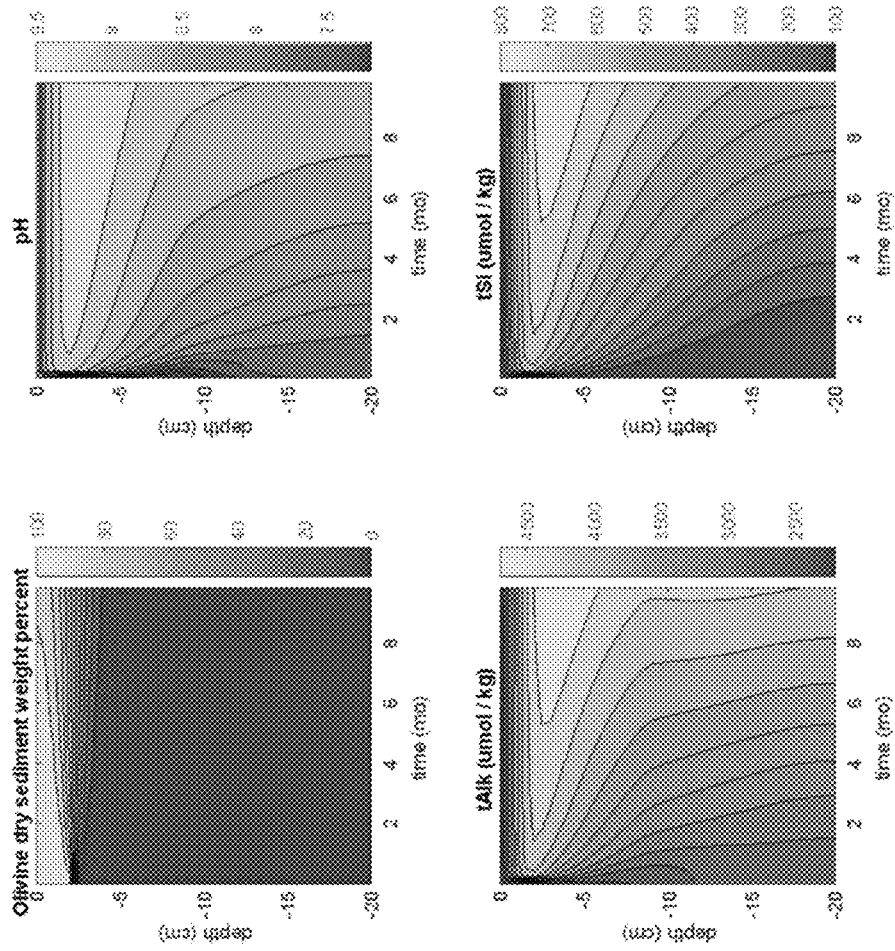
FIG. 34 schematically illustrates various reaction-transport modeling studies that may be used to simulate sediment porewater profiles, solid-phase chemistry, and benthic fluxes, in accordance with some embodiments.

The systems and methods disclosed herein may be implemented using one or more sensors capable of measuring at optimal spatial and temporal resolutions. As used herein, sensors may refer to sensors capable of remote sensing (including via buoys and for use in drone surveys, etc.), benchtop sensors (i.e., traditional analytical equipment) and other sensors. The sensors may obviate the need to use traditional, manual geochemical methods, which require labor intensive field sampling and returning of samples to labs for analysis and can involve significant costs. FIG. 34 shows various examples of sensors that can be used for MRV, including sensors configured to measure temperature, salinity, pH, pCO2, DIC, alkalinity, redox, and/or wave impacts on sand. In some cases, a solid state sensor for simultaneous measurement of total alkalinity and pH of seawater (including seawater that does or does not comprise olivine) may be used. In some embodiments, a plurality of sensors for MRV may be deployed in a single system. In other embodiments, a plurality of sensors for MRV may be deployed in multiple separate systems. Additional examples of sensors are shown in FIG. 35, including silicate sensors, alkalinity sensors, CTDO sensors, Cytochips, dissolved inorganic carbon sensors, and nitrate sensors. In some cases, a $^{29}Si$ isotopic tracer can be used to track olivine dissolution and simultaneous precipitation of secondary clays and carbonate phases. This can allow separation and tracking of total versus net silicate dissolution.

In some cases, the impacts of physical wave-driven weathering on beach sand and olivine dissolution may be measured or simulated. In some cases, this may involve measuring and analyzing 2-phase (i.e., sand-water) flow in the benthic boundary layer of a breaking wave. This may be modeled numerically or physically (e.g., using wave tanks). In some cases, specialized sensors for measuring turbulent energy dissipation (e.g., in a lab or directly on a beach) may be utilized to measure impacts of physical wave-driven weathering.

Figure 37:
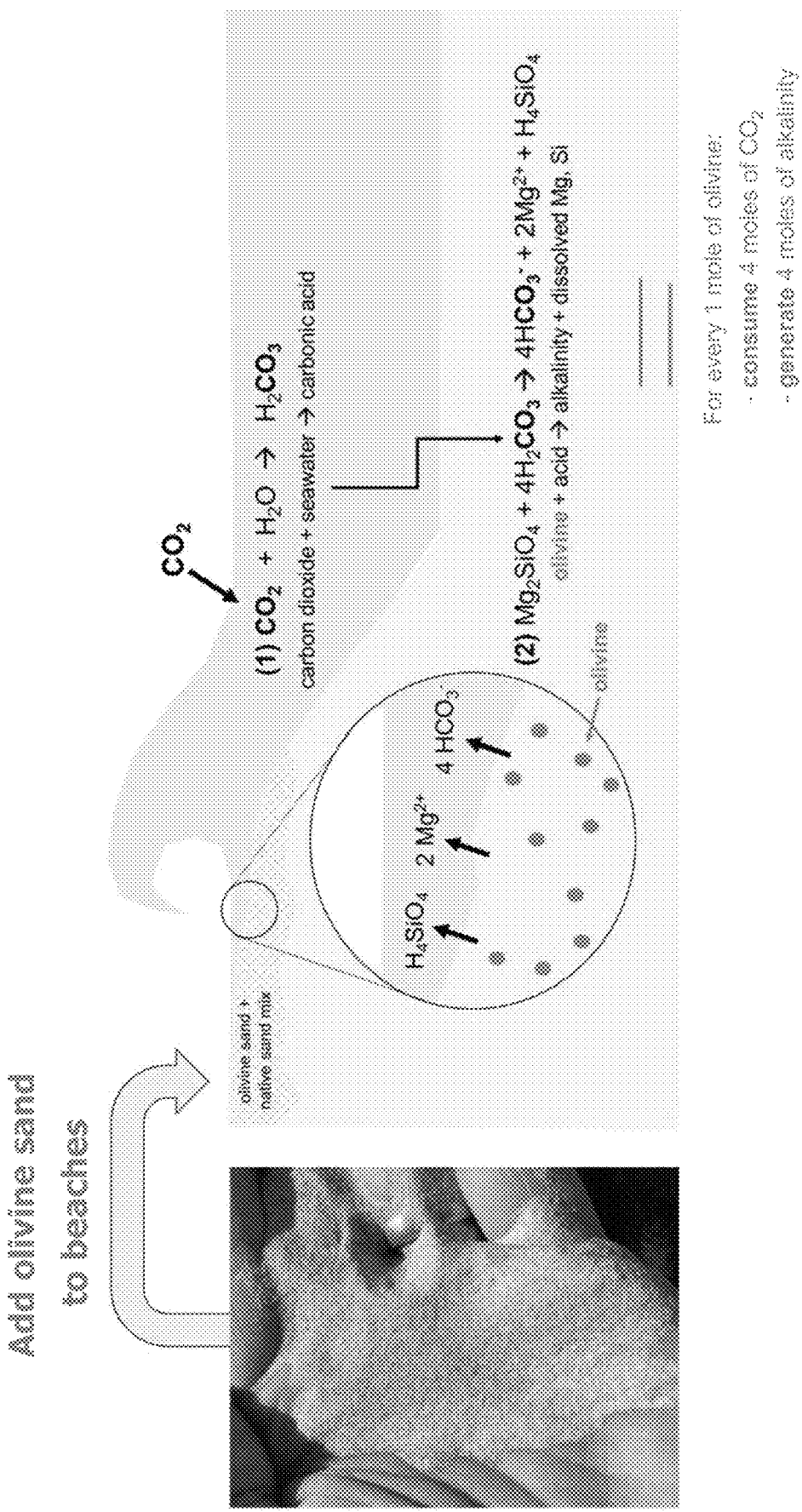
FIGS. 37-38 schematically illustrate reactions that may occur when olivine sand is introduced to beaches, in accordance with some embodiments.

FIG. 37 illustrates an approach to measuring carbon dioxide removal that is enabled by way of the reactions shown in FIG. 36. In some cases, it may not be feasible to monitor the air to sea carbon dioxide flux. Measuring air-sea carbon dioxide fluxes can be challenging because the olivine dissolution signal is strongly muted by dilution with open ocean seawater. Measuring net carbon dioxide flux can also be complicated by extreme seasonal and diurnal variations in $\Delta pCO2_{air-sea}$ due to changes in local photosynthesis and respiration. Accordingly, in some embodiments, the systems and methods disclosed herein may be implemented to monitor alkalinity flux across the sediment-water interface.

In some cases, the models described herein (models which may be generated for specific sites) may undergo stages of testing, including validation. Such validation may involve evaluating the following datasets: topobathymetry, geomorphological or geological features and their characteristics, hydrodynamic conditions, sediment transport, weather, olivine abundance, spatial distribution or olivine, non-olivine material and native sediments, and/or dissolution rates at one or more reference points in space and/or time. In some cases, the reference points may be arranged in a grid pattern. Validation may further involve validating measured and modeled alkalinity fluxes and olivine dissolution at reference points, and calculating alkalinity flux for a region or a project based on (i) a known mass or volume of olivine deployed and (ii) validated site-specific modeling. The models may be validated using one or more sensor measurements as described elsewhere herein. In some cases, models may be validated using data from microcosms, mesocosms, and benthic flux chambers deployed at or emulating the field conditions where olivine is deployed. Once validated, the models may be used to determine or predict olivine transport, olivine dissolution, reaction fluxes, and/or carbon sequestration. In some cases, the models may be updated or refined based on additional sensor measurements captured over a period of time, or additional data from field or lab experiments.

Figure 38:
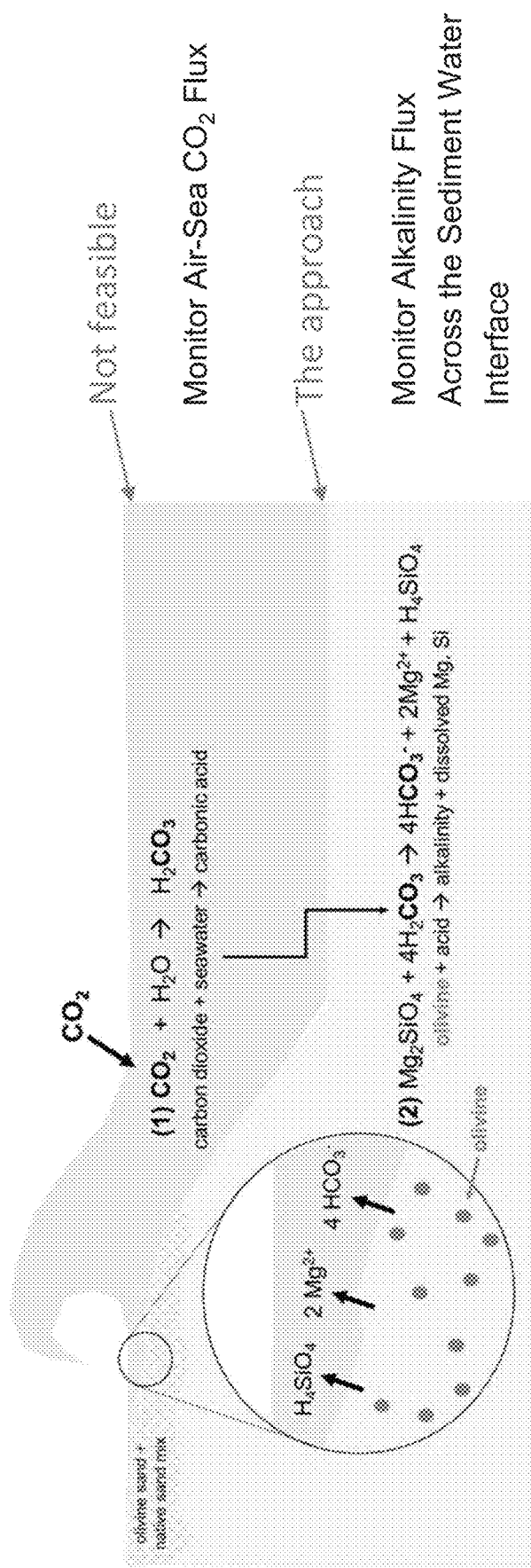

FIG. 38 illustrates an approach to calculating carbon dioxide sequestration from alkalinity flux based on an expression of how water DIC storage changes as a function of increasing alkalinity. Seawater carbonate chemistry may be controlled by pCO2, pH, DIC, and alkalinity. An isocapnic quotient may be computed based on a change in alkalinity relative to a change in DIC, at fixed conditions for pCO2, temperature, and salinity. In some cases, a 1 micromol increase in alkalinity may yield a 0.78-0.93 micromol DIC increase, which means that for every one ton of forsterite provided to a target site, 0.97 to 1.16 tons of carbon dioxide can be stored as marine DIC.

FIG. 39 illustrates a plot showing seawater age and the depth below sea water level of the Atlantic Ocean as a function of latitude (degrees North). Carbon dioxide capture via ocean alkalinization requires that the enhanced alkalinity water mass achieves equilibrium with atmospheric pCO2. The precise timescale for pCO2 equilibrium (~4 months) and DIC adjustment (~4 years) depends on the Revelle factor. The time scale for air-sea equilibration is considerably shorter than the time scale for olivine dissolution (~10-100 years) and approximately similar to the transit time distribution of mixed layer and subtropical mode water (~10-40 years). This means that the surface DIC reservoir can achieve quasi-steady equilibrium throughout equatorial and subtropical regions, making them the most suitable for coastal enhanced weathering.

Life Cycle Analysis

Once deployed on a beach, carbon-removing sand can capture 20 times more carbon than is emitted in the mining, milling, shipping, and underling coastal project. 1 ton of carbon-removing sand can capture up to 1.25 tons of carbon in ideal situations. Since it takes carbon-removing sand several decades to weather, it can provide effective coastal protection during long-term beach nourishment cycles.

The LCA assesses the net carbon removal of a carbon-removal project and encompasses both a quantification of carbon removal through the placement of carbon-removing sand as well as the carbon dioxide or carbon dioxide-equivalent emissions incurred by the placement. The gross carbon dioxide removal for a project will primarily be a function of the: precise mineralogy of the carbon-removing sand (e.g. Mg:Fe ratio in olivine), purity of carbon-removing sand source (e.g. olivine to pyroxene ratios), local seawater chemistry conditions, grain size of the carbon-removing sand, local seawater circulation patterns, and extent of secondary mineral precipitation following placement of the carbon-removing sand. The gross carbon dioxide emissions may comprise emissions associated with mining and/or extracting olivine, grinding the olivine to required grain sizes, transporting the olivine to one or more target sites, and spreading the olivine at the target sites and conducting monitoring for MRV purposes.

Figure 40:
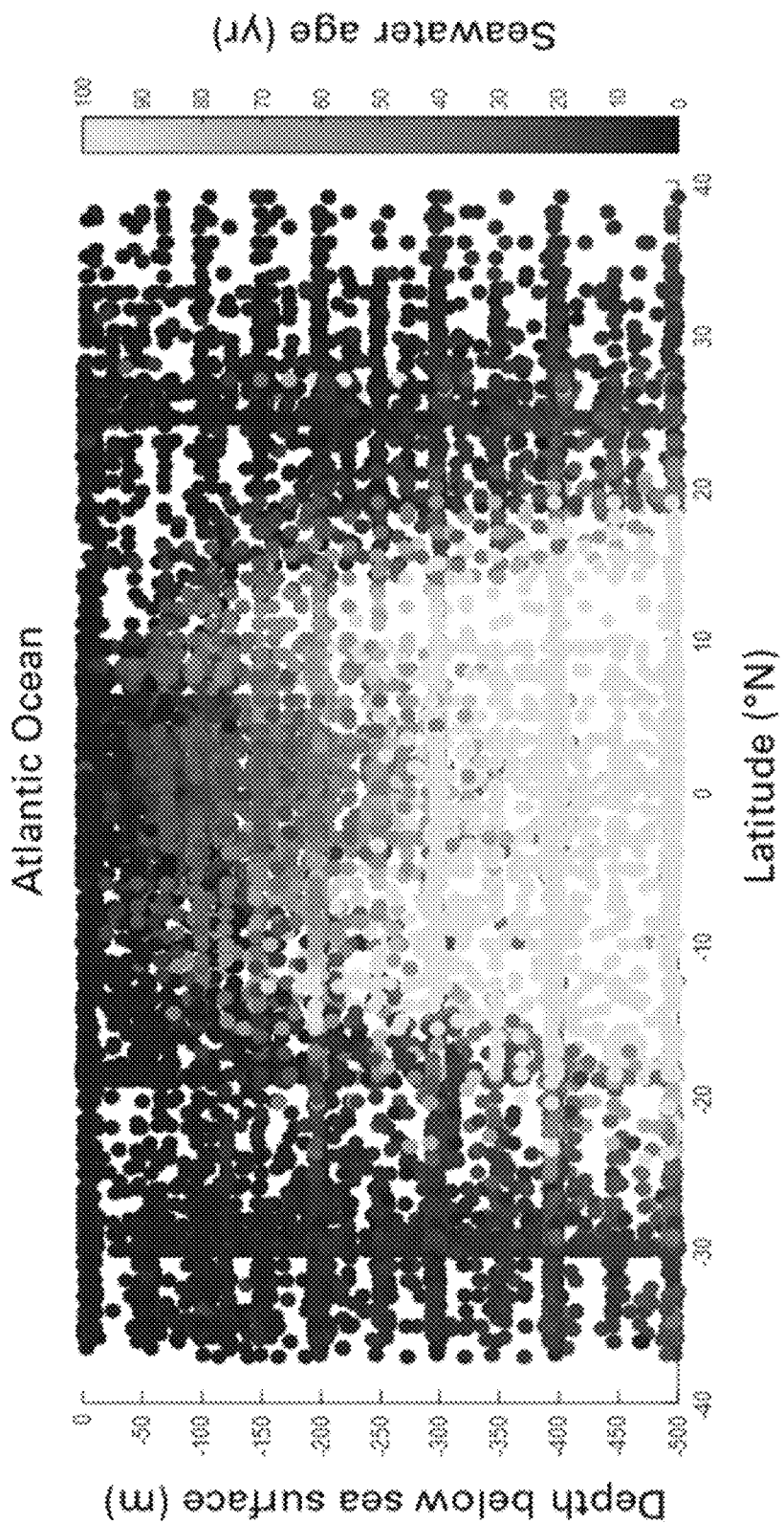
FIG. 40 schematically illustrates a plot showing seawater age and the depth below sea water level of the Atlantic Ocean as a function of latitude (degrees North), in accordance with some embodiments.

FIG. 40 illustrates an exemplary Coastal Carbon Capture life cycle analysis. The life cycle may comprise mining and/or extracting olivine, grinding the olivine to required grain sizes, transporting the olivine to one or more target sites, and spreading the olivine at the target sites. In some cases, the life cycle may be at least about 89% efficient, and can enable sequestration of at least about 5 to 20 times more carbon dioxide than the amount of carbon dioxide emitted during mining, grinding, transportation, and/or spreading of olivine.

Figure 41:
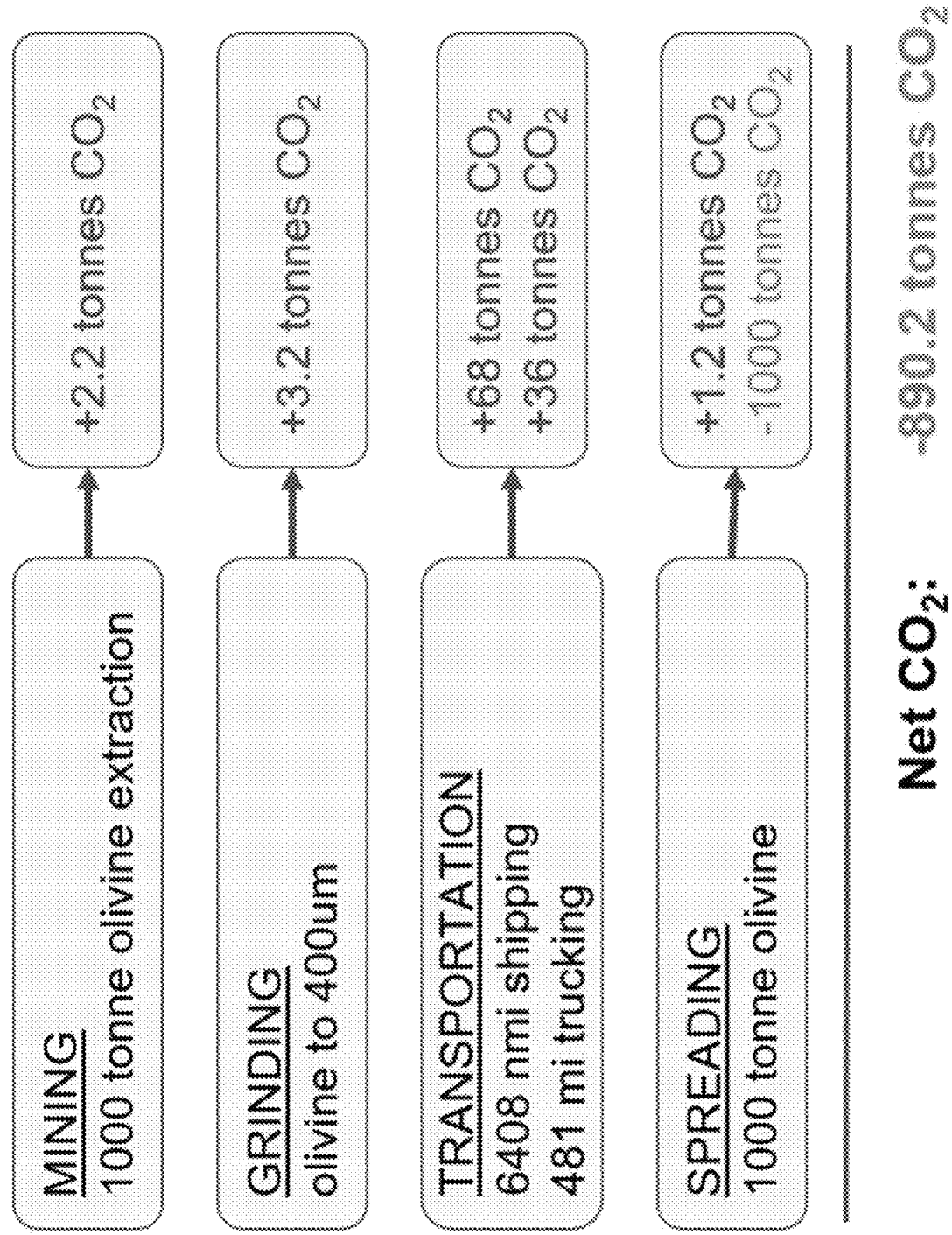
FIG. 41 schematically illustrates an exemplary coastal carbon capture life cycle analysis, in accordance with some embodiments.

FIG. 41 illustrates an example of a carbon payback period that can be realized using the methods and systems disclosed herein. In some cases, the break even payback period may occur at approximately 4 years, assuming the following: Grain Size: LE45 (d50: 365 μm); Temp: 25° C.; pH: 8; Embedded emissions: 110 tons of carbon dioxide/1000 tons olivine; Absorption efficiency: 3 moles ALK/mole olivine; Dissolution constant: Log(r)=−8.75 (may vary depending on pH/temp)

Carbon Removal Prediction

In another aspect, the present disclosure provides systems and methods for predicting rates of carbon removal at specific sites. Such predictions may be based on, for example, data corresponding to measurement of changes in alkalinity, pCO2, pH, and/or water temperature. The predictions may be generated using algorithms and software interpreting such data. The algorithms and software may be implemented by way of one or more models that can be generated based on the MRV data obtained using various sensors as described elsewhere herein.

In some embodiments, the predicted rates of carbon removal may be used to inform how the properties of the olivine sand and/or the preparation of the olivine sand and the placement design can be optimized for improved/increased/more efficient carbon removal.

Computer Systems

Figure 10:
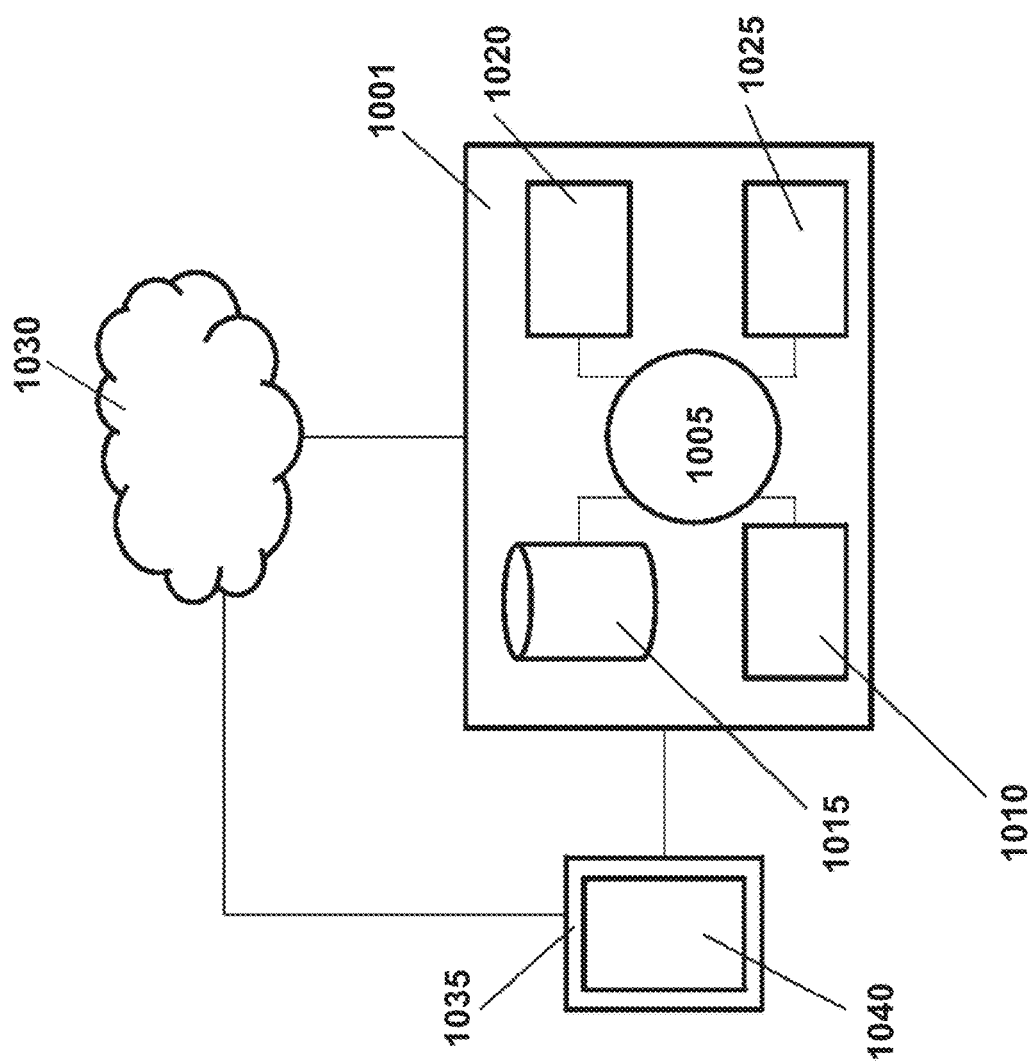
FIG. 10 schematically illustrates a computer system that is programmed or otherwise configured to implement methods provided herein.
Figure 11:
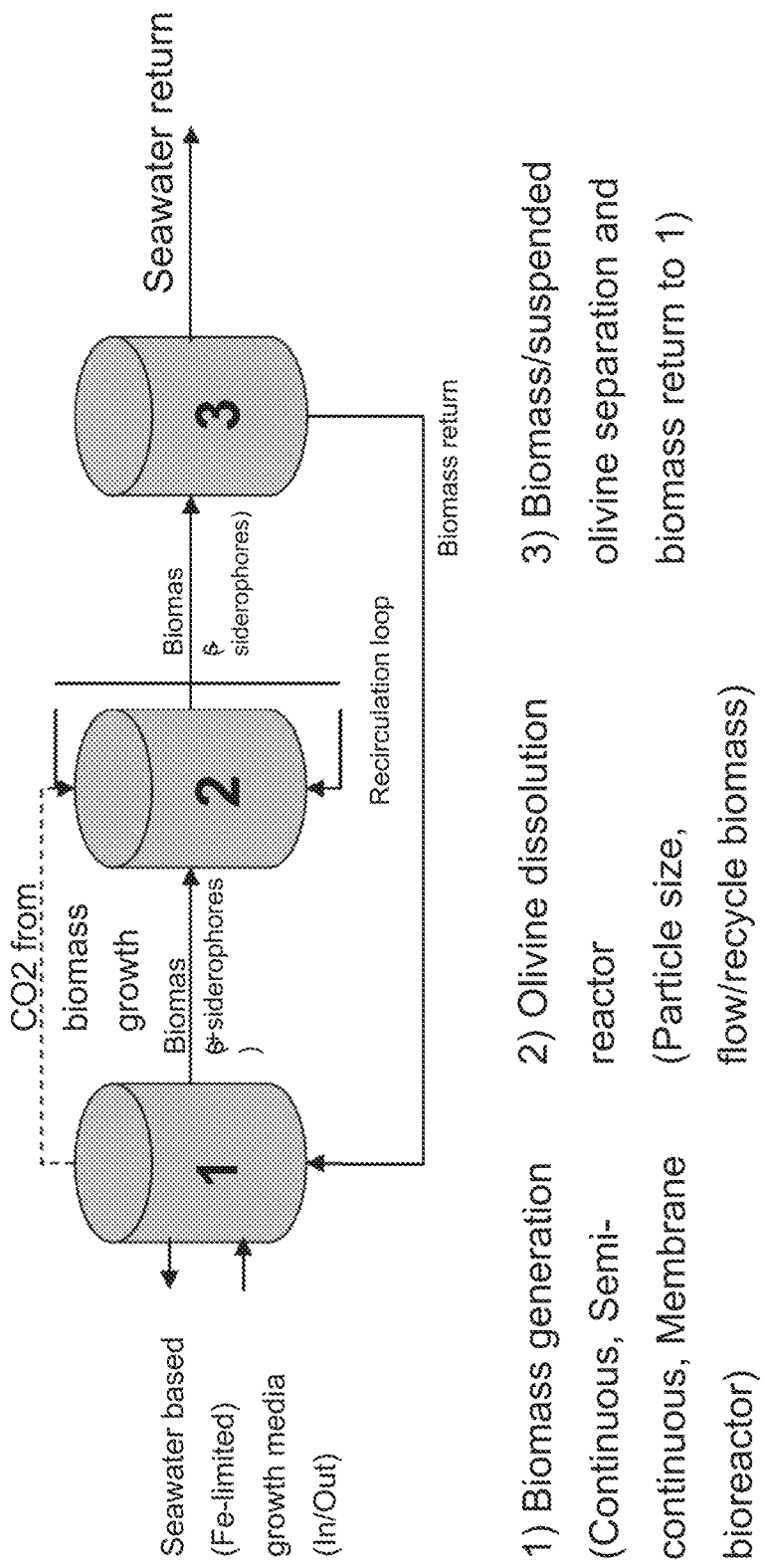
FIG. 11 schematically illustrates an exemplary reactor configured to intake seawater that may be mixed with olivine and microbial biomass to generate alkalinity.

In an aspect, the present disclosure provides computer systems that are programmed or otherwise configured to implement methods of the disclosure, e.g., any of the subject methods for processing and distributing olivine. FIG. 10 shows a computer system 1001 that is programmed or otherwise configured to implement a method for olivine processing and distribution. The computer system 1001 may be configured to, for example, (i) identify a target site, (ii) optimize one or more procedures for processing olivine to yield favorable properties or characteristics for the olivine, based on the target site identified, and (iii) coordinate transportation of the olivine to the target site. The computer system 1001 can be an electronic device of a user or a computer system that is remotely located with respect to the electronic device. The electronic device can be a mobile electronic device.

The computer system 1001 may include a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are located external to the computer system 1001 (e.g., on a remote server that is in communication with the computer system 1001 through an intranet or the Internet).

The computer system 1001 can communicate with one or more remote computer systems through the network 1030. For instance, the computer system 1001 can communicate with a remote computer system of a user (e.g., an end user performing or monitoring the processing and/or the transportation or distribution of the olivine). Examples of remote computer systems include personal computers (e.g., portable PC), slate or tablet PC's (e.g., Apple® iPad, Samsung® Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, a portal for a user to monitor the processing and/or the transportation or distribution of the olivine. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1005. For example, the algorithm may be configured to identify a target site and optimize a procedure for processing the olivine based on the properties or the characteristics of the target site.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for quantifying carbon sequestration derived from dissolution of carbon-removing sand, comprising:
   a. obtaining (i) one or more measurements from at least one sensor or (ii) one or more readings from at least one instrument;
   b. validating or updating one or more models for determining or predicting transport of said carbon-removing sand, dissolution of said carbon-removing sand, carbon sequestration resulting from said carbon-removing sand, or one or more chemical fluxes associated with the dissolution of said carbon-removing sand in a target environment based on said one or more measurements or said readings;
   c. using said one or more models to determine or predict an amount of carbon dioxide removal, wherein said one or more models generates at least a spatial-temporal atmospheric carbon dioxide removal amount of a total project, wherein said one or more models comprise a model of sand transport, sand dissolution, carbon sequestration or chemical fluxes; and
   d. subtracting project emissions ascertained by a project-specific life-cycle analysis from a gross atmospheric carbon dioxide drawdown to calculate a net atmospheric carbon dioxide drawdown.

2. The method of claim 1, wherein said quantifying said carbon sequestration is measured, reported, and verified to an extent sufficient to satisfy one or more third-party standards for creditization of removal of atmospheric carbon.

3. The method of claim 1, wherein a first model of said one or more models is a sediment transport model, wherein a second model of said one or more models is a carbon sequestration model resulting from carbon-removing sand, and wherein said second model is based, at least in part, on an output of said first model.

4. The method of claim 1, wherein a target environment of said carbon sequestration comprises an aquatic environment or a microcosm or mesocosm representing said target environment.

5. The method of claim 1, further comprising, prior to (a), providing a sand blend comprising an alkaline material to said target environment.

6. The method of claim 5, wherein said sand blend comprising said alkaline material further comprises at least a portion of native or allochthonous sand at said target environment.

7. The method of claim 6, further comprising, prior to (a), pre-processing said alkaline material to produce a processed alkaline material having a target property, wherein said pre-processing said alkaline material comprises grinding the alkaline material to achieve a target grain size or a desired range of grain sizes.

8. The method of claim 1, wherein said one or more models are configured to identify one or more candidate locations for deployment of said mixture based on water chemistry data, temperature data, water movement data, wave data, tide data, current data, native sediment characteristics, or a water depth of said one or more locations in said target site.

9. A method for removing atmospheric carbon dioxide comprising:
   a. deploying a composition comprising carbon-removing sand at a target site; and
   b. measuring, modeling, or deriving one or more parameters that directly or indirectly quantifies an amount of atmospheric carbon dioxide captured via said carbon-removing sand.

10. The method of claim 9, wherein said composition comprises (i) non-carbon removing sand and (ii) said carbon removing sand.

11. The method of claim 10, wherein said composition is homogenous and further comprises:
   (a) said carbon-removing sand and said non-carbon-removing sand mechanically combined prior to, or during sand deployment; and
   (b) said carbon-removing sand and said non-carbon-removing sand naturally combined following sand deployment.

12. The method of claim 10, wherein said composition is heterogenous and further comprises:
   (a) a first layer comprising said carbon-removing sand, wherein said carbon removing sand comprises an alkaline material, and
   (b) a second layer comprising said non-carbon-removing sand, wherein said first layer is positioned above said second layer to enhance a rate of weathering of said alkaline material.

13. The method of claim 9, further comprising, prior to (a), selecting said target site based on at least one or more geographic, environmental, geologic or other physical or chemical parameters.

14. The method of claim 13, wherein said one or more parameters comprise a property of the target site, wherein said property comprises a partial pressure of carbon dioxide (pCO2), dissolved inorganic carbon (DIC), alkalinity, pH, or nutrients.

15. The method of claim 13, wherein said one or more parameters comprise a physical condition of said target site.

16. The method of claim 15, wherein said physical condition comprises a hydrodynamic feature or other natural condition.

17. The method of claim 9, wherein in (a), said composition is deployed using an aquatic vehicle.

18. The method of claim 9, wherein in (a), said composition is deployed via dredging.

19. The method of claim 9, wherein said deployment of said mixture in said one or more locations (i) increases or enhances dissolution of said ultramafic material in said mixture, or (ii) facilitates coastal construction.

* * * * *